(12) United States Patent
Feng et al.

(10) Patent No.: US 12,291,513 B2
(45) Date of Patent: May 6, 2025

(54) PYRIDINIUM DERIVATIVES MADE BY HYDROTHERMAL SYNTHESIS FOR USE AS ANOLYTES IN ELECTROCHEMICAL CELLS

(71) Applicant: Wisconsin Alumni Research Foundation, Madison, WI (US)

(72) Inventors: Dawei Feng, Madison, WI (US); Xiuliang Lyu, Madison, WI (US); Patrick Sullivan, Madison, WI (US); Wenjie Li, Ithaca, NY (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/734,377

(22) Filed: May 2, 2022

(65) Prior Publication Data
US 2022/0363663 A1    Nov. 17, 2022

Related U.S. Application Data

(60) Provisional application No. 63/183,162, filed on May 3, 2021.

(51) Int. Cl.
| | |
|---|---|
| *C07D 401/04* | (2006.01) |
| *H01M 8/08* | (2016.01) |
| *H01M 8/18* | (2006.01) |

(52) U.S. Cl.
CPC ............ *C07D 401/04* (2013.01); *H01M 8/08* (2013.01); *H01M 8/188* (2013.01); *H01M 2300/0002* (2013.01)

(58) Field of Classification Search
CPC ..... C07D 401/04; C07D 213/04; H01M 8/08; H01M 8/188; H01M 2300/0002
See application file for complete search history.

(56) References Cited

U.S. PATENT DOCUMENTS

| | | | |
|---|---|---|---|
| 9,793,566 | B2 | 10/2017 | Liu et al. |
| 10,934,258 | B2 | 3/2021 | Liu et al. |
| 11,271,238 | B2 | 3/2022 | Liu |
| 2018/0072669 | A1 | 3/2018 | Liu et al. |
| 2020/0373599 | A1 | 11/2020 | Gordon et al. |

FOREIGN PATENT DOCUMENTS

| | | |
|---|---|---|
| CN | 111362867 | 7/2020 |
| CN | 111564649 A | 8/2020 |
| CN | 112103546 A | 12/2020 |
| JP | 53-132485 | 11/1978 |
| JP | H06308677 A | 11/1994 |
| WO | WO 2017/025177 A1 | 2/2017 |
| WO | 2022251610 A1 | 12/2022 |

OTHER PUBLICATIONS

STN Registry entry for CAS RN 2493174-12-0, Accessed Nov. 3, 2023, Entry Date Oct. 21, 2020.*
STN Registry database entry for CAS RN 1359938-74-1, entry date Mar. 6, 2012; accessed May 18, 2024.*
STN Registry database entry for CAS RN 777813-82-8, entry date Nov. 9, 2004; accessed May 18, 2024.*
Chemical abstract compounds, STNext, RN 153578-59-7 (Entered STN: Mar. 11, 1994), RN 1402214-78-1 (Entered STN: Oct. 29, 2012), RN 1034732-39-2 (Entered STN: Jul. 18, 2008), pp. 1-2.
Wang, Z. et al., "Well-defined polymers containing a single midchain viologen group: synthesis, environment-sensitive fluorescence, and redox activity", Polymer chemistry, 2016, vol. 7, No. 26, pp. 4402-4410 (internal pp. 1-8).
International Search Report and Written Opinion for International Application No. PCT/US2022/072036, mailed on Aug. 10, 2022, pp. 1-11.
Jin, Shijian, et al. "Near neutral pH redox flow battery with low permeability and long-lifetime phosphonated viologen active species." *Advanced Energy Materials* 10.20 (2020): 2000100.
Ding, Junjie, et al. "Viologen-inspired functional materials: synthetic strategies and applications." *Journal of Materials Chemistry A* 7.41 (2019): 23337-23360.
Liu, Wanqiu, et al. "A highly stable neutral viologen/bromine aqueous flow battery with high energy and power density." *Chemical Communications* 55.33 (2019): 4801-4804.
Luo, Jian, et al. "Materials challenges of aqueous redox flow batteries." *MRS Energy & Sustainability* 9.1 (2022): 1-12.
Liu, Yahua, et al. "Screening viologen derivatives for neutral aqueous organic redox flow batteries." *ChemSusChem* 13.9 (2020): 2245-2249.
Liu, Yahua, et al. "Supporting Information: Screening viologen derivatives for neutral aqueous organic redox flow batteries." *ChemSusChem* 13.9 (2020): 2245-2249.
Li, Hongbin, et al. "Spatial Structure Regulation: A Rod-Shaped Viologen Enables Long Lifetime in Aqueous Redox Flow Batteries." *Angewandte Chemie* 133.52 (2021): 27177-27183.
Huang, Mingbao, et al. "Five-Membered-Heterocycle Bridged Viologen with High Voltage and Superior Stability for Flow Battery." *Advanced Functional Materials* 32.16 (2022): 2111744.
Ambrose, Bebin, et al. "Modified viologen as an efficient anolyte for aqueous organic redox flow batteries." *Materials Letters* 314 (2022): 131876.
Han, Juntian, et al. "Two-Electron Storage Viologen for Aqueous Organic Redox Flow Batteries." *Chemical Journal of Chinese Universities-Chinese* 41.5 (2020): 1035-1041.
Feng, Dawei. "Battery technologies for grid scale energy storage: inorganic or organic? flow or non-flow?" University of Wisconsin-Madison Materials Science and Engineering. pp. 31; presentation on Apr. 6, 2022.

(Continued)

*Primary Examiner* — Alicia L Otton
(74) *Attorney, Agent, or Firm* — Bell & Manning, LLC

(57) ABSTRACT

Pyridinium derivatives, methods of making the pyridinium derivatives, and electrochemical cells that use the pyridinium derivatives as anolytes are provided. The pyridinium derivatives have a redox core with two or more pyridinium groups and substituents at pyridinium ring nitrogen atoms. The pyridinium derivatives can be made by reacting pyridyl reactant molecules having two or more pyridyl groups with water-soluble derivatizing reactant molecules via a hydrothermal synthesis.

8 Claims, 35 Drawing Sheets

(56) References Cited

OTHER PUBLICATIONS

Kwabi, David G., Yunlong Ji, and Michael J. Aziz. "Electrolyte lifetime in aqueous organic redox flow batteries: a critical review." Chemical Reviews 120.14 (2020): 6467-6489.

Beh, Eugene S., Diana De Porcellinis, Rebecca L. Gracia, Kay T. Xia, Roy G. Gordon, and Michael J. Aziz. 2017. "A Neutral pH Aqueous Organic-Organometallic Redox Flow Battery with Extremely High Capacity Retention." ACS Energy Letters 2 (3) (Feb. 13): 639-644.

Liu, Yahua, et al. "A long-lifetime all-organic aqueous flow battery utilizing TMAP-TEMPO radical." Chem 5.7 (2019): 1861-1870.

Hu, Bo, et al. "Improved radical stability of viologen anolytes in aqueous organic redox flow batteries." Chemical communications 54.50 (2018): 6871-6874.

Rabenau, Albrecht. "The role of hydrothermal synthesis in preparative chemistry." Angewandte Chemie International Edition in English 24.12 (1985): 1026-1040.

Singh, Vikram, et al. "Aqueous organic redox flow batteries." Nano Research 12.9 (2019): 1988-2001.

DeBruler, Camden, et al. "Designer two-electron storage viologen anolyte materials for neutral aqueous organic redox flow batteries." Chem 3.6 (2017): 961-978.

Han, Juntian, Yaoxing Cui, Zhijun Su, Yi Wu, Liuping Chen, and Junhui Xu. "Two-Electron Storage Viologen for Aqueous Organic Redox Flow Batteries." Chemical Journal of Chinese Universities-Chinese vol. 41, No. 5 (2020): 1035-1041.

English Abstract for Han, Juntian, Yaoxing Cui, Zhijun Su, Yi Wu, Liuping Chen, and Junhui Xu. "Two-Electron Storage Viologen for Aqueous Organic Redox Flow Batteries." Chemical Journal of Chinese Universities-Chinese vol. 41, No. 5 (2020): 1035-1041.

Bourque, et al., "Characterization of Quaternary Ammonium Oligomers by Paired-Ion Reversed-Phase Liquid Chromatography-Mass Spectrometry," Analytical Chemistry, Mar. 23, 2005, pp. 2810-2817, vol. 77, No. 9, XP093173000, US ISSN: 0003-2700, DOI: 10.1021/ac048868I.

Engel, et al., "New Cations for Ionic Liquids, Including Chiral Adjuncts with Phosphate and Sulfonylimide Anions" In: "Ionic Liquids in Organic Synthesis", American Chemical Society, Washington, DC, Jan. 18, 2007, pp. 259-266, vol. 950, XP055555943, ISBN: 978-0-8412-2068-3 DOI: 10.1021 / bk-2007-0950.ch020.

Extended European Search Report in EP Patent Application No. 22776810.8 dated Jul. 5, 2024, 9 pages.

Hashimoto, et al., "An Acid-Activatable Fluorescence Probe for Imaging Osteocytic Bone Resorption Activity in Deep Bone Cavities", Angewandte Chemie International Edition, Verlag Chemie, Hoboken, USA, Sep. 8, 2020, pp. 20996-21000, vol. 59, No. 47, 8XP072102384, ISSN: 1433-7851, DOI: 10.1002/ANIE.202006388.

\* cited by examiner

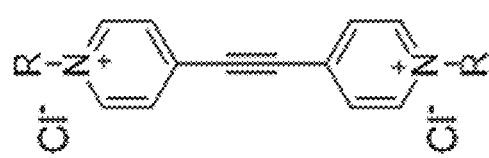 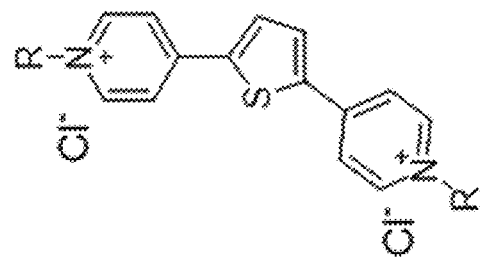
 
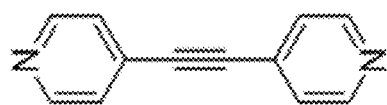 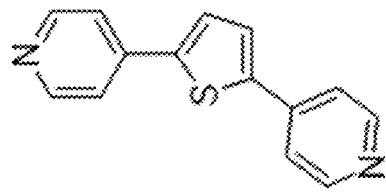
FIG. 1D
FIG. 1E

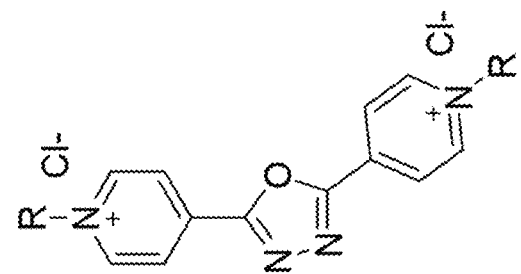
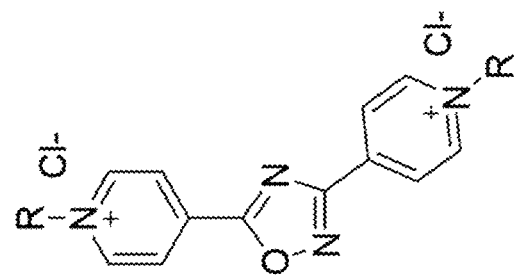
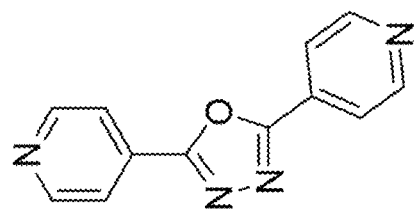
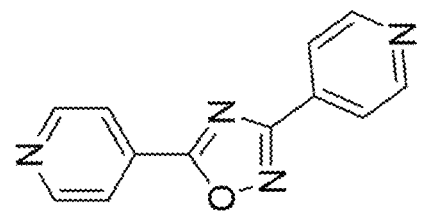
FIG. 1H
FIG. 1I

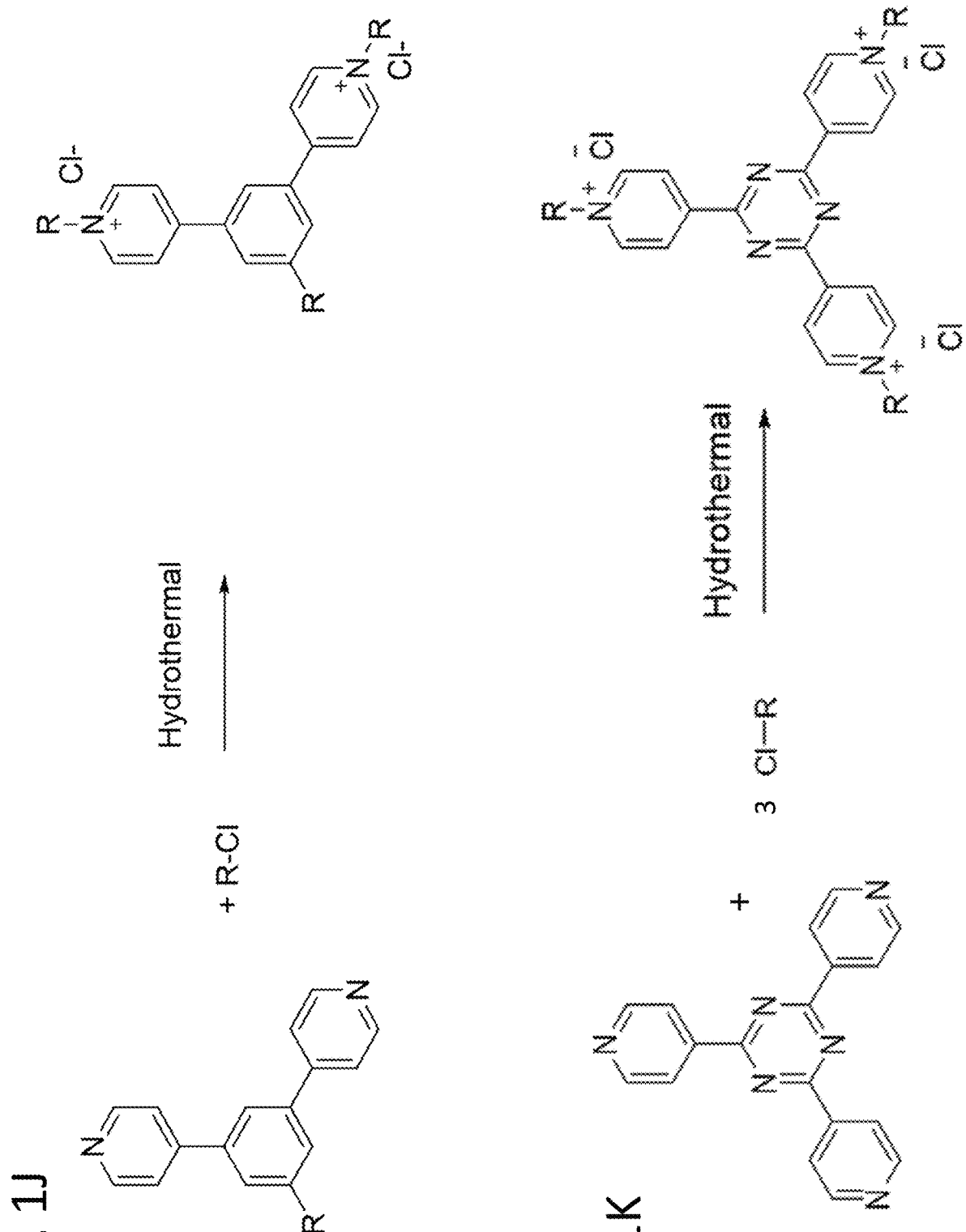

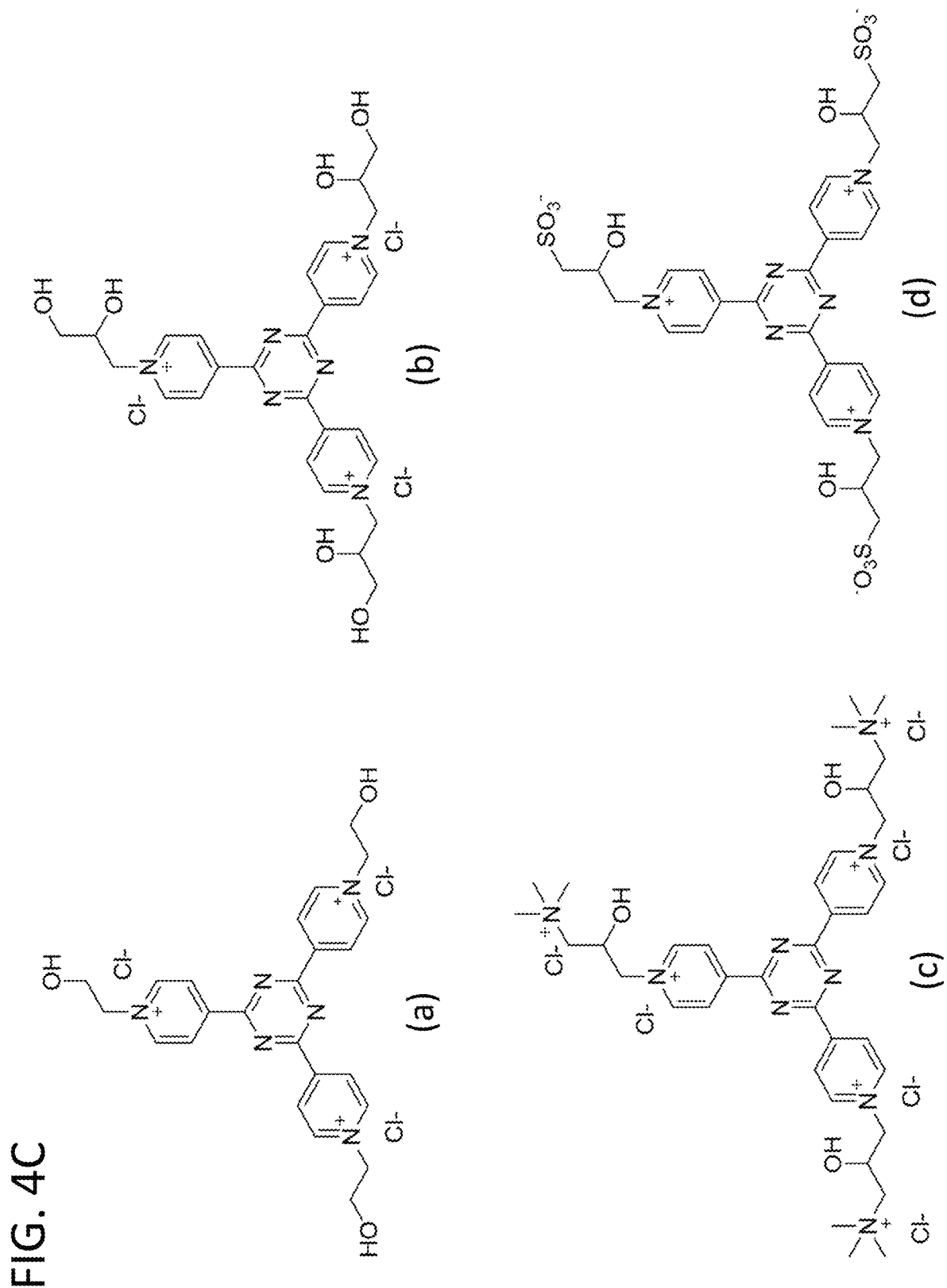

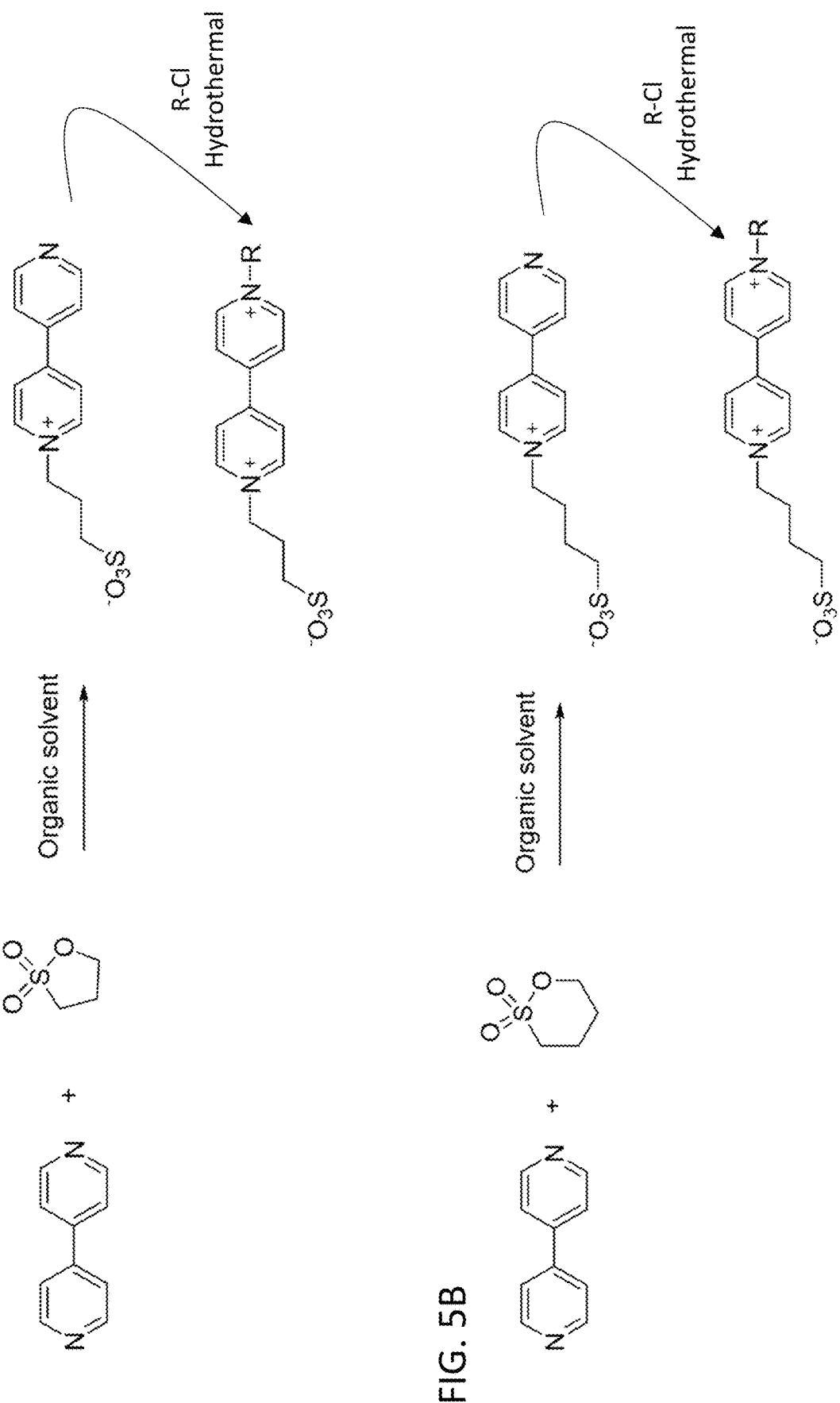

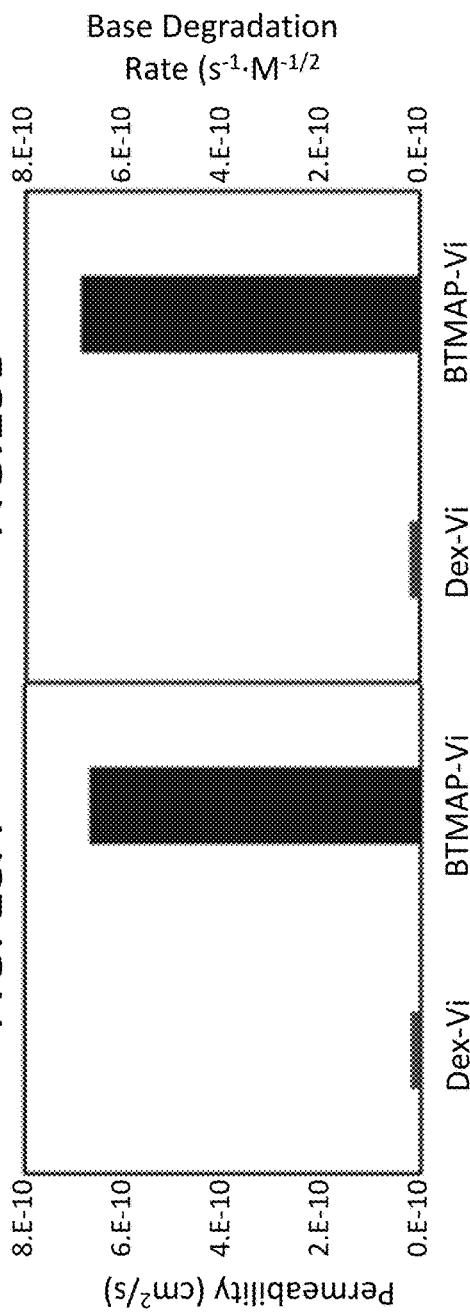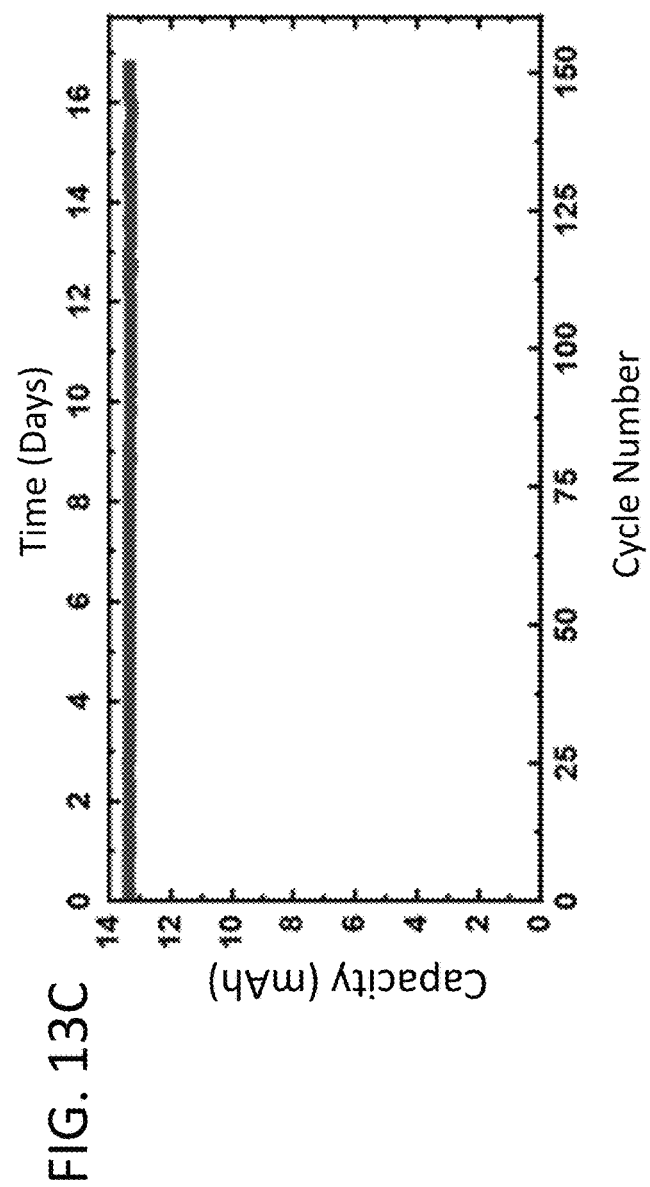
FIG. 13A  FIG. 13B  FIG. 13C

PYRIDINIUM DERIVATIVES MADE BY HYDROTHERMAL SYNTHESIS FOR USE AS ANOLYTES IN ELECTROCHEMICAL CELLS

CROSS-REFERENCE TO RELATED APPLICATIONS

The present application claims priority to U.S. provisional patent application No. 63/183,162 that was filed on May 3, 2021, the entire contents of which are incorporated herein by reference.

BACKGROUND

An increasing number of renewable energy sources are being integrated into the electric grid in the US and around the world. In addition to environmental and health concerns regarding emissions of dirty fuels and the reliability issues surrounding importing fossil fuels, the development of low cost solar and wind power generation has been the main driving force. However, as intermittent wind and solar begin to approach more than a quarter of grid energy production, significant energy storage technology must be employed to mitigate the unbalanced energy production and demand on the grid.

One approach to grid energy storage is the use of redox flow batteries (RFBs), which have decoupled energy and power scaling because the capacity can be enlarged by simply expanding the size of the storage tanks. This decoupling of capacity and power allows for simplified design of long-storage-duration devices by increasing the amount of active energy storage materials without concurrently needing to increase the electrode sizes. Despite this practical advantage, RFBs have only been commercially implemented in a handful of experimental grid applications. This is partially due to the high and volatile cost of active materials, typically vanadium, in most commercial RFBs. Aqueous Organic Redox Flow Batteries (AORFBs) are a promising approach to utilizing the scalability of liquid-state energy storage while reducing the materials cost by replacing vanadium redox species with cheaper organic redox molecules. However, developing organic redox active species that are simultaneously aqueous soluble, chemically stable, membrane compatible, and cost effective remains difficult.

Among the plethora of aqueous organic redox species, bis(3-trimethylammonio)propyl viologen tetrachloride (BTMAP-Vi) has emerged as a promising aqueous anolyte due to its high water solubility, compatibility with anion-exchange membranes, and stability in neutral aqueous solution. (Beh, E. S. et al., *ACS Energy Lett.* 2017, 2(3), 639-644; DeBruler, C. et al., *Chem* 2017, 3 (6), 961-978; Liu, Y. et al., *Chem* 2019, 5, 1861-1870; Hu, B. et al. *Chem. Commun.* 2018, 54 (50), 6871-6874; and Liu, Y. et al., *ChemSusChem* 2020, 13(9), 2245-2249.)

Although BTMAP-Vi consists of earth-abundant atoms due to its organic nature, the synthetic procedures used to make it pose some sustainability and cost concerns. The original synthetic procedure requires 1-bromo-3-chloropropane and trimethyl amine starting materials in excess to drive the reaction forward, large amounts of expensive solvents (DMF, methyl tert-butyl ether, and isopropanol) to obtain pure product, and an ion-exchange step to replace the bromide counter-anion for chloride, but only produces a low overall yield of 44%. (Beh, et al., 2017.) This procedure has been slightly altered by removing the need for the ion-exchange step. (Liu et al., 2019.) However, the modified method involved the use of an even more expensive starting material, 1,3-dichloropropane, and resulted in a drastically decreased overall yield of only 13%. The tetrabromide salt of BTMAP-Vi can be obtained at relatively high yield of 68% in a single-step reaction. (DeBruler et al., 2017.) However, using bromide as the counter ion for positively charged viologen derivatives suffers from several disadvantages. First, the bromine/bromide redox couple has a formal potential of 1.09 V, which may interfere with high potential cathodic reactions in RFBs. Second, bromide has lower conductivity than chloride through commonly used anion exchange membranes (AEMs) for positively charged viologen derivatives, resulting in diminished power. Finally, the bromide salt form of viologen derivatives have lower aqueous solubility, higher viscosity, and increased mass, diminishing both volumetric and gravimetric energy density.

SUMMARY

Pyridinium derivatives, methods of making the pyridinium derivatives, and electrochemical cells incorporating the pyridinium derivatives as anolytes are provided.

Some examples of the pyridinium derivative include at least two pyridinium groups, wherein the nitrogen atom of a pyridinium ring of at least one of the pyridinium groups has a substituent comprising a secondary alcohol on an alkyl chain. In these illustrative examples, at least one of the two following criteria is met: the pyridinium derivative is an asymmetric pyridinium derivative; and/or the substituent comprising the secondary alcohol has a non-hydroxyl terminal group.

An example of an electrochemical cell that incorporates a pyridinium derivative of a type described herein includes: an anode; an anolyte in contact with the anode, the anolyte comprising one or more pyridinium derivatives of a type described herein; a cathode; and a catholyte in contact with the cathode.

An example of making a pyridinium derivative using hydrothermal synthesis includes the steps of: forming an aqueous solution comprising a first reactant having two or more pyridyl groups and a second reactant comprising an organic compound having a leaving group and a derivatizing group; and reacting the first reactant with the second reactant in the aqueous solution at a temperature and a pressure, wherein the temperature is higher than the boiling point of water at the pressure, to form a compound having at least two pyridyl groups, at least one of the pyridyl groups being substituted at its pyridine ring nitrogen atom with the derivatizing group.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIGS. 4A, panels (a)-(f), and 4B, panels (a)-(h), show the structures of some illustrative examples of 4,4'-bipyridinium derivatives that can be made using the reaction of FIG. 1A and some of the derivatizing reactant molecules of FIG. 3, panels (a)-(j).

FIGS. 5A-5D show illustrative two-step reaction schemes for pyridinium derivatives.

FIG. 13A shows the results of permeability measurements for Dex-Vi and BTMAP-Vi through an anion exchange membrane (DSVN).

FIG. 13B shows the results of degradation measurements for Dex-Vi and BTMAP-Vi.

FIG. 13C shows the chemical stability of the first redox processes of Dex-Vi using a symmetric, volumetrically-unbalanced flow cell inside an $N_2$ glovebox over sixteen days (150 cycles) of continuous charge-discharge cycling.

DETAILED DESCRIPTION

Figures 1A, 1B, 1C:
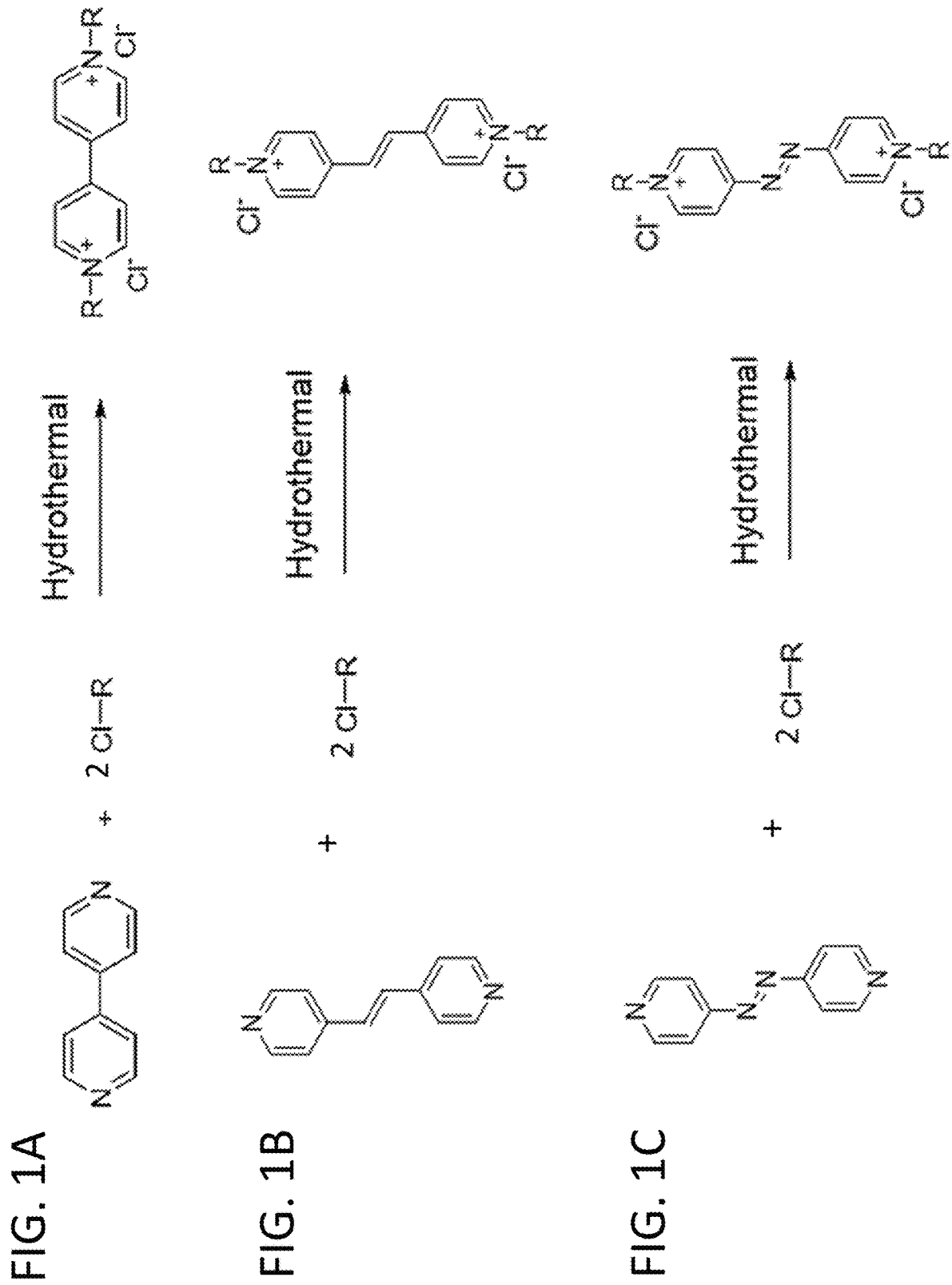
FIGS. 1A-1O show examples of bipyridinium (FIG. 1A-1J), tripyridinium (FIG. 1K-1N), and tetrapyridinium (FIG. 1O).
Figures 1F, 1G:
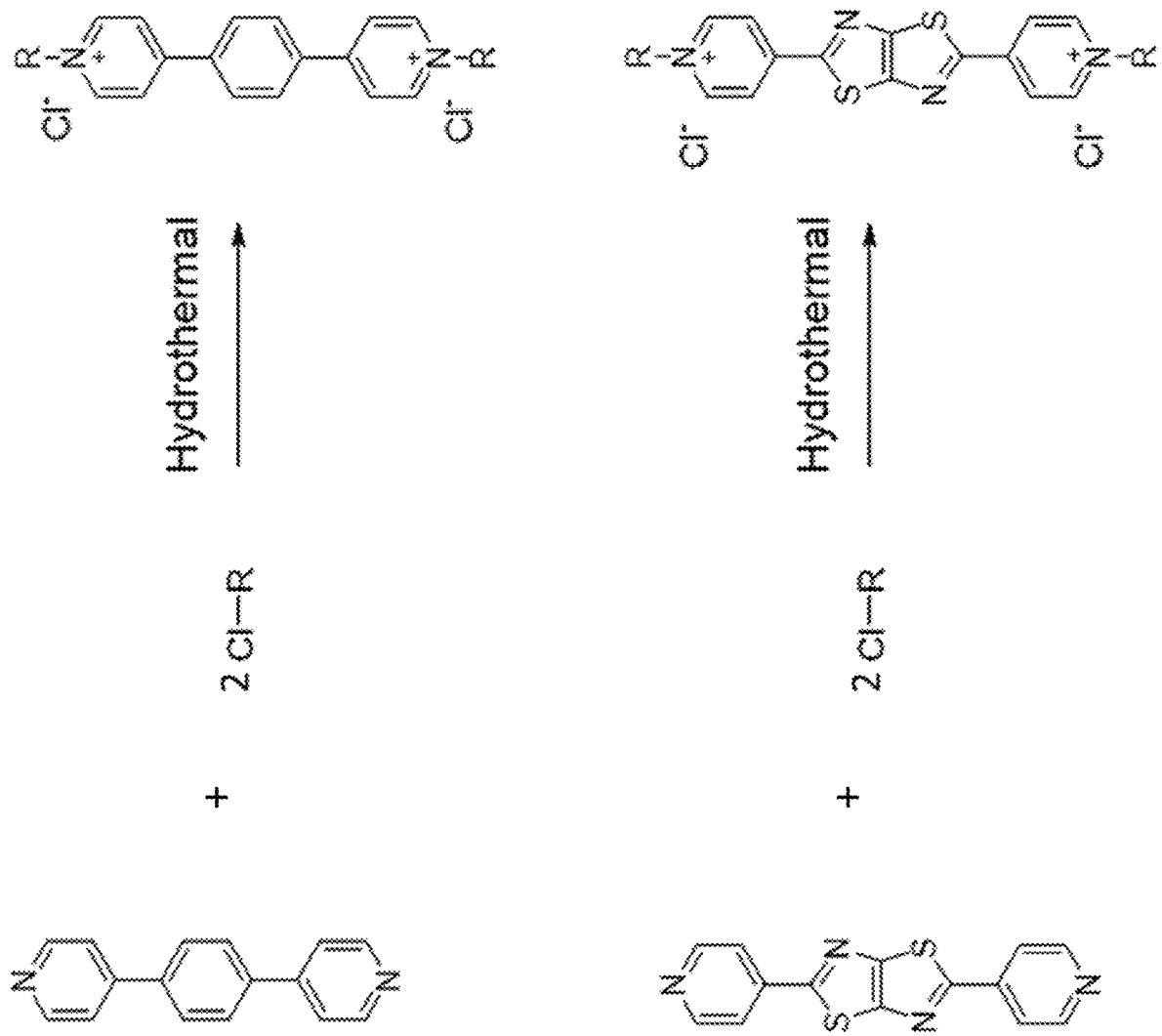
Figure 1L:
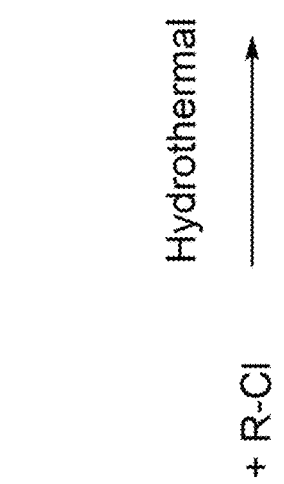
Figure 1L:
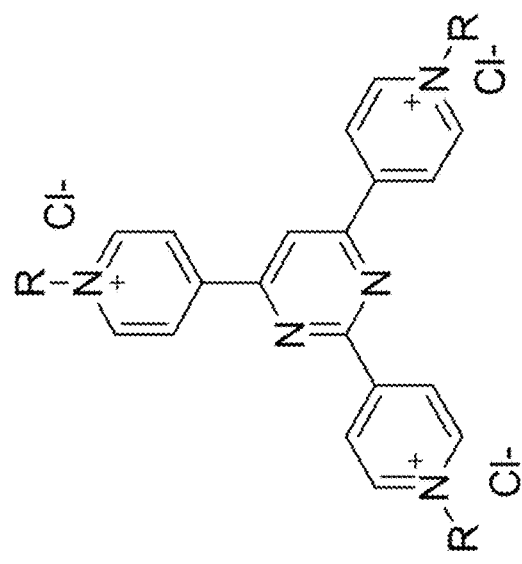
Figure 1M:
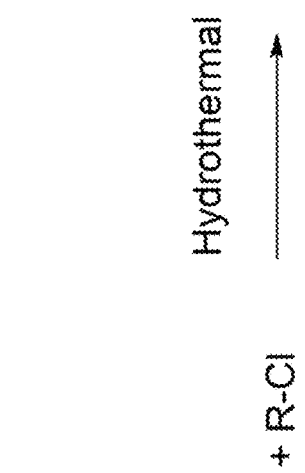
Figure 1M:
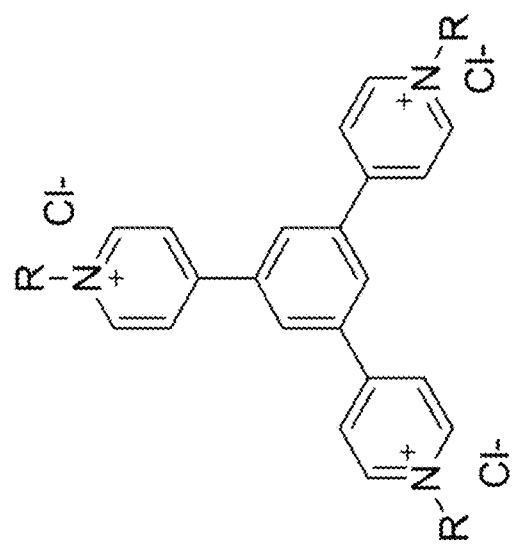

Pyridinium derivatives, methods of making the pyridinium derivatives, and electrochemical devices, such aqueous organic redox flow batteries, that use the pyridinium derivatives as anolytes are provided.

The pyridinium derivatives can be made by reacting pyridyl reactant molecules having two or more pyridyl groups with derivatizing reactant molecules via a simple and effective, scalable hydrothermal synthesis. Many of the reactant molecules are inexpensive and readily commercially available. As a result, bulk quantities of the pyridinium derivatives can be made in a cost-effective manner. Because the reactants, the intermediates, and the products of the hydrothermal syntheses are water-soluble, water can be used as the solvent, making the use of hydrothermal synthesis possible. For example, some reactants, intermediates, and/or products have molar solubilities in water of 1 M or greater at 23° C.

The hydrothermal synthesis is carried out in aqueous solution at temperatures above the boiling point of the water at the pressure under which the hydrothermal synthesis is being carried out. As used herein, the term "aqueous solution" refers to a solution in which water is present as a solvent. Water may be the only solvent present in an aqueous solution, but water may also be mixed with one or more organic solvents in an aqueous solution. In various embodiments of the mixed water-organic solvent aqueous solutions, water makes up at least 10 vol. %, at least 20 vol. %, or at least 50 vol. % of the solvent mixture. The hydrothermal syntheses can also be carried out at ambient pressure (e.g., at or about 1 atm) or at pressures above ambient. An autoclave or similar pressure reaction vessel can be used to achieve an elevated pressure (i.e., a pressure greater than ambient). The optimum temperature, pressure, and reaction time will depend on the particular reactants being used. Generally, the pyridinium derivatives can be synthesized at temperatures in the range from 50° C. to 200° C., including from 80° C. to 150° C. Pressures in the range from 100 kPa to 1000 kPa are generally suitable. However, temperatures and pressures outside of these ranges can be used.

Various embodiments of the pyridinium derivatives have physical and electrochemical properties, including water solubilities, redox potentials, electrochemical kinetics, voltage, and/or cycling stabilities in neutral aqueous solution, that render them well-suited for use as anolytes in electrochemical devices, including AORFBs. The pyridinium derivatives can be synthesized as chloride salts without the need for an ion-exchange step, which is advantageous for AORFB applications because chloride has a higher conductivity through commonly used anion exchange membranes than other anions, such as bromide, that are used in AOR-FBs. Additionally, chloride has a high oxidation potential, which is ideal for AORFBs with high potential cathodic reactions. In addition, the chloride salts typically have higher aqueous solubilities, lower viscosities, and reduced mass which enhances their volumetric and gravimetric energy densities/capacities, relative to their corresponding bromide salts. The lower reactivity of the chloro-reactants can be enhanced by the high-temperature, high-pressure conditions of the hydrothermal synthesis.

The pyridyl reactants are organic molecules that have two pyridyl groups (dipyridyls), three pyridyl groups (tripyridyls), four pyridyl groups (tetrapyridyls), or more than four pyridyl groups, which provide a redox core upon forming pyridinium products. The pyridine rings of the pyridyl groups may be substituted or unsubstituted at the ring carbon atoms. The pyridyl groups may be, but are not necessarily, 4-pyridyl groups. However, the pyridine nitrogen need not be in the 4-position of the pyridyl group; it may be, for example, at the 2-position.

Figures 1N, 1O:
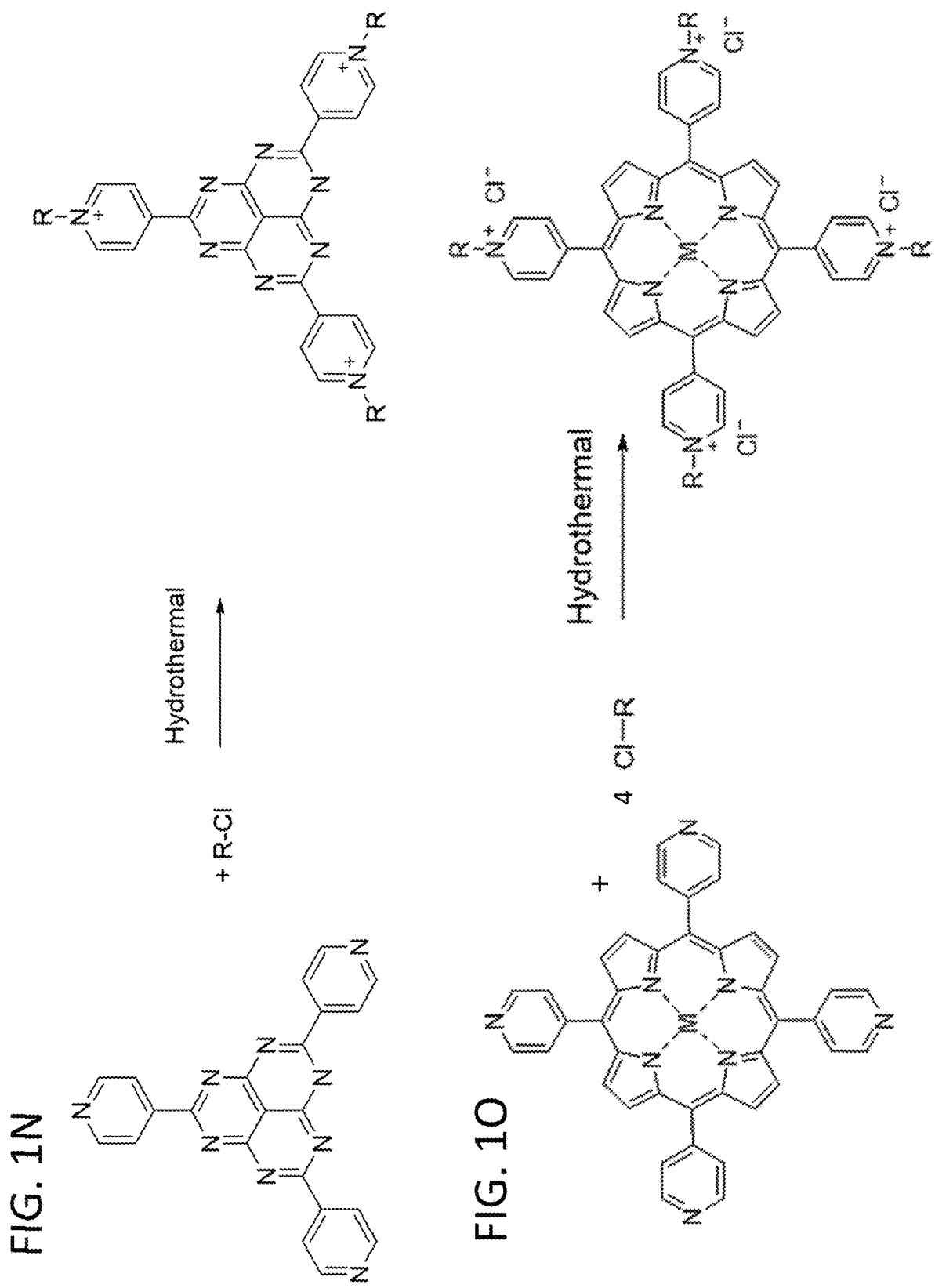

FIGS. 1A-1O show some examples of dipyridinium (FIGS. 1A-1J), tripyridinium (FIGS. 1K-1N), and tetrapyridinium (FIG. 1O) reactant molecules, and the reaction products produced upon a hydrothermal reaction with a generic derivatizing chloro-reactant molecule ("Cl—R") are shown in FIGS. 1A-1O.

As shown in FIG. 1A, 4,4'-bipyridine (also referred to as 4,4'-dipyridyl) is one example of a dipyridyl reactant that can be derivatized via a hydrothermal synthesis; the products of said synthesis being viologens. Extended bipyridines can also be used, as illustrated in FIGS. 1B-1J. As used herein, the term extended bipyridines refers to molecules having two pyridyl groups connected at one of their pyridine ring carbon atoms by a linker comprising one or more atoms. The generic structure for an extended bipyridine can be represented by the structure:

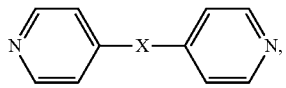

wherein X represents the linker. For example, the linker may consist of, or may comprise, a conjugated carbon-carbon bond, such as a carbon-carbon double bond or a carbon-carbon triple bond, a nitrogen-nitrogen double bond, an aromatic ring, a heteroaromatic ring, or two or more fused aromatic or heteroaromatic rings. By way of illustration, the linker X group in FIGS. 1B-1I represents a C=C, an N=N, a C≡C bond, an $SC_4H_2$ heteroaromatic ring, a $C_6H_4$ aromatic ring, a $S_2N_2C_4$ fused heteroaromatic ring system, and a $C_2N_2O$ aromatic ring (e.g., 1,3,4-oxadiazone or 1,2,4-oxadiazole), respectively. Optionally, one or more C-atoms on an aromatic or heteroaromatic ring in a linker may be substituted, as shown in FIG. 1J, where $R_1$ can be a hydrogen atom or one the following functional groups: alkyl groups (e.g., —$CH_3$), a polyethylene glycol (PEG) (e.g., —$OCH_2CH_2$-[EG]$_n$, wherein n is an integer in the range from 1 to 5), carboxylic or carboxylate (e.g., —COOM, where M is H, $NH_4$, Na, or K), sulfonate (—$SO_3^-$), phosphonate (—$PO_3^{2-}$), or an alkyl quaternary ammonium (—$CH_3NR'''_3^+$, where $R'''_3^+$ is an alkyl group). Illustrative tripyridyl reactants include pyridyl-substituted triazines, pyrimidines, benzenes, and porphyrin, such as 2,4,6-tri-4-pyridyl-1,3,5-triazine (FIG. 1J), 2,4,6-tris(4-pyridyl)pyrimidine (FIG. 1L), 1,3,5-tri(4-pyridyl)-benzene (FIG. 1M) and hexaazaphenalene (FIG. 1N). Illustrative tetrapyridyl reactants include pyridyl-substituted metal porphyrins, such as a metal 5,10,15,20-tetra(4-pyridyl)porphyrin (FIG. 1O).

Figure 2:
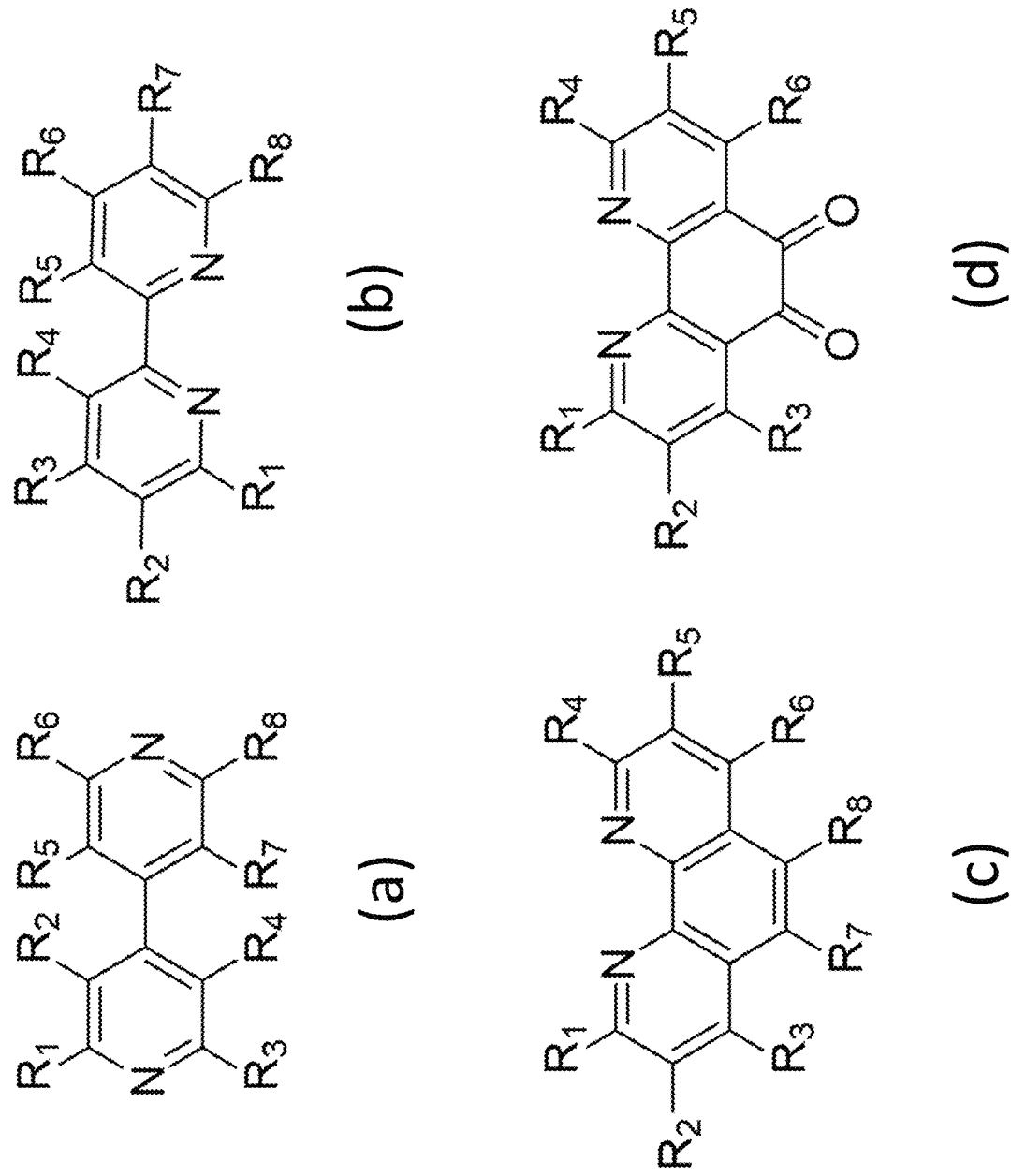
FIG. 2, panels (a)-(d), shows pyridine ring-substituted dipyridyl reactants using substituted 4,4'-bipyridine (FIG. 2, panels (a) and (b)) and substituted fused bipyridines (FIG. 2, panels (c) and (d)) as illustrative examples.

Although the pyridine ring carbon atoms of the pyridyl reactants shown in FIGS. 1A-1O are unsubstituted, it should be noted that the various pyridyl reactants described herein, as well as the pyridinium derivates made therefrom, may have substituents at one or more of their ring carbons. It should also be understood that, for the purposes of this disclosure, the term pyridyl group includes pyridyl groups that are incorporated into fused heterocycles. By way of illustration, pyridine ring-substituted dipyridyl reactants are shown in FIG. 2, panels (a)-(d), using substituted 4,4'-bipyridine (FIG. 2, panels (a) and (b)) and substituted fused bipyridines (FIG. 2, panels (c) and (d)) as illustrative examples. The substituents on pyridine ring carbon atoms (designated as $R_1$-$R_7$ in FIG. 2, panels (a)-(d)) can also be present on the other pyridyl reactants and pyridinium derivatives described herein. Substituents that may be present on one or more carbon atoms of one of more of the pyridine rings may be independently selected from a hydrogen atom or one the following functional groups: alkyl groups (e.g., —$CH_3$), a polyethylene glycol (PEG) (e.g., —$OCH_2CH_2$-[EG]$_n$, wherein n is an integer in the range from 1 to 5), carboxylic or carboxylate (e.g., —COOM, where M is H, $NH_4$, Na, or K), sulfonate (—$SO_3^-$), phosphonate (—$PO_3^{2-}$), or an alkyl quaternary ammonium (—$CH_3NR'''_3^+$, where $R'''_3^+$ is an alkyl group).

The derivatizing reactants include a leaving group and a derivatizing group. The leaving group is an atom or chemical group that acts as a leaving group during the reaction of the pyridyl reactant with the derivatizing reactant. The derivatizing group becomes a substituent on the nitrogen atom of a pyridine ring of the pyridyl reactant. Chlorine atoms are examples of leaving groups. However, other leaving groups can be used, as discussed below.

The derivatizing groups of the derivatizing reactants typically include an alkyl chain, alkenyl chain (i.e., a carbon-carbon chain that includes at least one carbon-carbon double bond), an alkynyl chain (i.e., a carbon-carbon chain that includes at least one carbon-carbon double bond) or alkoxy chain (i.e., a chain containing at least one ether linkage). The alkyl, alkenyl, alkynyl, and alkoxy chains may be substituted or unsubstituted and may, optionally, have a terminal functional group. Ethers, such as polyethylene glycol ethers, are examples of alkoxy groups. For applications in which high water solubility is important, the alkyl, alkenyl, alkynyl, or alkoxy chains may be short, containing, for example, 10 or fewer, including 6 or fewer, atoms in the backbone chain. Shorter chains may aid in rendering the pyridyl reactants and pyridinium derivatives made therefrom sufficiently water-soluble for a hydrothermal synthesis. However, longer chains can be used. Hydroxyl groups (—OH) are examples of a functional group that may be a substituent and/or a terminal group on an alkyl, alkenyl, alkynyl, or alkoxy chain. Thus, the derivatizing reactants include alcohols and the alcohols include diols, triols, and higher order alcohols. Other terminal functional groups that may be present on the derivatizing group of a derivatizing reactant include ammonium groups and/or sulfonate groups. The ammonium groups may be a quaternary ammonium, such as trimethyl ammonium, or a non-quaternary ammonium, such as imidazolium. However, a broad range of terminal functional groups may be present, and these can be represented by the general formulas: —$NO_2$, —OR', —$N(R')_x$, —C(O)R', —C(O)OR', —S(O)$_x$, —$PO_3$, —S(O)$_x$R', —S(O)$_x$OR', —OP(O)(OR')$_2$; —$OCH_2$, —$(CR'_2)_yCN$, substituted aryl, and substituted heteroaryl, where R is independently selected from the group consisting of hydrogen, alkyl, cycloalkyl, heterocyclyl, aryl, heteroaryl, alkyl-N(R")$_x$, alkyl-S(O)$_x$, an oxygen protecting group, and a nitrogen protecting group; R" is independently selected from the group consisting of hydrogen, alkyl, cycloalkyl, heterocyclyl, aryl, heteroaryl, an oxygen protecting group, and a nitrogen protecting group; x is independently 2 or 3; and y is independently 2 or 3.

For hydrothermal synthesis, it may be particularly advantageous to use a derivatizing reactant having a secondary alcohol on a derivatizing group. This strategy can be used to enhance the solubilities of pyridyl reactants having a non-hydroxyl terminal group, including the non-hydroxyl terminal groups listed above. By way of illustration, some embodiments of the derivatizing reactants include both a secondary alcohol group and an ammonium group or both a secondary alcohol group and a sulfonate group. In addition, as discussed in more detail below, pyridyl reactants having a secondary alcohol and a hydroxyl or non-hydroxyl terminal group can also be used to produce water-soluble, asymmetric pyridinium derivatives.

Figure 3:
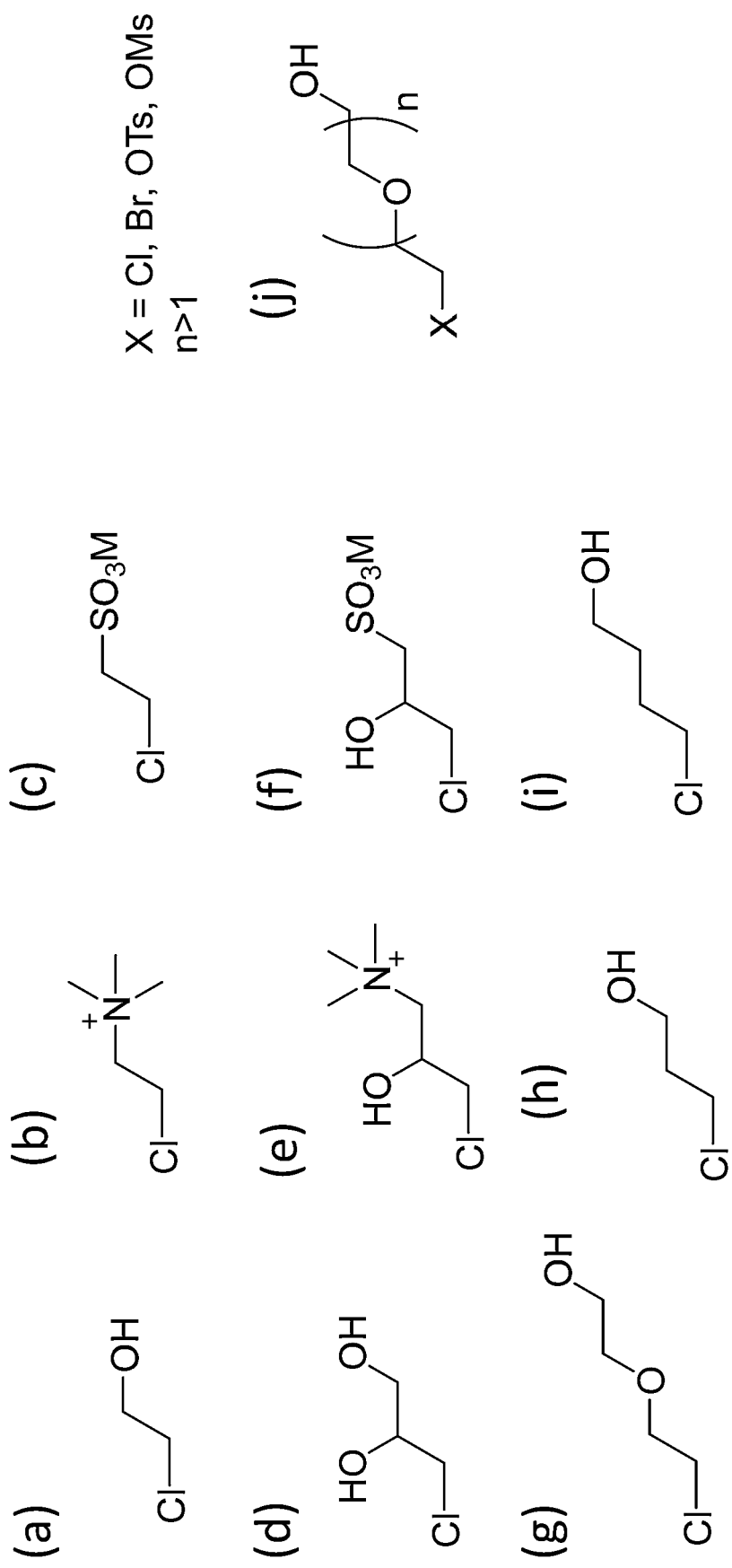
FIG. 3, panels (a)-(j), shows examples of commercially available chlorine-containing derivatizing reactants (chloro reactants): 2-chloroethanol (FIG. 3, panel (a)), (2-chloroethyl)trimethylammonium chloride (FIG. 3, panel (b)), sodium 2-chloroethanesulfonate (FIG. 3, panel (c)), 3-chloropropane-1,2-diol (FIG. 3, panel (d)), 3-chloro-2-hydroxypropyl trimethylammonium chloride (FIG. 3, panel (e)), sodium 3-chloro-2-hydroxypropanesulfonate (FIG. 3, panel (f)), 2-(2-chloroethoxy)ethanol (FIG. 3, panel (g)), 3-chloro-1-propanol (FIG. 3, panel (h)), 4-chloro-1-butanol (FIG. 3, panel (i)), and a polyethylene glycol (PEG) chain (FIG. 3, panel (j)).

Specific illustrative examples of commercially available chlorine-containing derivatizing reactants (chloro reactants) include, 2-chloroethanol (FIG. 3, panel (a)), (2-chloroethyl) trimethylammonium chloride (FIG. 3, panel (b)), sodium 2-chloroethanesulfonate (FIG. 3, panel (c)), 3-chloropropane-1,2-diol (FIG. 3, panel (d)), 3-chloro-2-hydroxypropyl trimethylammonium chloride (FIG. 3, panel (e)), sodium 3-chloro-2-hydroxypropanesulfonate (FIG. 3, panel (f)), 2-(2-chloroethoxy)ethanol (FIG. 3, panel (g)), 3-chloro-1-propanol (FIG. 3, panel (h)), 4-chloro-1-butanol (FIG. 3, panel (i)), and a polyethylene glycol (PEG) chain (FIG. 3, panel (j)). Although the reactants in FIG. 3, panels (a)-(i), are chloride molecules, the reactants need not be chloride molecules. For example, water-soluble compounds of the type shown in FIG. 3, panels (a)-(i), in which the chloride atom is replaced by a different leaving group can also be used. For purposes of illustration, the PEG chain in FIG. 3, panel (j), is shown as terminated with a generic leaving group, X. Various atoms or chemical groups that act as a leaving group during the reaction of a pyridine ring nitrogen with the derivatizing reactant may be used. Examples of X leaving groups are other halogens, such as Br or I, OTs (tosylate), and OMs (methanesulfonyl). These and other reactive terminal groups can be substituted for the Cl atoms in the other derivatizing reactants shown in FIG. 3, panels (a)-(j).

In some cases, the derivatizing reactants are salts, as in the case of the quaternary ammonium group-containing and sulfonate group-containing derivatizing reactants. These salts may have various charge-balancing ions (cations) associated therewith. Alkali metals, such as sodium, are examples of common charge-balancing counterions. However, the negatively charged salts may have counterions other than sodium, which is demonstrated in FIG. 3, panels (c) and (f), where M is used to represent a generic counterion.

The pyridinium derivatives made from the pyridyl reactants and derivatizing reactants are characterized by a pyridinium group-containing redox core with substituents on the nitrogen atoms of the pyridine rings, wherein the chemical structures of said substituents reflect the chemical structures of the derivatizing groups of the derivatizing reactants used to make them. Thus, the pyridinium derivative resulting from the reaction shown in FIG. 1A has the generic structure:

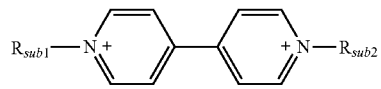

where Rsub$_1$ and Rsub$_2$ represent substituents and may be the same or different. It should be understood that pyridinium derivatives having a different redox core will have an analogous structure, as illustrated by the products in FIGS. 1B-1O. The substituents may be further represented by the generic structure -L-T, where L is a linker chain and T is the terminal group on the linker chain. The structure of the L and T for a given pyridinium derivative will depend on the derivatizing reactants used to make that derivative. Thus, the L may be a substituted or unsubstituted alkyl, alkenyl, alkynyl, or alkoxy chain and T may an ammonium, sulfonate, or hydroxyl group—or another terminal functional group, as previously defined herein. The L and T groups of the substituents on different pyridine rings of a dipyridinium derivative may be the same or different. The linker chain is typically a short chain having two to six atoms in the backbone of the chain. However, as shown in FIG. 3, panel (j), the linker chain may be longer, having—for example—10 or more or 12 or more atoms (e.g., 6 to 20 atoms). Illustrative examples of R substituents having an L-T structure include, but are not limited to, those having the following chemical structures:

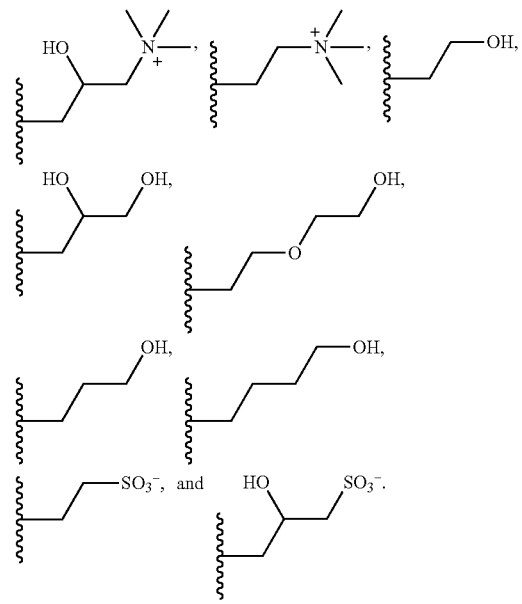

(In these structures, by convention, the attachment to the nitrogen atom of the pyridine ring is represented by a wavy line.) Respectively, these substituents are —CH$_2$CH(OH)CH$_2$N(CH$_3$)$_3$, —(CH$_2$)$_2$N(CH$_3$)$_3$, —(CH$_2$)$_2$OH, —CH$_2$CH(OH)CH$_2$OH, —(CH$_2$)$_2$O(CH$_2$)$_2$OH, —(CH$_2$)$_3$OH, —(CH$_2$)$_4$OH, (CH$_2$)$_2$SO$_3$, and —CH$_2$CH(OH)CH$_2$SO$_3$.

Figure 4A:
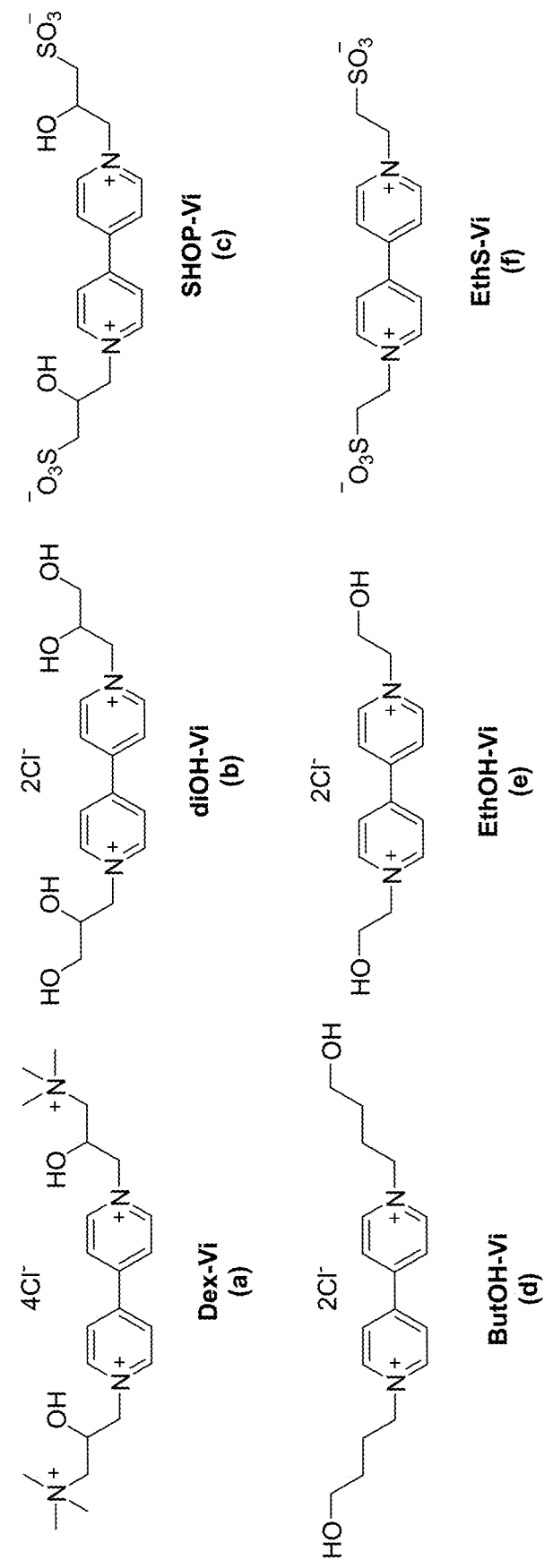
FIGS. 4A, panels (a)-(f), and 4B, panels (a)-(h), show different pyridinium derivatives.
Figure 4B:
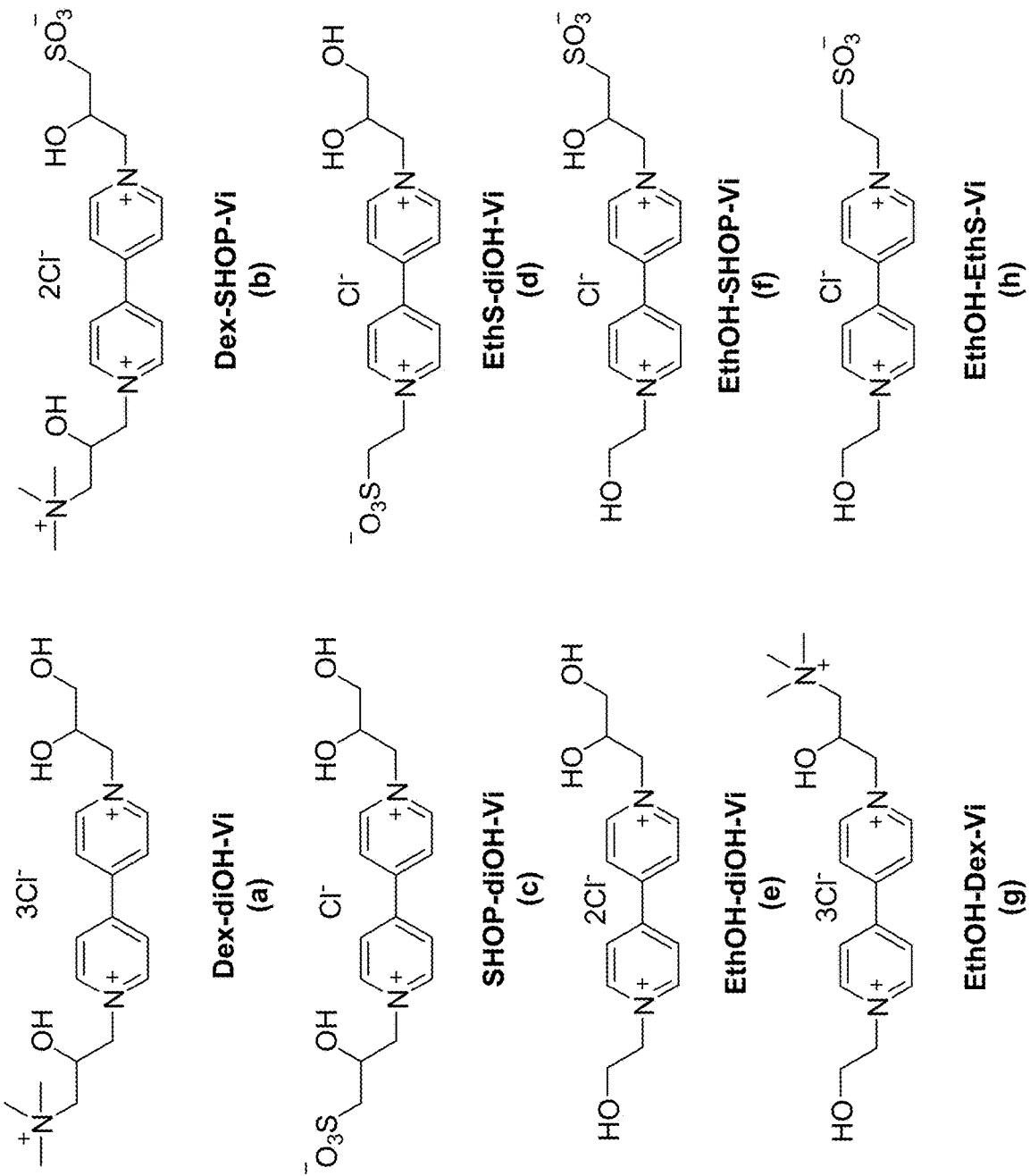
FIG. 4C, panels (a)-(d), shows the structures of some illustrative examples of pyridinium derivatives that can be made using the reaction of FIG. 1K and some of the derivatizing reactant molecules of FIG. 3, panels (a)-(j).
FIG. 4D, panels (a)-(d), shows the structures of some illustrative examples of pyridinium derivatives that can be made using the reaction of FIG. 1L and some of the derivatizing reactant molecules of FIG. 3, panels (a)-(j).
FIG. 4E, panels (a)-(d), shows the structures of some illustrative examples of pyridinium derivatives that can be made using the reaction of FIG. 1M and some of the derivatizing reactant molecules of FIG. 3, panels (a)-(j).
FIGS. 4F, panels (a)-(b), and 4G, panels (a)-(b), show the structures of some illustrative examples of pyridinium derivatives that can be made using the reaction of FIG. 1O and some of the derivatizing reactant molecules of FIG. 3, panels (a)-(j).

Depending upon the particular pyridyl reactants and derivatizing reactants used, a wide range of different pyridinium derivatives can be synthesized. FIGS. 4A, panels (a)-(f), and 4B, panels (a)-(h), show the structures of some illustrative examples of 4,4'-bipyridinium derivatives that can be made using the reaction of FIG. 1A and some of the derivatizing reactant molecules of FIG. 3, panels (a)-(j).

Figure 4D:
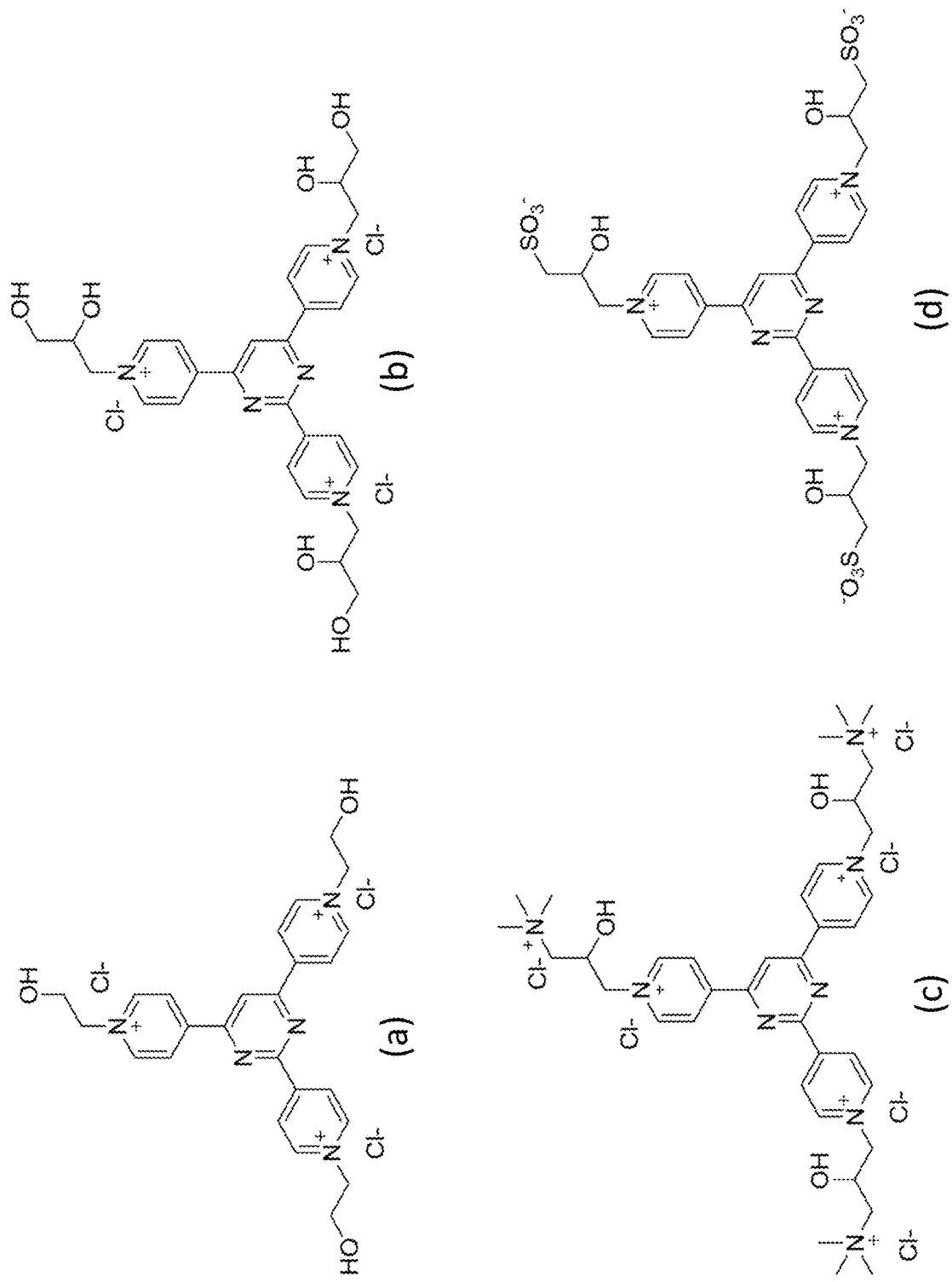
Figure 4E:
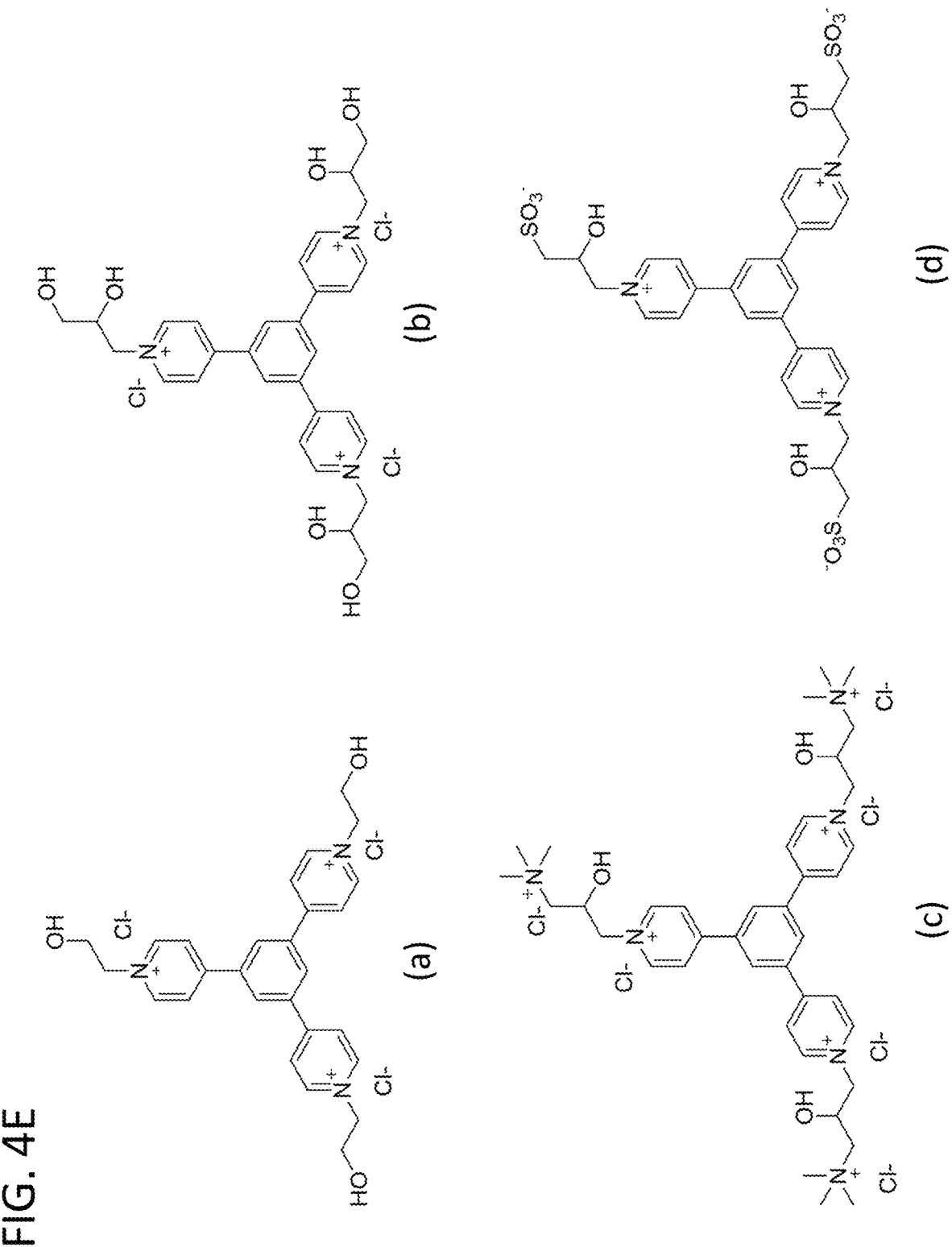
Figure 4F:
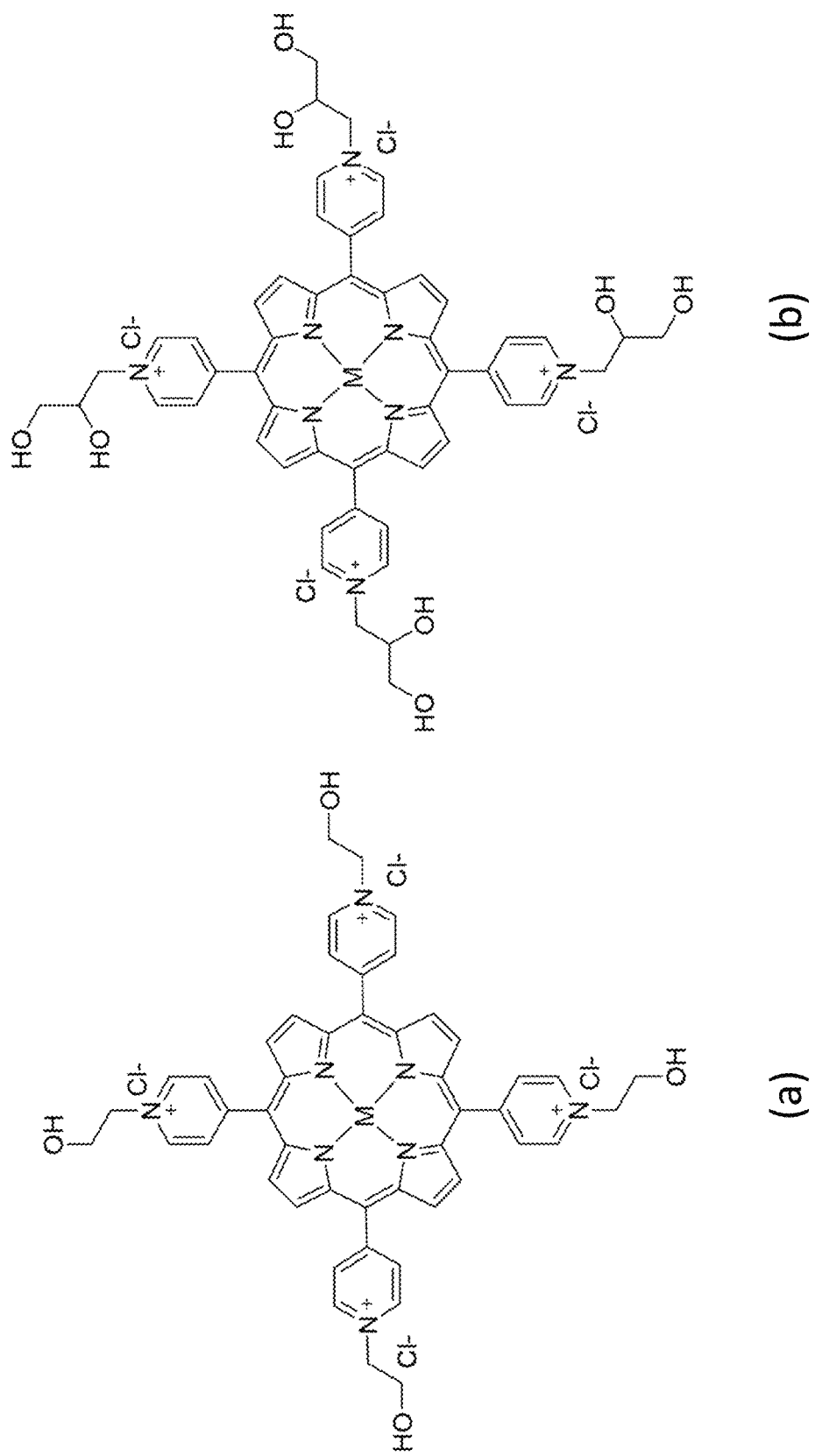
Figure 4G:
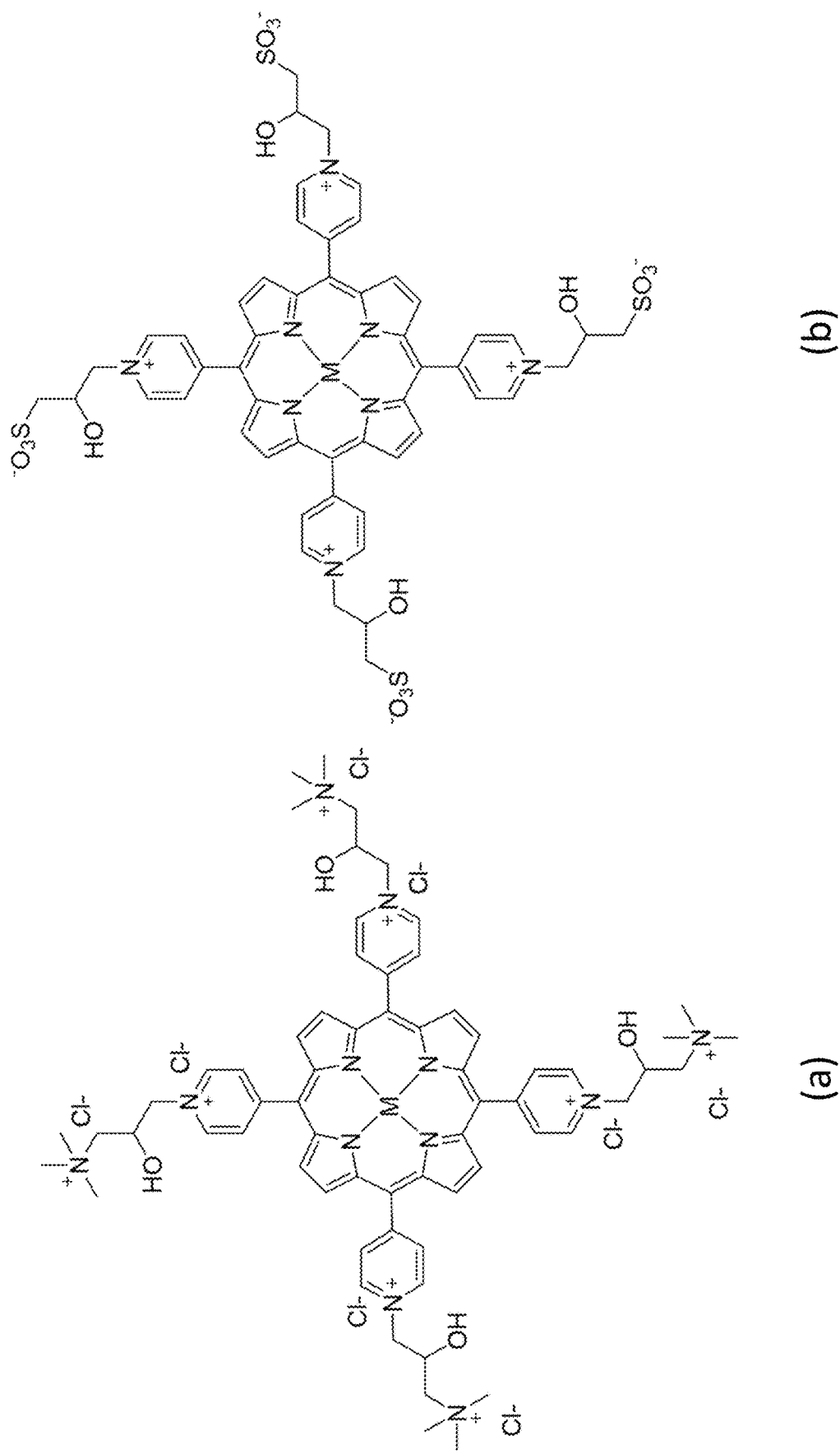
Figure 5C:
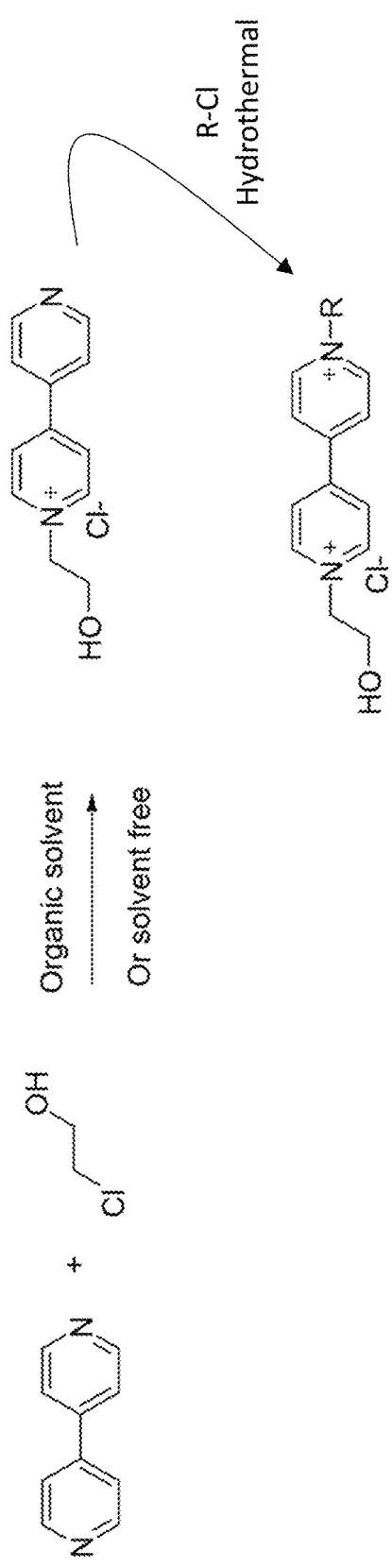
Figure 5D:
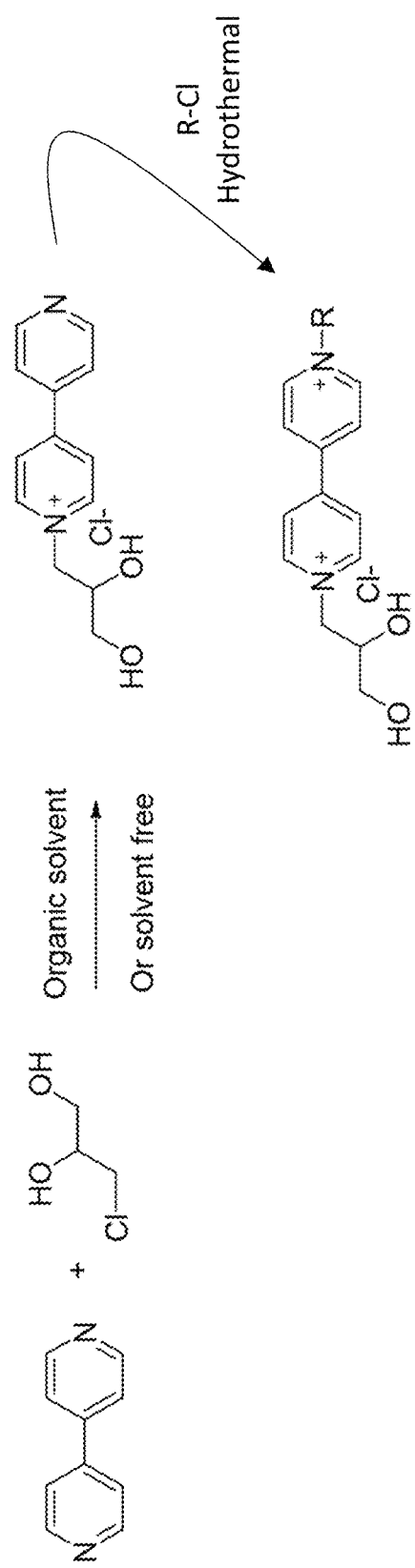

FIG. 4C, panels (a)-(d), shows the structures of some illustrative examples of pyridinium derivatives that can be made using the reaction of FIG. 1K and some of the derivatizing reactant molecules of FIG. 3, panels (a)-(j). FIG. 4D, panels (a)-(d), shows the structures of some illustrative examples of pyridinium derivatives that can be made using the reaction of FIG. 1L and some of the derivatizing reactant molecules of FIG. 3, panels (a)-(j). FIG. 4E, panels (a)-(d), shows the structures of some illustrative examples of pyridinium derivatives that can be made using the reaction of FIG. 1M and some of the derivatizing reactant molecules of FIG. 3, panels (a)-(j). FIGS. 4F, panels (a)-(b), and 4G, panels (a)-(b), show the structures of some illustrative examples of pyridinium derivatives that can be made using the reaction of FIG. 1O and some of the derivatizing reactant molecules of FIG. 3, panels (a)-(j).

The pyridinium derivatives from the hydrothermal syntheses described herein, including those shown in FIGS. 1A-1O, may be symmetric or asymmetric. In a symmetric pyridinium derivative all of the substituents (e.g., $R_{sub1}$ and $R_{sub2}$ in the example above) on the pyridinium nitrogen atoms are the same, while in an asymmetric pyridinium derivative there are at least two different pyridinium ring nitrogen atom substituents. The asymmetric tripyridinium derivatives can have two or three different $R_{sub}$ groups, while the asymmetric tetrapyridinium derivatives can have two, three, or four different $R_{sub}$ groups. Symmetric pyridinium derivatives can be made by using a single type of derivatizing reactant molecule in a single-step, one-pot hydrothermal synthesis. Asymmetric pyridinium derivatives can also be made in a single step by including two or more different types of derivatizing reactants, including two or more of the reactants of FIG. 3, panels (a)-(j), in a hydrothermal synthesis. Alternatively, the asymmetric products can be made using a multiple step (e.g., two or more step) synthesis. In the multistep synthesis, at least one step is generally carried out via hydrothermal synthesis, but some steps can be conducted using a non-hydrothermal reaction in order to tailor the structure of the pyridinium derivative and/or optimize yield. By way of illustration, a pyridinium derivative having the structure:

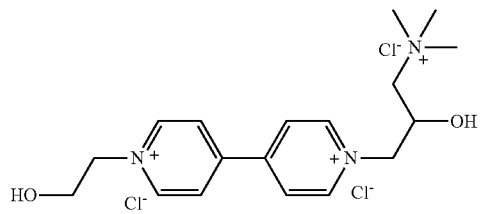

can be synthesized by including 2-chloroethanol and 3-chloro-2-hydroxypropyl trimethylammonium chloride in the aqueous reaction solution of a single-step hydrothermal synthesis, or may be synthesized in a two-step process. When a combination of symmetric pyridinium derivatives and one or more different asymmetric derivatives are produced, the different products can be, but need not be, separated post-synthesis. One example of a method for separating pyridinium derivatives from an aqueous reaction solution is the use of antisolvents, such as acetone, ethanol, methanol, DMF, or mixtures thereof to precipitate the products.

Illustrative two-step reaction schemes for pyridinium derivatives are shown in FIGS. 5A-5D. In the first step of the reaction scheme, one pyridine ring of a pyridyl reactant is reacted with a derivatizing reactant via a non-hydrothermal synthesis in an organic solution. The mono-pyridinium product from the first step is then separated from the organic solution and reacted with a derivatizing reactant in a subsequent hydrothermal synthesis in an aqueous solution. Analogous multistep reaction schemes can be conducted on pyridyl reactants that have more than two pyridyl groups, wherein the total number of reaction steps will depend on the number and types of substituents being used. While, generally, at least one step in the reaction scheme will be a hydrothermal synthesis, more than one step may be a non-hydrothermal synthesis step. Hydrothermal synthesis steps may be carried out before and/or after non-hydrothermal synthesis steps.

The ability to synthesize symmetric pyridinium derivatives, asymmetric pyridinium derivatives, and mixtures of two or more different pyridinium derivatives in a simple and efficient hydrothermal synthesis is advantageous because it allows one to tailor the derivatives and properties, such as water-solubility, viscosity, and stability, depending upon the intended application.

The pyridinium derivatives have applications in a variety of different electrochemical devices in which the pyridinium derivative acts as an anolyte in an aqueous or non-aqueous anolyte solution or anode materials in a solid state. The basic components of an electrochemical device include an anode, an anolyte in contact with the anode, a cathode, a catholyte in contact with the cathode, and an external wire or circuit connecting the anode to the cathode. When the pyridinium derivative is in a solid state, it may be coated on a surface of an anode and/or incorporated into the pores of a porous anode. When the pyridinium derivative is used in a liquid state, it is present as a solute in an anolyte solution. The basic components of an electrochemical cell that uses a liquid electrolyte include an anode cell compartment containing a pyridinium derivative as an anolyte, a cathode cell compartment containing a catholyte, and a pair of electrodes configured to apply a bias across the anode and cathode cell compartments. If the electrochemical device relies upon ion transport between a liquid anolyte solution and a liquid catholyte solution, the electrochemical cell may further include an ion-conducting membrane between the anolyte and the catholyte. The aqueous reaction solution in which the pyridinium derivatives are synthesized can be, but need not be, used neat as an anolyte solution.

Water-soluble, redox-active pyridinium derivatives that are stable in a supporting electrolyte solution, particularly a pH neutral solution (pH=7), are particularly well-suited as anolytes in AORFBs. One embodiment of an AORFB is shown schematically in FIG. 6. In the AORFB, redox-active chemical species are dissolved in an aqueous supporting electrolyte solution where they serve as anolytes and catholytes. The anolytes and catholytes may be contained in an anode cell compartment 102 and a cathode cell compartment 104. For simplicity, in FIG. 6 the pyridinium anolytes are represented generically as "B", the catholyte species are represented generically as "A", the charge on the anolyte in its oxidized and reduced states is represented by m+ and (m−y)+, respectively, and the charge on the catholyte in its oxidized and reduced states is represented by (n+x)+ and n+, respectively. An ion-conducting membrane 106 separates anode cell compartment 102 from cathode cell compartment 104. The pyridinium derivative anolytes are desirably capable of storing two or more electrons. However, pyridinium derivative anolytes that use one-electron storage can also be used.

Figure 6:
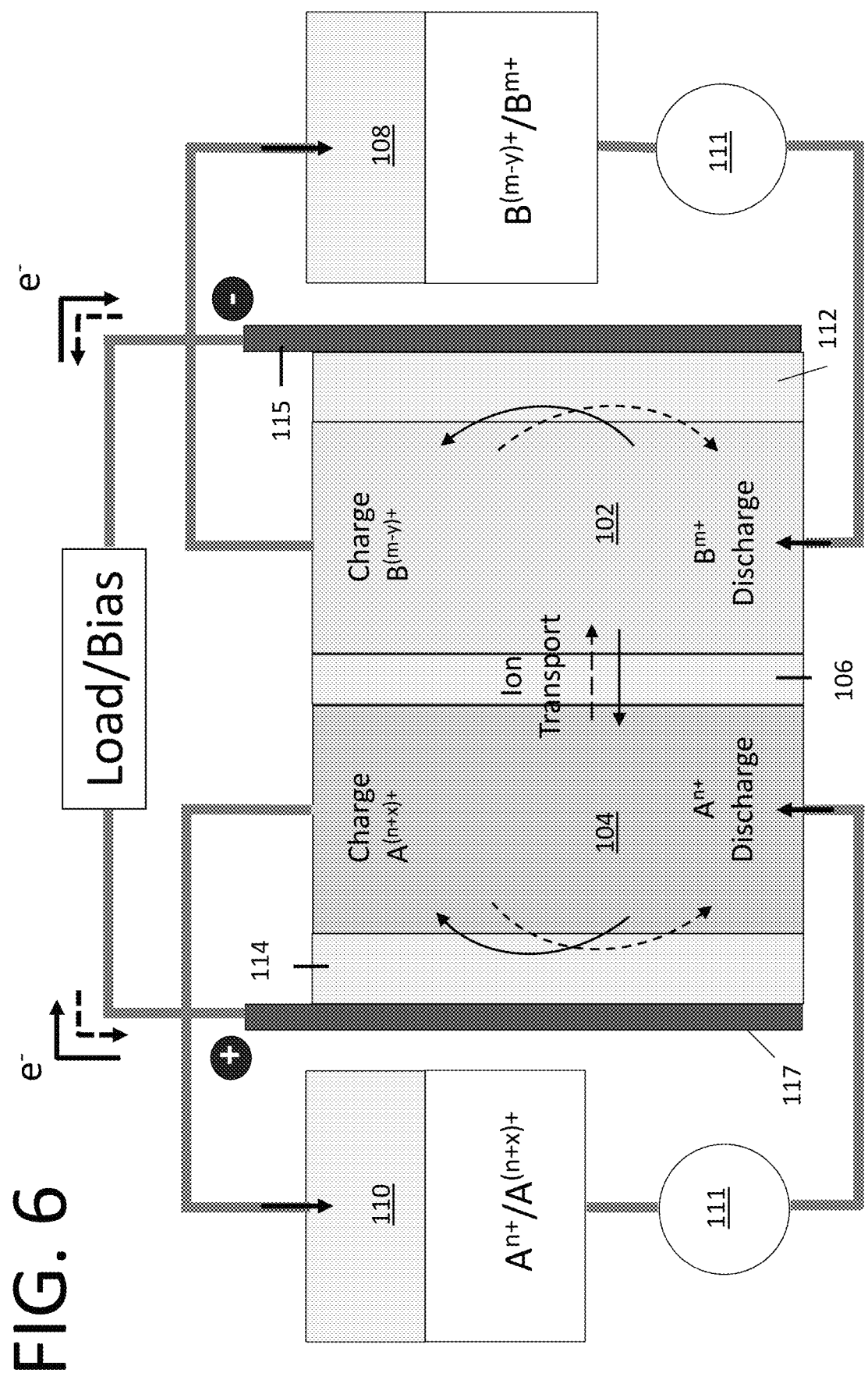
FIG. 6 is a schematic diagram of an AORFB.

During the charge-discharge process, the redox-active pyridinium derivatives (anolyte) and the catholyte are stored in an anolyte reservoir 108 and a catholyte reservoir 110. Reservoirs 108 and 110 are in fluid communication with their respective cell compartments 102 and 104, such that the anolyte and catholyte can be circulated through the cell compartments. This circulation can be accomplished using, for example, a pump 111. During the charging process, a bias is applied across an anode 112 in anode cell compartment 102 and a cathode 114 in cathode cell compartment 104. As shown in FIG. 6, an anode current collector 115 and a cathode current collector 117 can be used to provide electrical conduction between the electrodes and an external circuit. During the charging process, as the anolyte passes over anode 112, the pyridinium derivative anolyte molecules undergo electrochemical reduction reactions, while the catholyte passing over cathode 114 undergoes electrochemical oxidation reactions. During the discharge process, the pyridinium derivative anolyte molecules undergo electrochemical oxidation reactions, while the catholyte passing over cathode 114 undergoes electrochemical reduction reactions to power a load that is connected across anode 112 and cathode 114.

A variety of catholytes can be used, including those that are commonly used in known AORFBs. These include, but are not limited to, 2,2,6,6-tetramethylpiperidin-1-yl)oxyl (TEMPO), TEMPO derivatives, ferrocene, ferrocyanide, alloxazine molecules, bromide, iodide, $FeCl_2/FeCl_3$, and the like.

Optionally, the electrolyte solutions in the AORFBS, or other electrochemical cells, may include supporting electrolytes, which are chemical species (e.g., salts) that are not electroactive in the cell's range of applied potentials, but have high ionic strengths and, therefore, contribute to the conductivity of the solution. Common supporting electrolytes include NaCl, KCl, $NH_4Cl$, $Na_2SO_4$, $K_2SO_4$, $NH_4SO_4$, or mixtures thereof. However, because the pyridinium derivatives are themselves salts, the use of supporting electrolytes in the electrolyte solutions is not required. Moreover, if unreacted derivatizing reactants that are salts remain in the aqueous hydrothermal reaction solution, and that solution is used neat as an anolyte solution, the unreacted derivatizing reactants can serve as supporting electrolytes, with or without additional supporting electrolytes. Thus, the products of the hydrothermal reaction can be used directly in AORFBs without the need to separate and purify the pyridinium derivatives.

Polymeric pyridinium derivatives can also be synthesized from pyridyl reactant molecules and derivatizing reactant molecules via hydrothermal synthesis. Such polymeric pyridinium derivatives have applications as anolytes, as well as other applications. In the polymerization reactions, the pyridyl reactant molecules and derivatizing reactant molecules serve as monomers for polymer chain growth. To facilitate polymerization, the derivatizing reactant molecules will have at least two leaving groups, which may be the functional groups of the type discussed previously herein. Thus, the at least two leaving groups may be chloride atoms or other halogen atoms. By way of illustration, the polymerization of 4,4'-bipyridine and 1,2-dichloroethane is shown below:

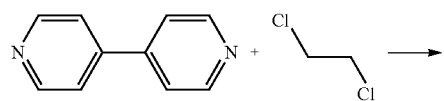

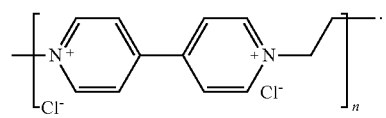

However, pyridyl reactants other than bipyridine as described herein and illustrated in FIGS. 1B-1O can also be used in the hydrothermal polymerization syntheses. Moreover, other chloroalkanes can be used as the polymerizing reactant, including other dichloro $C_1$-$C_6$ alkanes.

One dimensional, two-dimensional, and three-dimensional polymers can be synthesized by using derivatizing reactants with at least two, at least three, or a greater number of leaving groups. Examples of other derivatizing reactants include chloro-substituted triazines, such as 2,4,6-trichloro-1,3,5-triazine:

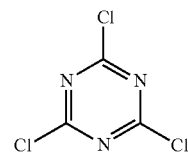

and chloro-substituted phosphazenes, such as hexachlorophosphazene:

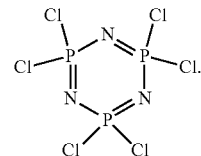 [SMILES: ClP1(Cl)=NP(Cl)(Cl)=NP(Cl)(Cl)=N1]

Summary of Certain Non-Limiting Examples of Inventions Described Herein:

Clause 1. A pyridinium derivative comprising at least two pyridinium groups, wherein the nitrogen atom of a pyridine ring of at least one of the pyridinium groups has a substituent comprising a secondary alcohol on an alkyl chain, and further wherein: the pyridinium derivative is an asymmetric pyridinium derivative; the substituent comprising the secondary alcohol has a non-hydroxyl terminal group; or the pyridinium derivative is an asymmetric pyridinium derivative and the substituent comprising the secondary alcohol has a non-hydroxyl terminal group.

Clause 2. The pyridinium derivative of clause 1, wherein the substituent comprising a secondary alcohol has a terminal group selected from: —$NO_2$, —OR', —N(R')$_x$, —C(O)R', —C(O)OR', —S(O)$_x$, —$PO_3$, —S(O)$_x$R', —S(O)$_x$OR', —OP(O)(OR')$_2$; —$OCH_2$, —(CR'$_2$)$_y$CN, substituted aryl, and substituted heteroaryl, where R is independently selected from the group consisting of hydrogen, alkyl, cycloalkyl, heterocyclyl, aryl, heteroaryl, alkyl-N(R")$_x$, alkyl-S(O)$_x$, an oxygen protecting group, and a nitrogen protecting group, provided that, if the terminal group is —OR', R' is not a hydrogen atom; R" is independently selected from the group consisting of hydrogen, alkyl, cycloalkyl, heterocyclyl, aryl, heteroaryl, an oxygen protecting group, and a nitrogen protecting group; x is independently 2 or 3; and y is independently 2 or 3.

Clause 3. The pyridinium derivative of clause 1, wherein the pyridinium derivative is a 4,4-dipyridyl having the substituent comprising the secondary alcohol on at least one pyridine ring nitrogen atom.

Clause 4. The pyridinium derivative of clause 3, wherein the substituent comprising the secondary alcohol has a terminal ammonium group.

Clause 5. The pyridinium derivative of clause 4, wherein the pyridinium derivative has the structure:

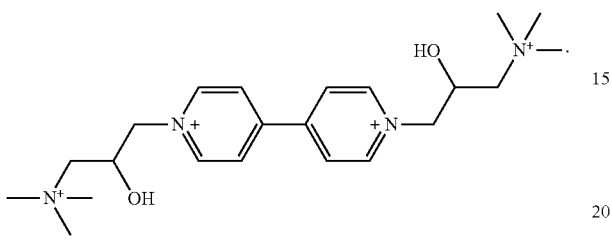

Clause 6. The pyridinium derivative of clause 3, wherein the substituent comprising the secondary alcohol has a terminal sulfonate group.

Clause 7. The pyridinium derivative of clause 6, wherein the pyridinium derivative has the structure:

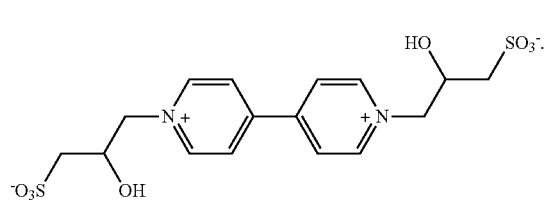

Clause 8. The pyridinium derivative of clause 1, wherein the pyridinium derivative is an asymmetric pyridinium derivative.

Clause 9. The pyridinium derivative of clause 8, wherein the asymmetric pyridinium derivative is a 4,4-dipyridyl having the substituent comprising the secondary alcohol on one pyridine ring.

Clause 10. The pyridinium derivative of clause 9, wherein the substituent comprising the secondary alcohol is a diol.

Clause 11. The pyridinium derivative of clause 10, wherein the pyridinium derivative has the structure.

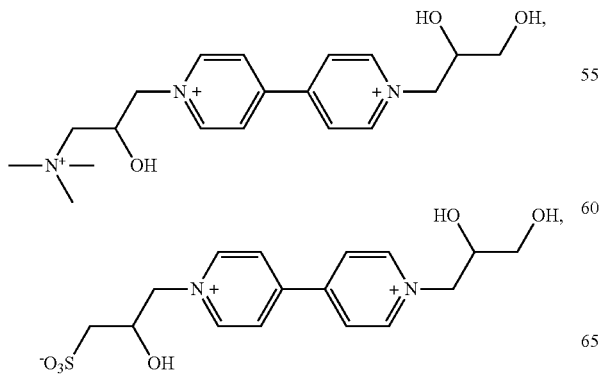

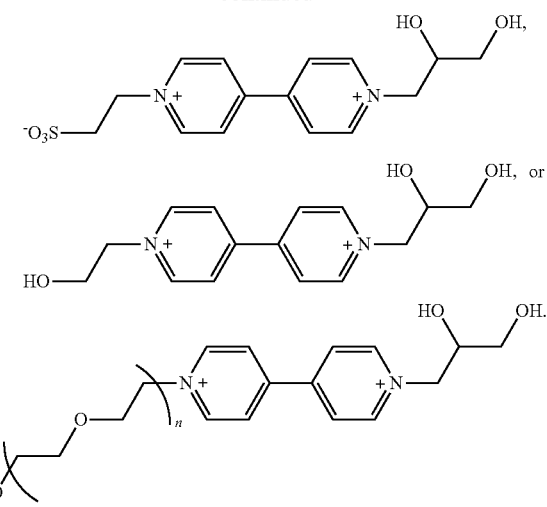

where n is an integer in the range from 1 to 5.

Clause 12. The pyridinium derivative of clause 9, wherein the substituent comprising the secondary alcohol has a terminal ammonium group or a terminal sulfonate group.

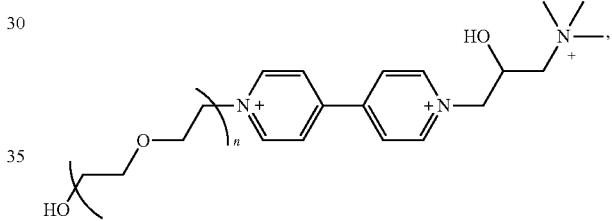

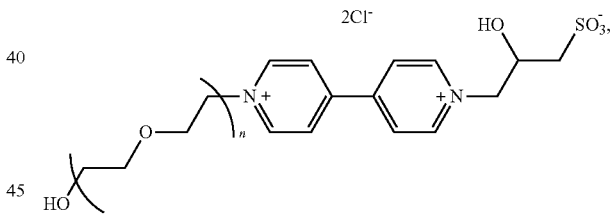

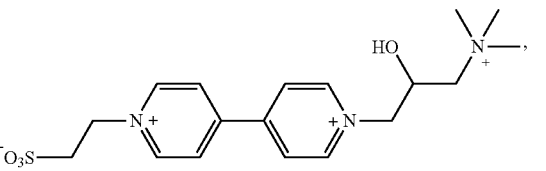

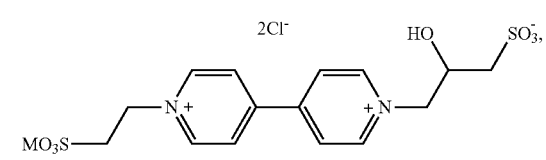

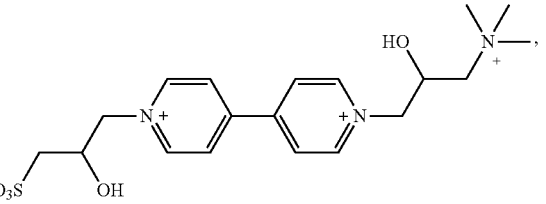

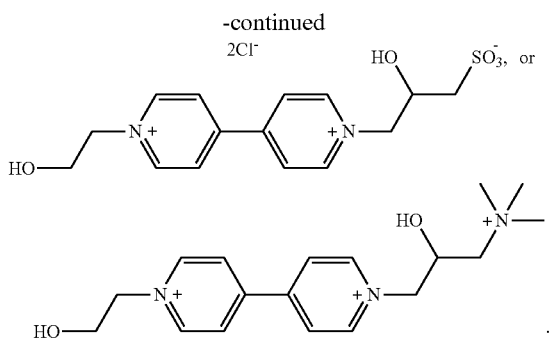

Clause 13. The pyridinium derivative of clause 12, wherein the pyridinium derivative has the structure: where n is an integer in the range from 1 to 5.

Clause 14. The pyridinium derivative of clause 1, wherein the pyridinium derivative is an extended dipyridine comprising two pyridinium groups connected by a linker, the linker comprising at least one atom, and further wherein the pyridine ring nitrogen atom of at least one of the two pyridinium groups is substituted with the substituent comprising the secondary alcohol.

Clause 15. The pyridinium derivative of clause 14, wherein the linker comprises an aliphatic chain comprising a C=C bond, a N=N bond, or a C≡C bond, an aromatic ring, a heteroaromatic ring, or two or more fused aromatic or heteroaromatic rings.

Clause 16. The pyridinium derivative of clause 1, wherein the pyridinium derivative has three pyridinium groups and the pyridinium ring nitrogen atom of at least one of the three pyridinium groups is substituted with the substituent comprising the secondary alcohol.

Clause 17. The pyridinium derivative of clause 16, wherein the pyridinium derivative is a tris(4-pyridyl)-s-triazine derivative.

Clause 18. The pyridinium derivative of clause 1, wherein the pyridinium derivative has four pyridinium groups and the pyridinium ring nitrogen atom of at least one of the four pyridinium groups is substituted with the substituent comprising the secondary alcohol.

Clause 19. The pyridinium derivative of clause 18, wherein the pyridinium derivative is a metal complexed 5,10,15,20-tetra(4-pyridyl)porphyrin derivative.

Clause 20. An electrochemical cell comprising: an anode; an anolyte in contact with the anode, the anolyte comprising the pyridinium derivative of any of clauses 1-19; a cathode; and a catholyte in contact with the cathode.

Clause 21. A method of making a pyridinium derivative using hydrothermal synthesis, the method comprising: forming an aqueous solution comprising a first reactant having two or more pyridyl groups and a second reactant comprising an organic compound having a leaving group and a derivatizing group; and reacting the first reactant with the second reactant in the aqueous solution at a temperature and a pressure, wherein the temperature is higher than the boiling point of water at the pressure, to form a compound having at least two pyridinium groups, at least one of the pyridinium groups being substituted at its pyridinium ring nitrogen atom with the derivatizing group.

Clause 22. The method of clause 21, wherein the temperature is in the range from 50° C. to 200° C.

Clause 23. The method of clause 22, wherein the pressure is in the range from 100 kPa to 1000 kPa.

Clause 24. The method of clause 21, wherein the leaving group is a chlorine atom.

Clause 25. The method of clause 21, wherein the derivatizing group comprises a functional group selected from: —NO$_2$, —OR', —N(R')$_x$, —C(O)R', —C(O)OR', —S(O)$_x$, —PO$_3$, —S(O)$_x$R', —S(O)$_x$OR', —OP(O)(OR')$_2$; —OCH$_2$, —(CR'$_2$)$_y$CN, substituted aryl, and substituted heteroaryl, where R' is independently selected from the group consisting of hydrogen, alkyl, cycloalkyl, heterocyclyl, aryl, heteroaryl, alkyl-N(R")$_x$, alkyl-S(O)$_x$, an oxygen protecting group, and a nitrogen protecting group; R" is independently selected from the group consisting of hydrogen, alkyl, cycloalkyl, heterocyclyl, aryl, heteroaryl, an oxygen protecting group, and a nitrogen protecting group; x is independently 2 or 3; and y is independently 2 or 3.

Clause 26. The method of clause 21, wherein the derivatizing group has the structure: —CH$_2$CH(OH)CH$_2$N(CH$_3$)$_3$, —(CH$_2$)$_2$N(CH$_3$)$_3$, —(CH$_2$)$_2$OH, —CH$_2$CH(OH)CH$_2$OH, —(CH$_2$)$_2$O(CH$_2$)$_2$OH, —(CH$_2$)$_3$OH, —(CH$_2$)$_4$OH, —(CH$_2$)$_2$SO$_3$, —CH$_2$CH(OH)CH$_2$SO$_3$, or —CH$_2$(CH$_2$OCH$_2$)$_n$CH$_2$OH, where n is an integer in the range from 1 to 5.

Clause 27. The method of clause 21, wherein the first reactant is a dipyridine.

Clause 28. The method of clause 27, wherein the bipyridine is a 4,4-bipyridine.

Clause 29. The method of clause 28, wherein the derivatizing group comprises a functional group selected from: —NO$_2$, —OR', —N(R')$_x$, —C(O)R', —C(O)OR', —S(O)$_x$, —PO$_3$, —S(O)$_x$R', —S(O)$_x$OR', —OP(O)(OR')$_2$; —OCH$_2$, —(CR'$_2$)$_y$CN, substituted aryl, and substituted heteroaryl, where R' is independently selected from the group consisting of hydrogen, alkyl, cycloalkyl, heterocyclyl, aryl, heteroaryl, alkyl-N(R")$_x$, alkyl-S(O)$_x$, an oxygen protecting group, and a nitrogen protecting group; R" is independently selected from the group consisting of hydrogen, alkyl, cycloalkyl, heterocyclyl, aryl, heteroaryl, an oxygen protecting group, and a nitrogen protecting group; x is independently 2 or 3; and y is independently 2 or 3.

Clause 30. The method of clause 29, wherein the derivatizing group has the structure: —CH$_2$CH(OH)CH$_2$N(CH$_3$)$_3$, —(CH$_2$)$_2$N(CH$_3$)$_3$, —(CH$_2$)$_2$OH, —CH$_2$CH(OH)CH$_2$OH, —(CH$_2$)$_2$O(CH$_2$)$_2$OH, —(CH$_2$)$_3$OH, —(CH$_2$)$_4$OH, —(CH$_2$)$_2$SO$_3$, —CH$_2$CH(OH)CH$_2$SO$_3$, or —CH$_2$(CH$_2$OCH$_2$)$_n$CH$_2$OH, where n is an integer in the range from 1 to 5.

Clause 31. The method of clause 21, wherein the first reactant is an extended dipyridine comprising two pyridyl groups connected by a linker comprising at least one atom.

Clause 32. The method of clause 31, wherein the linker comprises an aliphatic chain comprising a C=C bond, a N=N bond, or a C≡C bond, an aromatic ring, a heteroaromatic ring, or two or more fused aromatic or heteroaromatic rings.

Clause 33. The method of clause 21, wherein the first reactant has three pyridyl groups.

Clause 34. The method of clause 33, wherein the first reactant is a tris(4-pyridyl)-s-triazine.

Clause 35. The method of clause 21, wherein the first reactant has four pyridyl groups.

Clause 36. The method of clause 35, wherein the first reactant is a metal complexed 5,10,15,20-tetra(4-pyridyl)porphyrin.

Clause 37. The method of clause 21, wherein the second reactant has two or more leaving groups.

Clause 38. The method of clause 37, wherein the second reactant is a dichloroalkane, a chloro-substituted triazine, or a chloro-substituted phosphazene.

Clause 39. A pyridinium derivative comprising at least two pyridinium groups, wherein the nitrogen atom of the pyridinium ring of at least one of the pyridinium groups is substituted with a substituent comprising a hydroxyl group, a quaternary ammonium group, a sulfonate group, or a combination thereof, the pyridinium derivative being one of the following: (a) an extended dipyridinium derivative comprising two pyridinium groups connected by a linker, the linker comprising an aliphatic chain comprising a C=C bond, a N=N bond, or a C≡C bond; (b) a tris(4-pyridyl)-s-triazine derivative; and (c) a metal complexed 5,10,15,20-tetra(4-pyridyl)porphyrin derivative.

EXAMPLES

Figure 7:
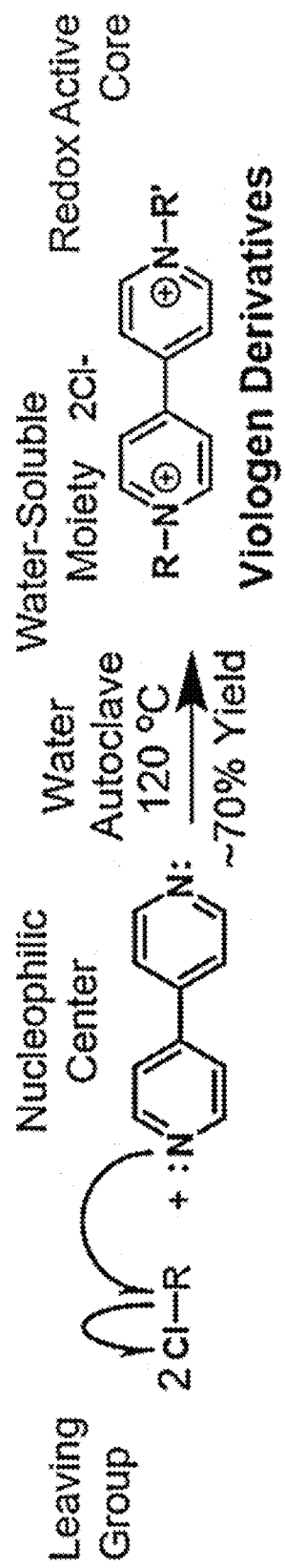
FIG. 7 shows a reaction scheme for the hydrothermal synthesis of a bipyridyl reactant and a generic chloro-derivatizing reactant.

Example 1: This example illustrates the hydrothermal synthesis of the pyridinium derivative bis(3-trimethylammonio-2-hydroxy)propyl viologen tetrachloride (Dex-Vi), from 3-chloro-2-hydroxypropyl trimethylammonium chloride (commonly known as Dextrosil). This example further illustrates the formulation of an anolyte solution using Dex-Vi and the operation of an AORFB that utilizes the anolyte. A reaction scheme for the hydrothermal synthesis of a bipyridyl reactant and a generic chloro-derivatizing reactant is shown in FIG. 7, with illustrative reaction conditions.

Although this example is directed to the specific pyridinium derivative Dex-Vi, the same or similar synthesis conditions and the various reactants described herein, including those shown in FIG. 3, panels (a)-(j), can be used to make other pyridinium derivatives, including the specific pyridinium derivatives shown in FIGS. 1A-1O, and to formulate and utilize those other pyridinium derivatives as anolytes in an electrochemical cell. This is further elaborated in Example 2. The same or similar synthesis conditions can also be used to make polymeric pyridinium derivatives from the pyridyl reactants and the reactants having two or more reactive chlorine atoms, such as chloroalkanes, chloro-substituted triazines, or chloro-substituted phosphazenes.

The hydrothermal synthesis methods overcome significant disadvantages of methods that are currently used to synthesize viologens. Viologens are typically synthesized by alkylation of pyridine species in organic solvents. (Beh, E. S. et al., 2017; DeBruler, C. et al., 2017; Liu, Y. et al., 2019; Hu, B. et al., 2018; and Liu, Y. et al., 2020.) Upon formation of the pyridinium containing species, the products always carry more charge than the starting materials, forming precipitates in the organic solutions for facile separation and purification. However, such synthetic routes become less efficient for producing the desired chloride containing viologens due to two major reasons. Firstly, the low activity of chloro-species often causes low yields for the $S_N2$ reaction, as chlorine is the least facile leaving group of the halogens. Secondly, chloride containing salts exhibit very poor solubility in organic solvents even at high temperature, which is problematic for the synthesis of bis-substituted viologen species as the asymmetric, mono-substituted bipyridine will precipitate out before the second pyridyl site reacts. The issue of forming mono-substituted byproduct becomes even more significant when the reactants already carry charge, which is often the case to achieve higher solubility in water for AORFBs (i.e., trimethylammonium or sulfate groups). Therefore, the previously reported procedures are often complex and obtain poor yields, intrinsically hindering the reduction of material cost even if large scale synthesis can be applied.

As an alternative synthetic route towards highly charged viologens, Dextrosil was identified by the inventors as an alternative starting material. Dextrosil is an inexpensive and widely available chemical that is used in various industrial processes, such as starch treatment, paper and textile manufacturing, and surfactant development. The chloro-reacting site in Dextrosil can react with the pyridyl site on 4,4'-bipyridine to yield the desired viologen product with a quaternary ammonium group that can effectively increase the product solubility in aqueous medium. The substitution reaction between Dextrosil and 4,4'-bipyridine forms the Dex-Vi product, which has two hydroxyl groups which can improve its water affinity. However, using Dextrosil as a reactant in organic solvent is not feasible: it is fairly insoluble in organic solvents and the mono-substituted bipyridine intermediate will immediately crash out of solution, preventing complete reaction. Therefore, water was used as the solvent to resolve the solubility issue as the starting materials, the intermediate, and the product are all highly aqueous soluble. Furthermore, to compensate for the low reactivity of chloro-species, Dextrosil, for $S_N2$ reaction, the reaction temperature was elevated to above the boiling point of water in autoclave reactors using a standard, simple hydrothermal reaction procedure.

Figure 8A:
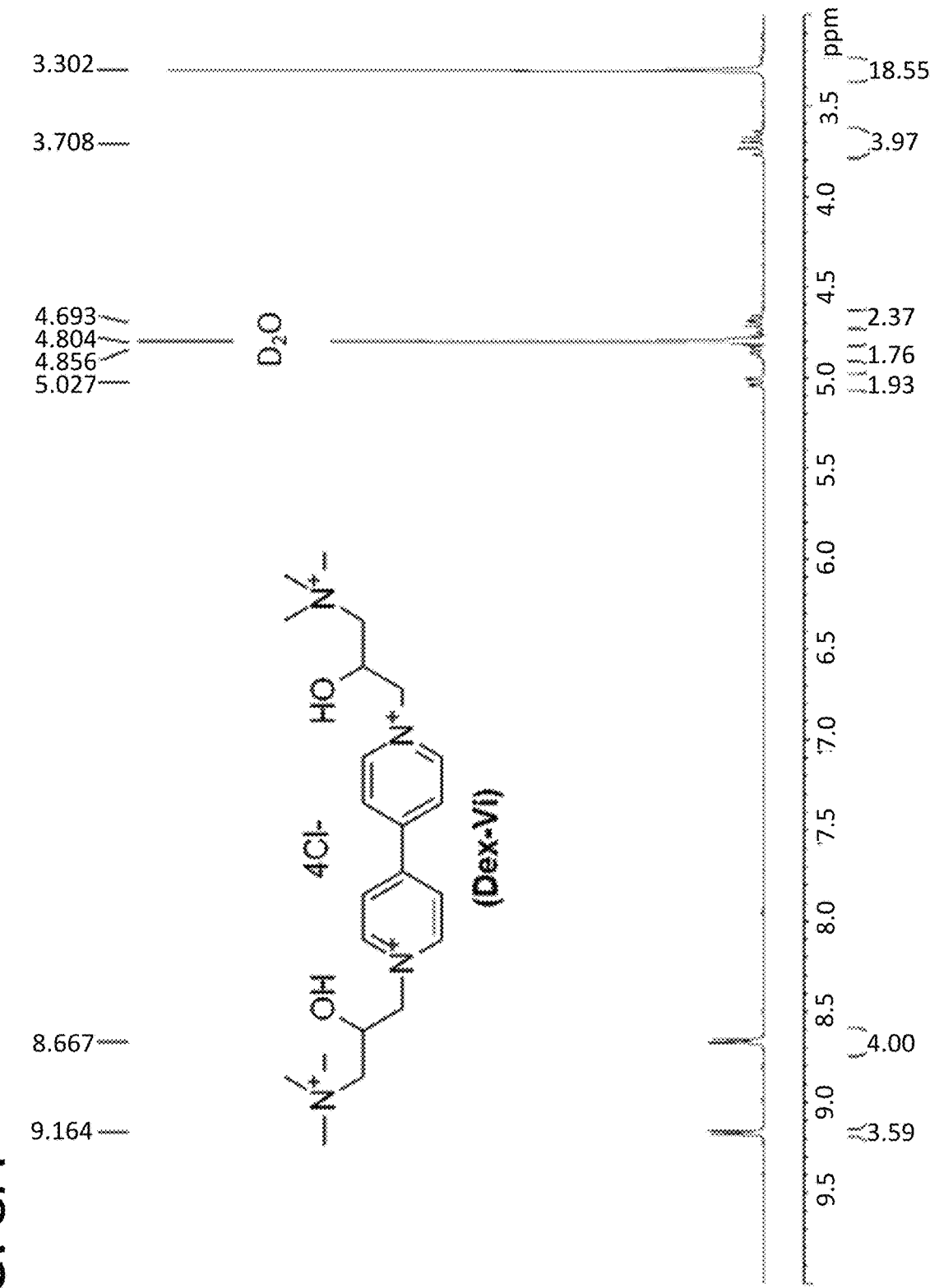
FIG. 8A shows an NMR spectrum of a pure Dex-Vi product.
Figure 8B:
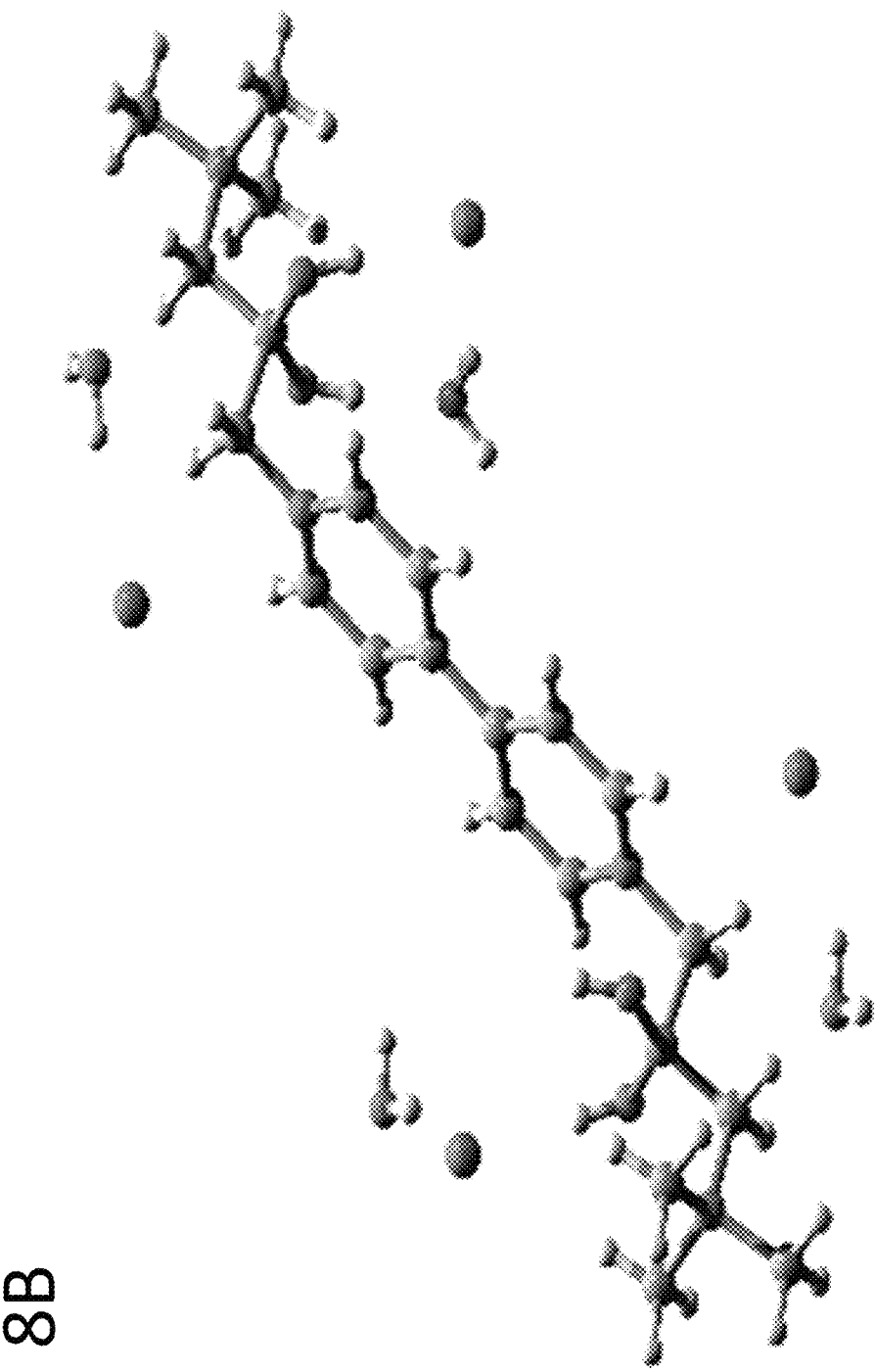
FIG. 8B shows the structure of Dex-Vi based on X-ray structural analysis.
Figure 9A:
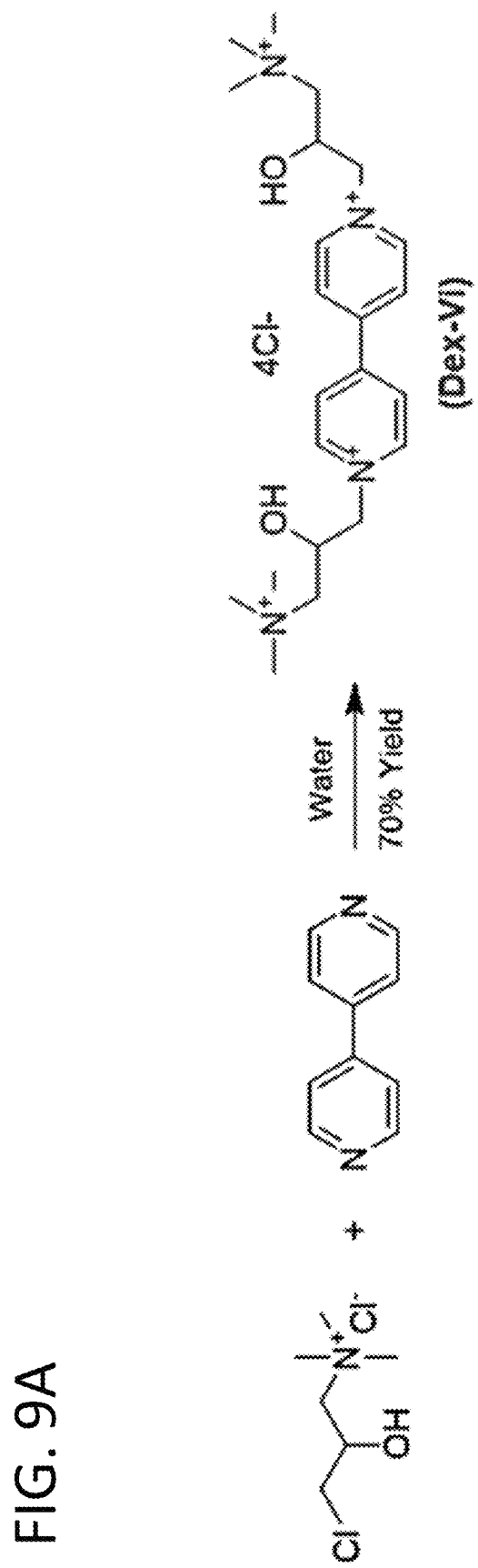
FIG. 9A shows a single-step reaction for the synthesis of Dex-Vi.
Figure 9B:
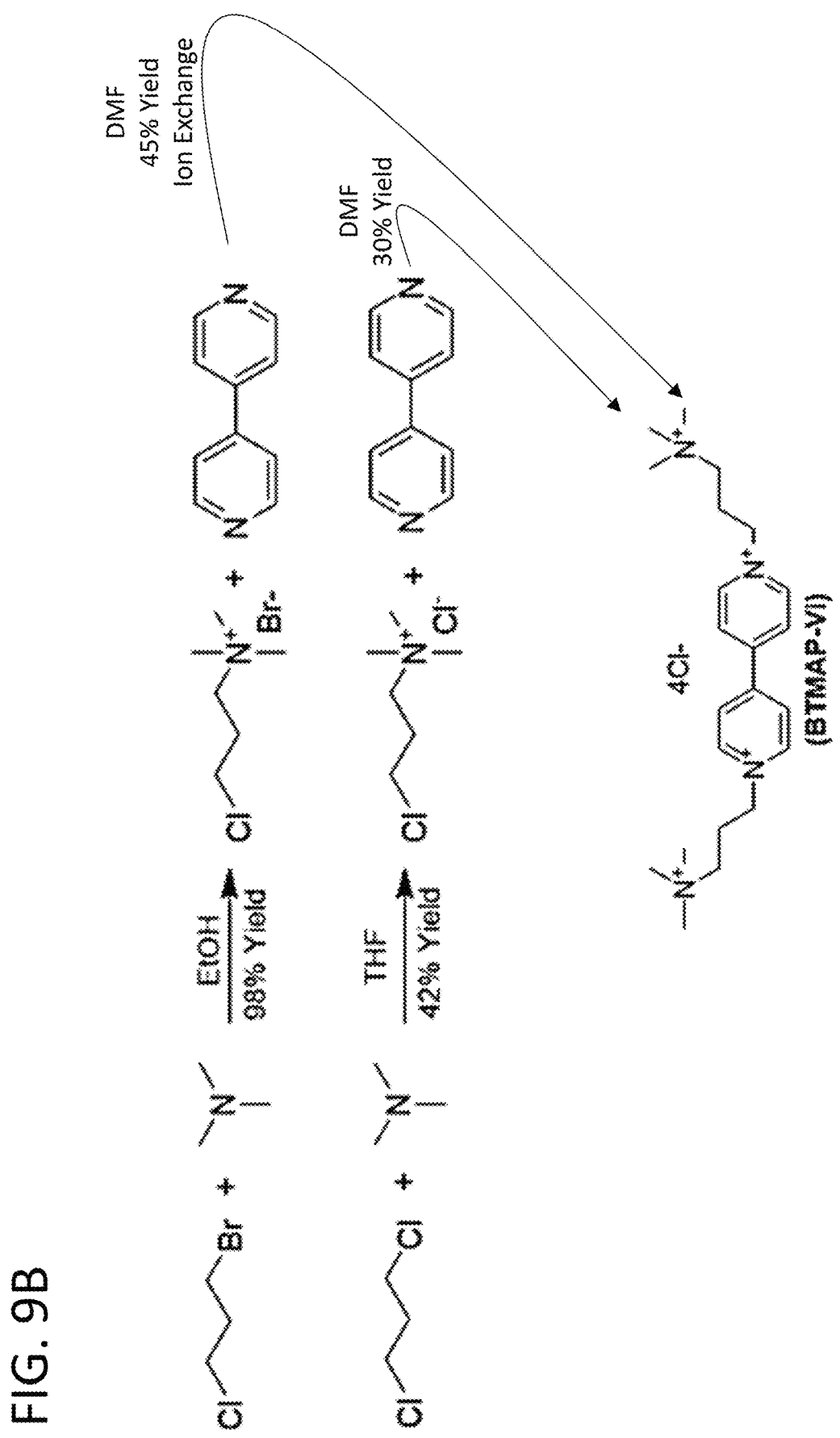
FIG. 9B shows the synthesis of BTMAP-Vi, as described in Beh, E. S. et al., 2017; DeBruler, C. et al., 2017; Liu, Y. et al., 2019; Hu, B. et al., 2018; and Liu, Y. et al., 2020.
Figure 10B:
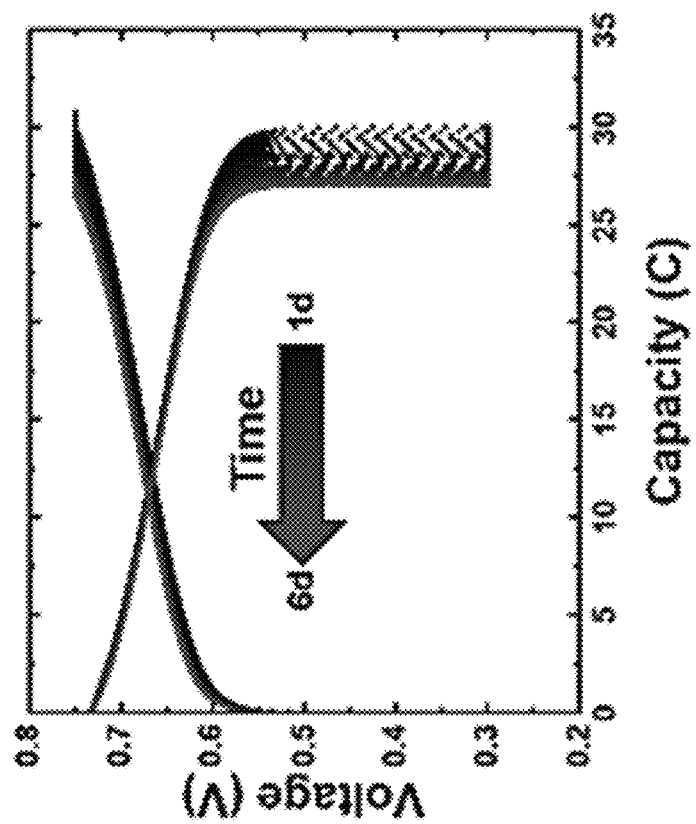
FIGS. 10A and 10B demonstrate that Dex-Vi can be synthesized "neatly," and the product can be used directly in AORFB flow cells without purification.
Figure 10A:
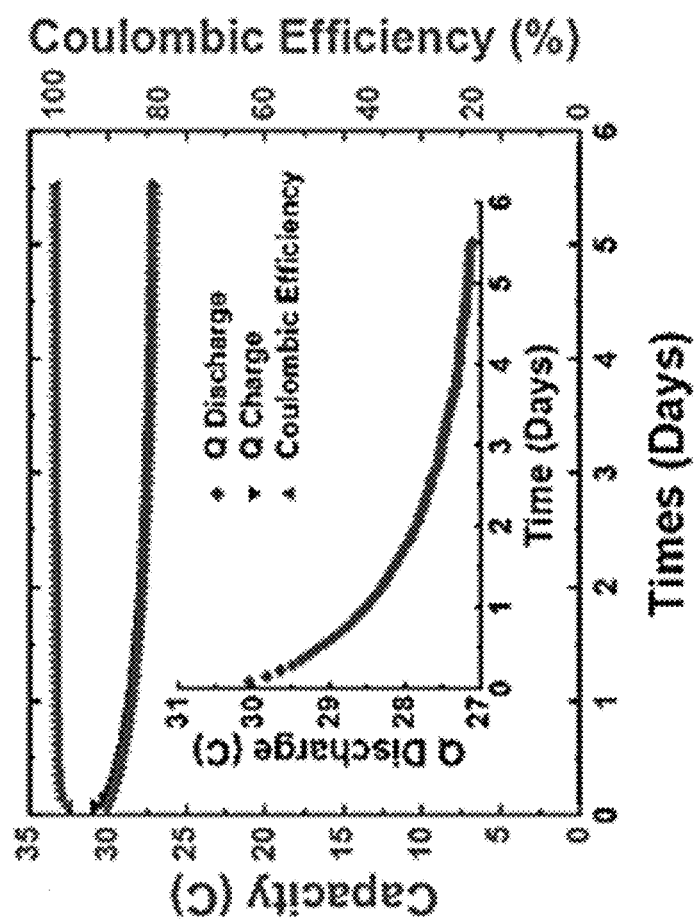

As confirmed through NMR (FIG. 8A) and X-ray structural analysis (FIG. 8B), the pure Dex-Vi product was successfully obtained through the hydrothermal reaction. Single crystal data shows the coordination of four water molecules and four chlorides to the product, resulting in a molecular weight of 604 g·mol$^{-1}$ ($C_{22}H_{38}O_2N_2Cl_4·4H_2O$). This pure product was obtained in high yield of 71% in small-batch (~33 g) and 70% yield in large-batch (>600 g of product) synthesis. This high yield reflects the simplicity of the single-step reaction (FIG. 9A). Additionally, the reaction itself is organic solvent-free, and the product purification requires only cheap organic solvents (i.e., ethanol and acetone). In fact, the reaction can be performed "neatly," and the product can be used directly in AORFB flow cells without purification (FIGS. 10A and 10B). This is due to the only significant impurity being the Dextrosil salt, which is unreactive at room temperature and can act as a supporting electrolyte to alleviate the requirement for additional supporting salt. This is remarkable considering the synthesis of BTMAP-Vi requires expensive starting materials and solvents in large excess with multiple reaction and purification steps (FIG. 9B). (Beh, E. S. et al., 2017; DeBruler, C. et al., 2017; Liu, Y. et al., 2019; Hu, B. et al., 2018; and Liu, Y. et al., 2020.)

Figure 11:
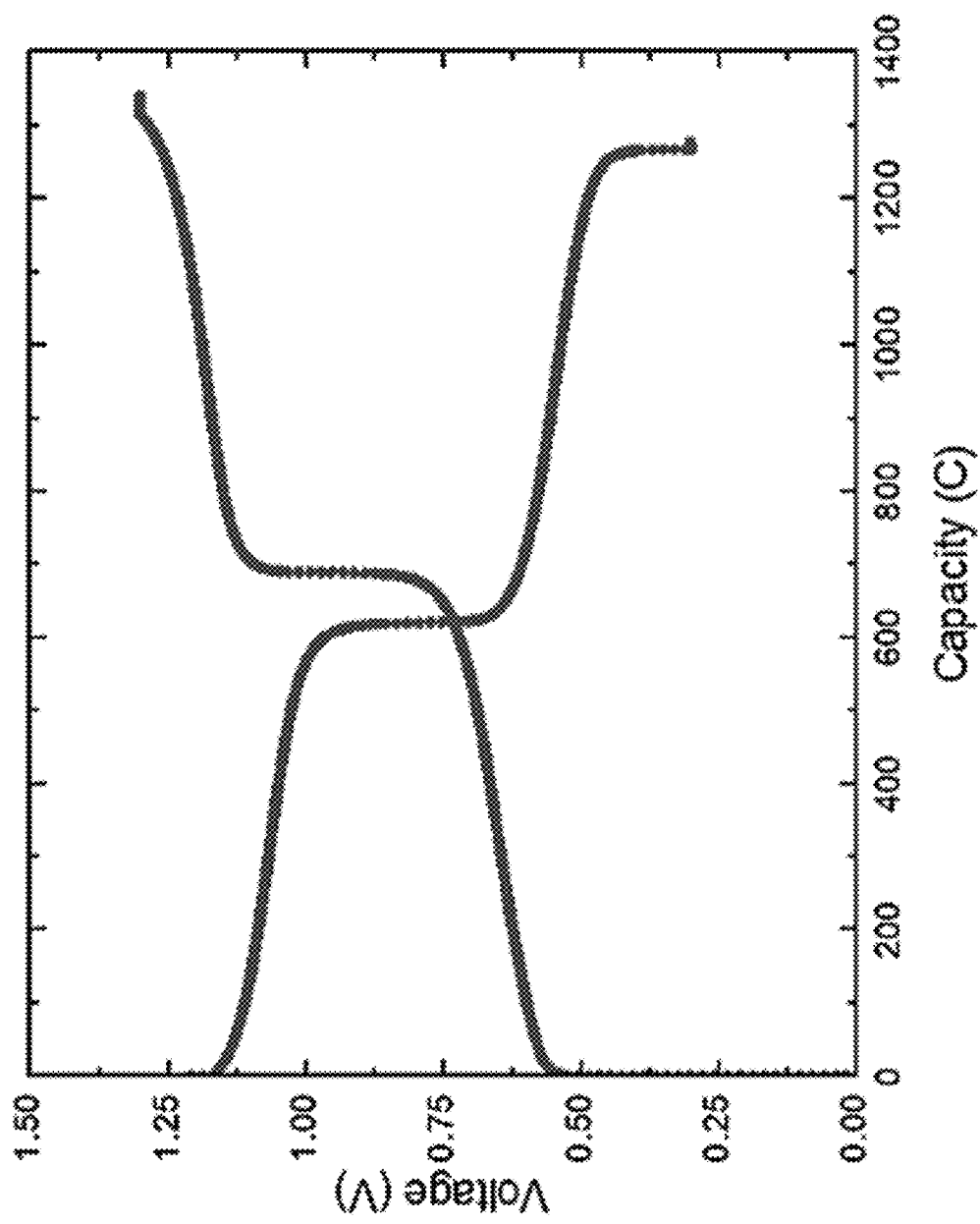
FIG. 11 is a voltage versus capacity graph demonstrating the flowability and solubility of the doubly reduced state of Dex-Vi in high concentration of 1.5 M in a full redox flow battery.

The solubility of a redox species ultimately determines the volumetric capacity of the flow battery. A maximum solubility of near 2 M was obtained for Dex-Vi in pure water at room temperature (~18° C.). Without intending to be bound to any theory of the invention, the inventors propose that the solubility of the singly (1 e⁻) and doubly reduced (2 e⁻) states of Dex-Vi that have decreased positive charge density will benefit from the presence of these hydroxyl moieties by providing them with enhanced solubilities. Pure isolation of these oxygen-sensitive reduced viologen products is challenging and thus not attempted. However, this hypothesis was partially confirmed through successfully demonstrating the flowability and solubility of the doubly reduced state of Dex-Vi in high concentration of 1.5 M in a full redox flow battery (FIG. 11). In comparison, BTMAP-Vi has only been reported in a concentration of 0.25 M when both electrons are utilized. (DeBruler, C. et al., 2017.)

The viscosity of the solution is another consideration for practical applications to optimize electrochemical charge transfer resistance and pumping cost. Viscosity data informs at which anolyte concentration the solution will flow and the cell resistance will begin to sharply increase. Accordingly, the viscosity of Dex-Vi in pure water was measured to be 1.1 cP at 0.25 M, 1.8 cP at 0.50 M, 4.7 cP at 1.0 M, and 50 cP at 1.5 M. The viscosity of viologens does not appear to be the limiting factor to the useable concentration. Instead, the solubility of the molecule, particularly in its singly and doubly reduced states, dictates the highest cycling concentration achievable without the formation of precipitates.

Figure 12A:
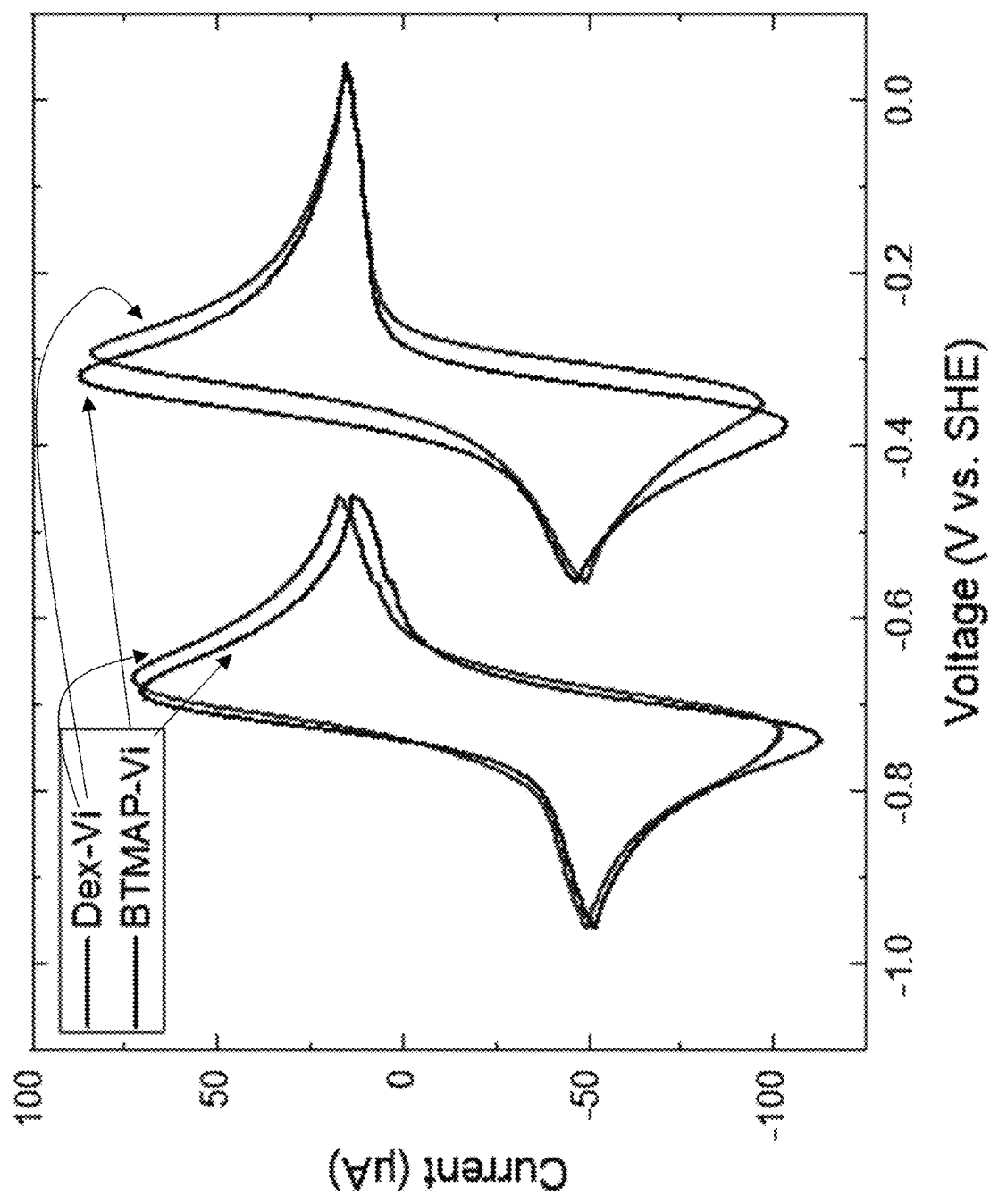
FIGS. 12A-12D show fundamental electrochemical properties of Dex-Vi, as explored through a series of voltammetry and impedance measurements: Dex-Vi possesses a first electron formal potential ($E_1^0$) of −0.322 V vs. SHE and a second electron formal potential ($E_2^0$) of −0.699 V, which are slightly more positive than those of BTMAP-Vi of −0.349 V and −0.713 V (FIG. 12A); the kinetics of the redox species investigated through cyclic voltammetry (CV) with different scan rates (FIGS. 12B-12C); and electrochemical impedance spectroscopy (EIS) (FIG. 12D).
Figure 12B:
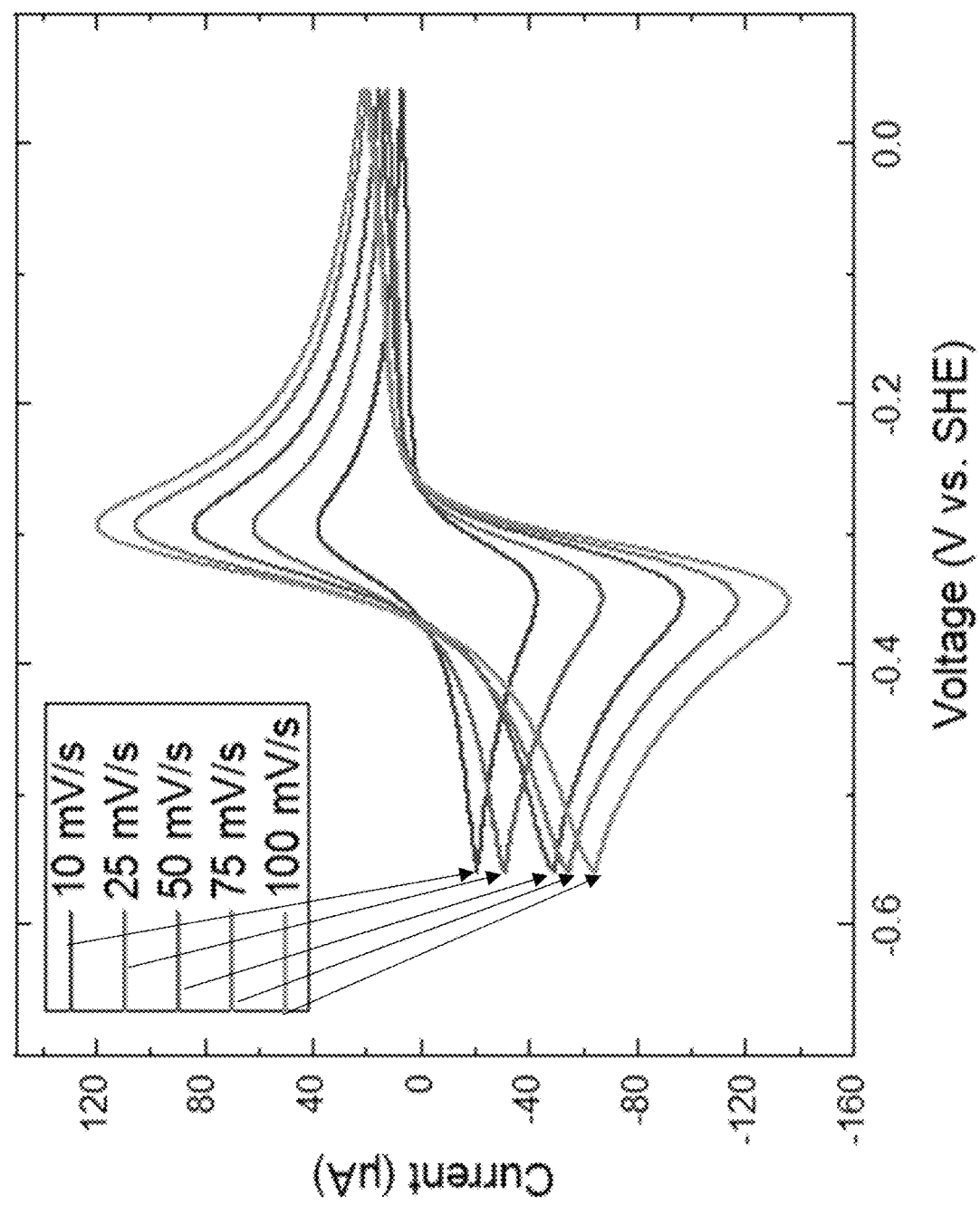
Figure 12C:
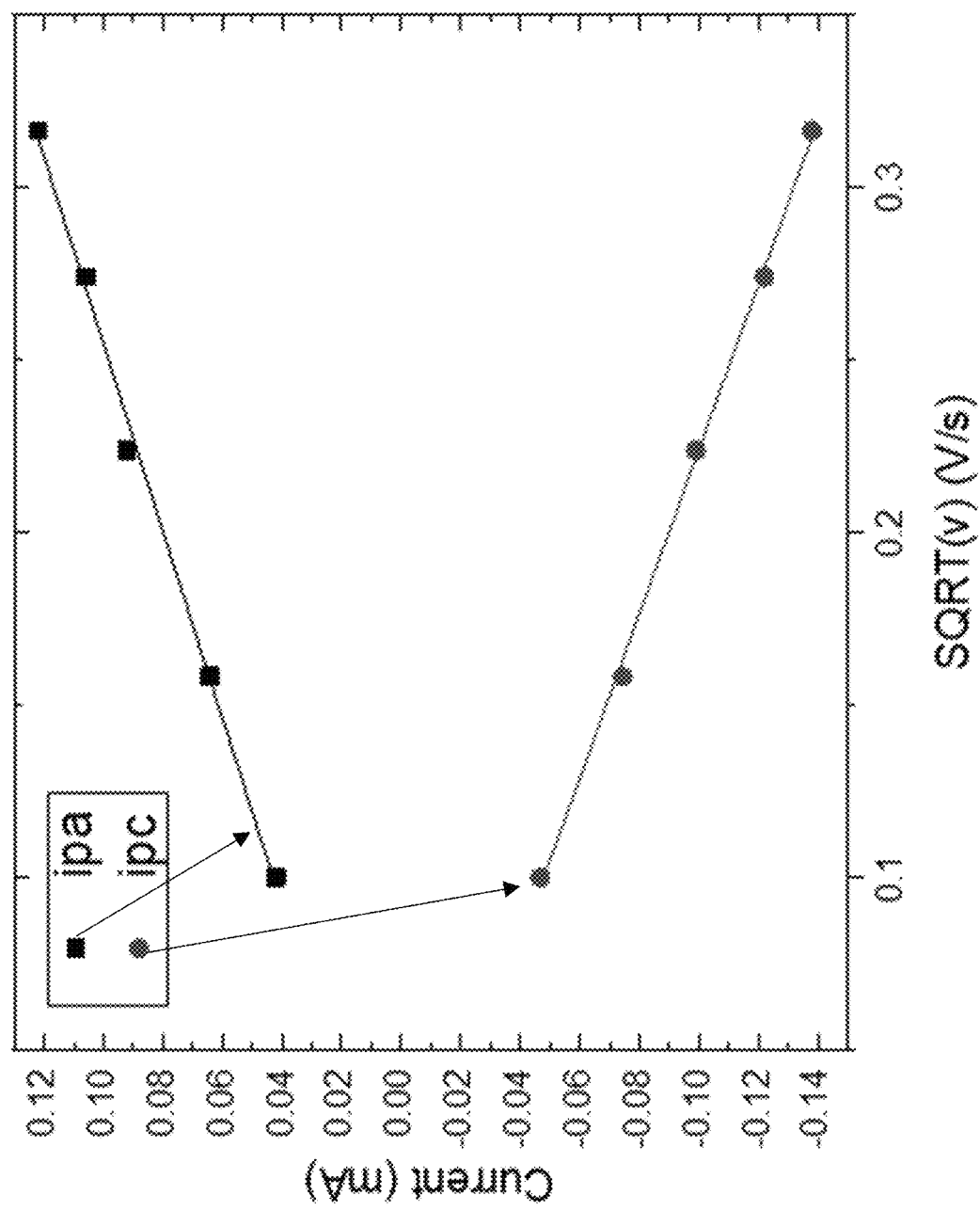
Figure 12D:
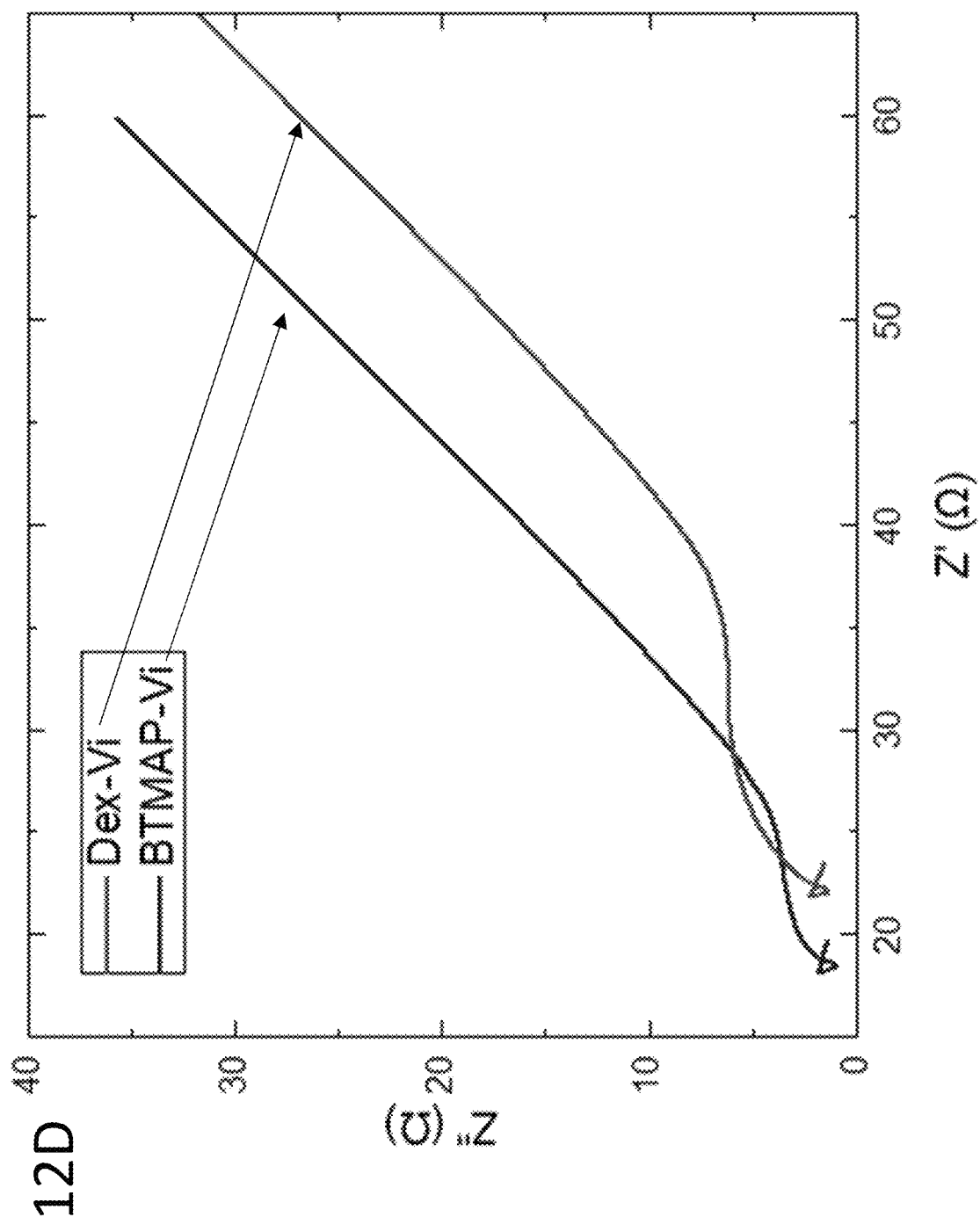

In addition to the advantageous physical properties of Dex-Vi as compared with BTMAP-Vi, it is important to elucidate whether the additional hydroxyl moieties introduce noteworthy electrochemical perturbations to the redox behavior. Thus, the fundamental electrochemical properties of Dex-Vi were explored through a series of voltammetry and impedance measurements. Dex-Vi possesses a first electron formal potential ($E_1^0$) of −0.322 V vs. SHE and a second electron formal potential ($E_2^0$) of −0.699 V, which are slightly more positive than those of BTMAP-Vi of −0.349 V and −0.713 V (FIG. 12A). The addition of hydroxyl groups has minimal effect on the redox potential as they are not directly involved in electron conjugation and only have slight electrostatic and entropic contributions to the redox energetics. In addition to the thermodynamics, the kinetics of the redox species were investigated through cyclic voltammetry (CV) with different scan rates (FIGS. 12B-12C) and electrochemical impedance spectroscopy (EIS) (FIG. 12D). A reduced state diffusion coefficient ($D_1^R$) of $1.9 \times 10^{-6}$ cm$^2$·s$^{-1}$ for [Dex-Vi]$^{3+}$ and an oxidized state diffusion coefficient ($D_1^O$) $2.3 \times 10^{-6}$ cm$^2$·s$^{-1}$ for [Dex-Vi]$^{4+}$ were determined at the first redox state. This is comparable to the $D_1^R$ and $D_1^O$ values of $2.7 \times 10^{-6}$ cm$^2$·s$^{-1}$ and $2.4 \times 10^{-6}$ cm$^2$·s$^{-1}$ for [BTMAP-Vi]$^{3+}$ and [BTMAP-Vi]$^{4+}$, respectively. EIS data showed combined diffusion coefficients ($D_1^{EIS}$) of $3.9 \times 10^{-6}$ cm$^2$·s$^{-1}$ and $4.1 \times 10^{-6}$ cm$^2$·s$^{-1}$ and standard rate constants ($k_1^0$) of $5.0 \times 10^{-2}$ cm·s$^{-1}$ and $8.9 \times 10^{-2}$ cm·s$^{-1}$ for the first reductions of Dex-Vi and BTMAP-Vi, respectively. The second electron diffusion coefficients ($D_2^R$, $D_2^O$, and $D_2^{EIS}$) and rate constants ($k_2^0$) of Dex-Vi and BTMAP-Vi were also of the same order of magnitude. The facile electrochemical kinetics of Dex-Vi evidenced that the hydroxyl groups impose no significant diffusional or electron kinetic barriers that may increase the electrochemical resistance and diminish power output of the flow cell through overpotential losses.

Permeability measurements reveal Dex-Vi is highly compatible with anion-exchange membranes with a permeance of $2.3 \times 10^{-11}$ cm$^2$·s$^{-1}$ through a Selemion DSV membrane, which is an order of magnitude lower than the reported value of $6.7 \times 10^{-10}$ cm$^2$·s$^{-1}$ for BTMAP-Vi (FIG. 13A). There are two plausible reasons for this improved membrane exclusion. Firstly, Dex-Vi has an increased molecular size due to the presence of the hydroxy groups, slowing its diffusion through the membrane pores. Secondly, the hydroxy groups increase the water affinity of Dex-Vi, enlarging its Stokes radius, which lowers ion mobility, increases its desolvation energy, and inhibits entry into micro-pores. Thus, Dex-Vi should exhibit minimal crossover during RFB cycling.

In addition to the electrochemical kinetics and solution diffusional behavior, it is important to examine the lifetime of the organic redox species, which currently hinders the commercialization of AORFBs. The chemical stability of the first redox processes of Dex-Vi was investigated using a symmetric, volumetrically-unbalanced flow cell inside an $N_2$ glovebox. Dex-Vi exhibited no decay in a symmetric flow cell configuration over sixteen days (150 cycles) of continuous charge-discharge cycling (FIG. 13C), which is slightly better than the reported minimal symmetric cell decay rate of BTMAP-Vi of 0.0016% per day under the same electrolyte conditions. The improved symmetric cell stability of Dex-Vi may be due to its higher basicity tolerance, which may be of concern when imperfect oxygen exclusion inside the glovebox results in oxygen reduction at the anode and HER at the negative electrode. This theory was partially supported through degradation kinetics experiments of Dex-Vi and BTMAP-Vi in sodium hydroxide. Dex-Vi was found to degrade in base in a first order mechanism with respect to Dex-Vi concentration and one-half order with respect to hydroxide concentration, resulting in a degradation rate constant k of $2.3 \times 10^{-6}$ s$^{-1}$·M$^{-1/2}$ for the overall one-and-one-half order reaction. Surprisingly, BTMAP-Vi exhibited an order of magnitude faster degradation rate in hydroxide than Dex-Vi with a k of $6.9 \times 10^{-5}$ s$^{-1}$·M$^{-1/2}$ under identical conditions and assuming the same reaction order (FIG. 13B). Although these kinetic results match well with the improved Dex-Vi stability over BTMAP-Vi in symmetric cell cycling, further studies should be conducted to elucidate the role of the Dex-Vi alcohol moieties in this proposed degradation mechanism and to fully understand the origin of the hydroxide in the anolyte solution.

Figure 14A:
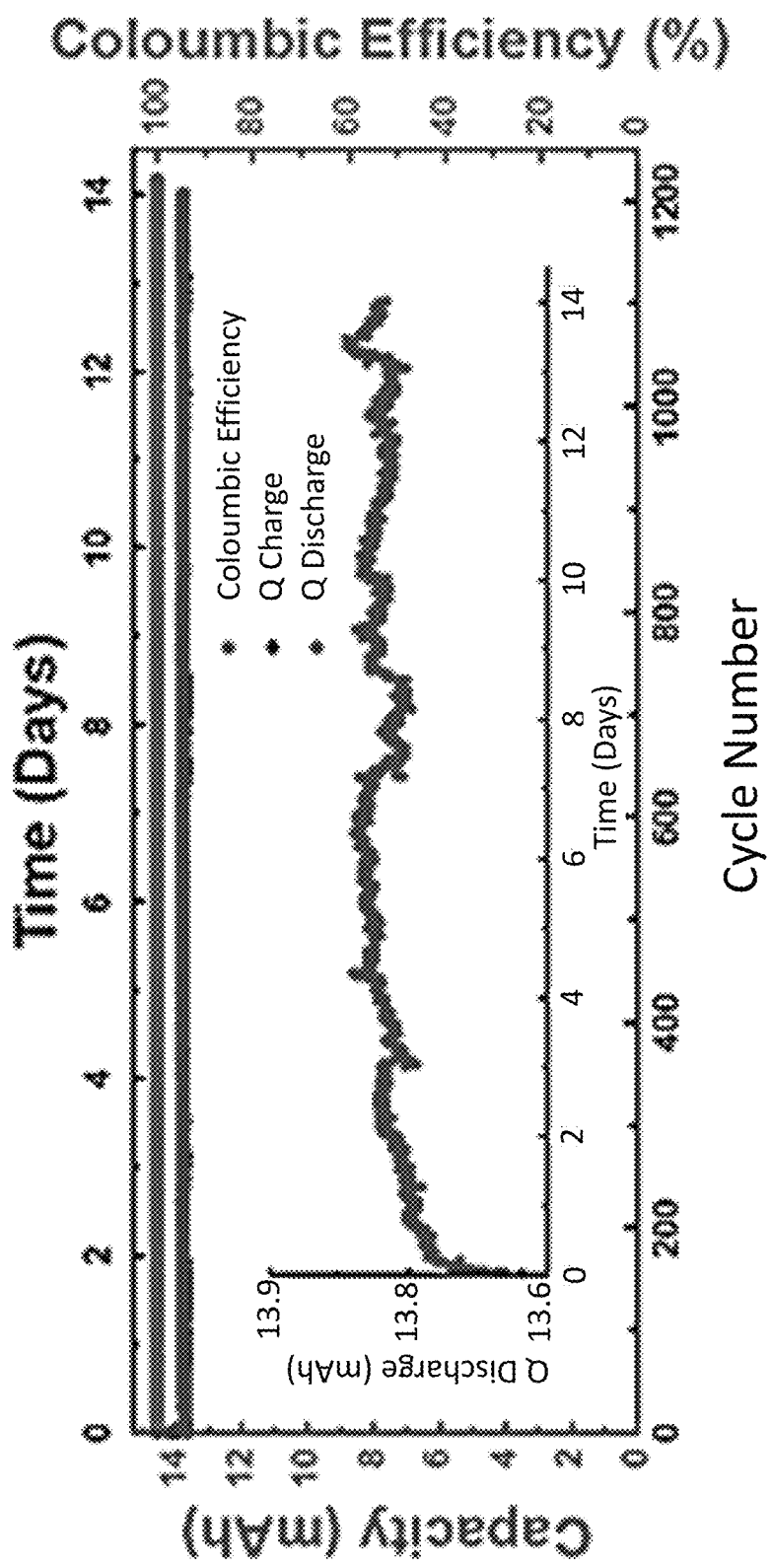
FIG. 14A shows the results of a low-concentration (0.1 M) RFB cycling test of Dex-Vi in an anolyte-limiting configuration, which displayed no observable decay over two weeks of cycling (1,200+ cycles).
Figure 14B:
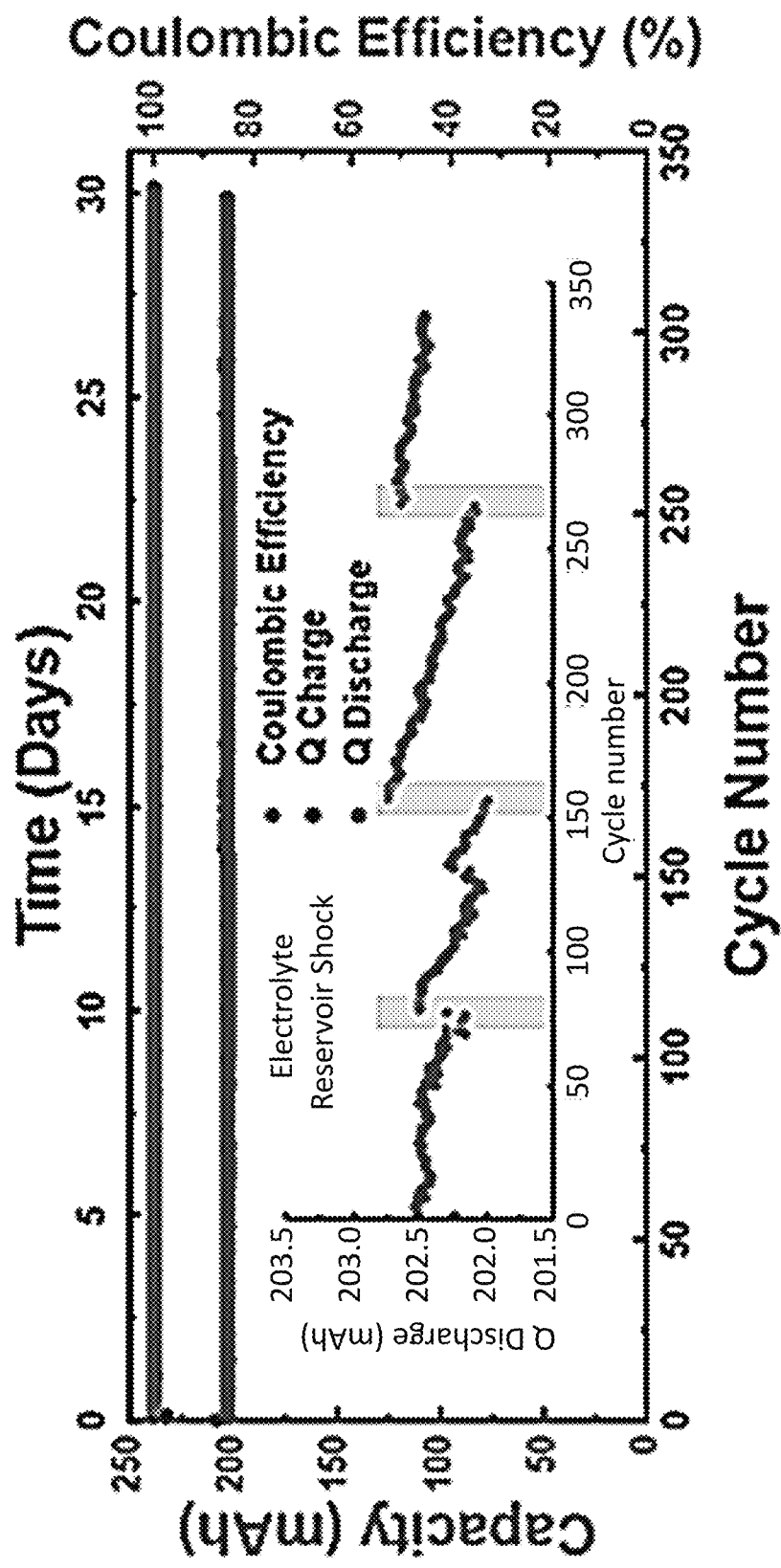
FIG. 14B shows the results of a high-concentration cycling test of Dex-Vi carried out in an anolyte-limiting configuration.

After confirming the superior properties of Dex-Vi, full RFB tests were conducted to evaluate the practical cycling performance of the Dex-Vi anolyte. For full cell experiments, Dex-Vi was paired with BTMAP-Fc, which is a stable catholyte also with low permeance. Although a higher voltage catholyte such as TEMPO could be used to increase cell voltage and power, BTMAP-Fc was selected and used in excess to demonstrate the true stability of the Dex-Vi anolyte as TEMPO and other Ferrocene derivatives (i.e., FcNCl) have crossover concerns that may interfere with the anolyte cycling performance. Pure Dex-Vi was cycled in RFBs to investigate its ideal performance and followed standard current rate variation behavior. A low-concentration (0.1 M) RFB cycling test of Dex-Vi in an anolyte-limiting configuration displayed no observable decay over two weeks of cycling (1,200+ cycles) (FIG. 14A). High concentration cycling was also carried out in an anolyte-limiting configuration to demonstrate the high practical capacity of Dex-Vi (FIG. 14B). Dex-Vi still exhibited no discernable decay after one month of continual cycling at a concentration of 1.5 M (theoretical anolyte volumetric capacity of 40.2 Ah·L$^{-1}$), which is equal to the highest demonstrated concentration for any reported stable organic anolyte redox species in neutral aqueous solution. Post-cycling CV of the catholyte showed minimal Dex-Vi redox feature, confirming good membrane compatibility of Dex-Vi even at high concentration. The stable full cell performance signifies that there was no increase in chemical degradation with increased concentration and that crossover was miniscule, as the Dex-Vi symmetric cell demonstrated a similar decay rate. The decay rate of BTMAP-Vi was reported to be 36.5% per year (0.1% per day) when it was utilized at 1.3 M in an anolyte-limiting cell with BTMAP-Fc catholyte and DSV membrane. Thus, Dex-Vi displays drastically improved capacity retention compared to BTAMP-Vi even at a higher concentration in an anolyte-limiting configuration with the same catholyte and membrane. We attribute the drastically increased capacity retention of Dex-Vi to both its enhanced chemical stability and improved membrane compatibility.

TABLE 1

Summary of the parameter comparison between BTMAP-Vi and Dex-Vi.

| Anolyte | RFB Viologen Molarity (1e$^-$) | DSV Membrane Permeability (cm$^2$/s) | $E_1^0/E_2^0$ (V vs. SHE) | $k_1^0$ (cm/s) | Anolyte-limiting RFB Stability (% decay/year) | Small-batch Cost ($/Ah) |
|---|---|---|---|---|---|---|
| MV | 0.5 | $3.4 \times 10^{-9}$ | −0.450/NA | $2.8 \times 10^{-4}$ | >547.5%* | $419 |
| BTMAP-Vi | 1.5 | $6.7 \times 10^{-10}$ | −0.349/−0.713 | $8.9 \times 10^{-2}$ | 36.5% | $1,089 |
| Dex-Vi | 1.5 | $2.3 \times 10^{-11}$ | −0.322/−0.699 | $5.0 \times 10^{-2}$ | ~0% | $6.8 |

Simple cost analysis (see Supplemental Information for details) reveals that Dex-Vi was synthesized at a raw material cost of $6.8/Ah ($0.30/g) on a lab-scale, whereas commercially available BTMAP-Vi is $1089/Ah ($54.4/g) for a small-batch (TCI Chemicals) when considering the species as one-electron anolytes. The lab-scale raw materials cost of BTMAP-Vi was estimated to be $23/Ah ($1.1/g). The significant difference between estimated BTMAP-Vi raw material cost and commercial cost can be partially attributed to the additional labor and materials costs associated with the intensive ion-exchange procedures, which are not required for Dex-Vi. Although data was not readily available to estimate the mass production (100,000+ Metric Ton) cost of Dex-Vi, the cost of 1 Metric Ton was estimated to be $39/kg. This is unprecedented considering that 2,6-dihydroxy anthraquinone (DHAQ), another promising aqueous anolyte, has a small-batch cost of $113/Ah ($15/g), an estimated cost of $300/kg at the 1 Metric Ton scale, and a mass production cost of $3/kg ($23/kAh) as a two-electron anolyte. If Dex-Vi follows a similar cost-reduction trend to anthraquinone, the mass production cost would be 39$/kg ($8.7/kAh). Furthermore, anthraquinones require additional costly functionalization for increased membrane compatibility, aqueous solubility, and chemical stability and also require highly basic solution (pH>12) to achieve ideal performance, making it difficult to develop a base-stable catholyte with similar volumetric capacity to pair with in practical RFBs. In contrast, Dex-Vi can be readily paired with existing TEMPO and Ferrocene catholytes to enable higher voltage AORFBs with uncompromised volumetric capacity.

Experimental

Synthesis of Dextrosil Viologen 4,4'-dipydridyl and 3-chloro-2-hydroxypropyl trimethylammonium chloride were obtained from Oakridge Chemical and Tokyo Chemical Industry Co., respectively, and used without further purification. Firstly, 12 g (0.077 mol) of 4,4'-dipydridyl was added to 60 mL (0.22 mol) of 3-chloro-2-hydroxypropyl trimethylammonium chloride (65 wt % in water) in an autoclave reactor. The solution was then transferred to a stainless-steel autoclave with PTFE liner (100 mL) and heated to 120° C. for 24 hr. After the reaction, ethanol and then acetone were added to the resultant aqueous solution in sequential order in a 1:9:10 (product:ethanol:acetone) volume ratio to precipitate out the pure product. The off-white product was filtered, washed with acetone, and vacuum dried. A high overall yield of 71% (33 g) was obtained.

Large-batch Dex-Vi synthesis (609 g product) followed the same procedure except used DMF in a 1:6 volume ratio (product aqueous solution:DMF) for purification. DMF was used as the purification solvent in this instance simply to afford larger particle size, permitting facile filtration of such a large quantity on a lab scale. The resultant yield was 70%, similar to small-batch yield.

"Neat" Dex-Vi refers to the aqueous product used directly after autoclaving without the final ethanol and acetone purification step, which serves primarily to remove excess 3-chloro-2-hydroxypropyl trimethylammonium chloride (Dextrosil) salt from the redox species product. The molarity of the neat aqueous product was estimated to be 1.1 M Dex-Vi based on the obtained yield in the given volume and through CV investigation of the diluted product. However, purified Dex-Vi was used for all fundamental studies (structural analysis, solubility, viscosity, CV, EIS, and symmetric cell cycling) to obtain accurate results for pure active redox species unless otherwise noted.

Structure Characterization

A Bruker Avance-400 NMR spectrometer was used to conduct $^1$H-NMR experiment, which was analyzed using the Bruker TopSpin software. Dex-Vi: $^1$H NMR (D$_2$O δ 4.80, 400 MHz): δ 3.30 (s, 9H), 3.71 (quint, 4H), 4.69 (q, 2H), 4.86 (q, 2H), 5.03 (d, 2H). Single crystal data was obtained using a Bruker Quazar APEX2 with a Mo Kα IµS radiation source.

Solubility

A measured amount of Dex-Vi was partially dissolved in pure water. The solution was then centrifuged. The supernatant was decanted, and the volume was measured. The remainder of the solid was dried in a vacuum oven and weighed. Finally, the weight of the remaining Dex-Vi was subtracted from the initial added mass to obtain the amount dissolved in the supernatant, permitting calculation of the maximum soluble concentration. The solubility tests were performed at room temperature of 18° C.

Viscosity

Viscosity measurements were carried out using an Ares G2 rheometer (TA Instruments) with an advanced Peltier system at 25° C.

Permeability 0.33 M Dex-Vi in pure water was separated by an anion-exchange membrane (DSV) from 1 M NaCl in an H-cell. These concentrations were chosen empirically through trial-and-error and showed little osmotic pressure driven water transport through the membrane to balance ion-strength. The cell was agitated on a shaker to partially simulate flow dynamics. Aliquots of the receiving end (1 M NaCl side) were taken every few days, and the removed volume was replaced with 1 M NaCl. The concentration of Dex-Vi in the aliquot was determined by measuring the absorbance at 285 nm using a UV-Vis spectrophotometer. The concentration as a function of time data was then used to calculate the permeability constant of Dex-Vi. (Kwabi, D. G. et al., *Joule* 2018, 2, 1894-1906)

Electrochemical Measurements

CV and EIS experiments were ran using a PalmSens4 potentiostat with the PSTrace software. Electrochemical experiments were performed in 1.0 M NaCl supporting electrolyte using 15 mM of active material at room temperature (18° C.). Formal potentials for the redox couples were estimated by taking the average potential between the cathodic and anodic peak. Diffusional behavior was investigated by varying the scan rate between 10-100 mV·s$^{-1}$ for the first electron reduction and 50-200 mV·s$^{-1}$ for the second electron reduction, and the diffusion constants of the reduced and oxidized states ($D^R$ and $D^O$) were determined via the Randles-Sevcik equation assuming ideal reversible behavior (FIG. 12D). Potentiostatic EIS measurements were used for determination of a combined diffusional constant of the reduced and oxidized states ($D^{EIS}$) and of the standard electron kinetic rate constant ($k^o$). These EIS measurements were performed at the formal reduction potential (held for 30 seconds before measurement) in which the concentration of the two redox states at the electrode surface were assumed to be the same and equal to half of the initially prepared redox species concentration.

Flow Cell Cycling Measurements

The RFB measurements were carried out in a custom-made zero-gap device previously reported by Li et al. (Li, W. et al., *Chem* 2018, 4 (11), 2644-2657; and Li, W. et al., *Adv. Energy Mater.* 2019, 9 (31), 1900918.) Both symmetric flow cell and RFB full cell measurements were conducted using a Bio-Logic SP-200 potentiostat at room temperature (~20° C.). In symmetric cells, 0.1 M of active species in 1 M NaCl (pre-charged to 50% SOC of the first electron reduction using FcNCl as the counter cathode in bulk electrolysis) was utilized on both sides with the capacity limiting side (CLS) consisting of 5 mL of solution and the non-capacity limiting side (NCLS) consisting of 10 mL of solution separated by a Selemion AMV anion-exchange membrane (Asahi Glass Co.). The neat Dex-Vi full RFB cell cycling was performed using the product from the Dex-Vi synthesis directly without any purification. The neat product was diluted to roughly 0.1 M to pair with a 0.2 M BTMAP-Fc counter catholyte in excess capacity separated by an AMV membrane. Both the anolyte and catholyte were 5 mL in total volume with 0.5 M NaCl supporting electrolyte. The first electron high concentration Dex-Vi RFB full cell cycling was performed using 5 mL of 1.5 M Dex-Vi as the anolyte and 10 mL 0.75 M BTMAP-Fc as the catholyte, both of which were prepared in pure water without any supporting salt, with a DSV anion-exchange membrane. The second-electron high concentration full cell cycling was performed using 5 mL of 1.5 M Dex-Vi in water as the anolyte, 20 mL of 0.75 M BTMAP-Fc in water as the catholyte, and a DSV anion-exchange membrane. Rate performance was investigated using 0.1 M Dex-Vi anolyte and 0.2 M BTMAP-Fc catholyte both in 1 M NaCl with DSV anion-exchange membrane.

Supplemental Information

Electrochemical Data

A glassy carbon working electrode (CH Instruments, 0.0707 cm$^2$), a saturated calomel reference electrode (SCE, CH Instruments, +0.241 V vs. SHE), and a platinum wire counter electrode were used for both CV and EIS measurements. The working electrode was polished with 1 μm, 0.3 μm, and 0.05 μm alumina slurry successively. All electrodes were rinsed with deionized water in between measurements.

Randles-Sevcik Analysis

CVs were taken at various scan rates in order to determine the diffusion coefficients via the Randles-Sevcik relation (Eqn. 1) where $i_p$ is the peak current in Amps, n is number of electrons transferred, F is Faraday's constant, A is electrode surface area in cm$^2$, C is the redox species concentration in mole·cm$^{-3}$, R is the ideal gas constant, T is temperature, D is the diffusion coefficient, and v is scan rate in V/s. The anodic peak current ($i_{p,c}$) determines the diffusion coefficient of the reduced state ($D^R$) while the cathodic peak current ($i_{p,a}$) determines the diffusion coefficient of the oxidized state ($D^O$).

$$i_p = 0.4463 n^{3/2} \cdot F^{3/2} \cdot A \cdot C \cdot R^{-1/2} \cdot T^{-1/2} \cdot D^{1/2} \cdot v^{1/2} \qquad \text{Eqn. 1}$$

Accordingly, a $D_2^R$ of $3.1 \times 10^{-6}$ cm$^2$·s$^{-1}$ and a $D_2^O$ of $4.0 \times 10^{-6}$ cm$^2$·s$^{-1}$ were determined for Dex-Vi at the second redox state. A $D_2^R$ of $2.5 \times 10^{-6}$ cm$^2$·s$^{-1}$ and a $D_2^O$ of $2.3 \times 10^{-6}$ cm$^2$·s$^{-1}$ were determined for BTMAP-Vi at the second redox state.

Electrochemical Impedance Spectroscopy

Potentiostatic EIS measurements were taken at the formal potential in which the reduction and oxidation processes are at equilibrium and the concentrations of the reduced and oxidized states can be assumed equal. This permitted simple calculation of the standard kinetic rate constant ($k^o$) via Eqn. 2 where R is the ideal gas constant, T is temperature, n is number of electrons, $R_{CT}$ is the charge-transfer resistance, F is Faraday's constant, A is the electrode surface area in cm$^2$, and C is the concentration of either the oxidized or reduced form at the electrode surface in mole cm$^{-3}$ (which is assumed to be half of the initially prepared redox species concentration, $C = C^O = C^R = 0.5 \ C_{initial}$).

$$k^o = \frac{R \cdot T}{n \cdot R_{CT} \cdot F^2 \cdot A \cdot C} \qquad \text{Eqn. 2}$$

A combined diffusion coefficient of the reduced and oxidized state ($D^{EIS}$) can also be determined using Eqn. 3, where σ is the Warburg diffusional impedance variable and all other variables have the previously defined meaning.

$$\sigma = \frac{2R \cdot T}{F^2 \cdot A \cdot C \cdot \sqrt{2D^{EIS}}} \qquad \text{Eqn. 3}$$

$R_{CT}$ and σ can be determined by fitting the impedance spectrum to the ideal Randles equivalent circuit for a 3-electrode system where $R_u$ is the uncompensated resistance between the working and reference electrode, $R_{CT}$ is the charge transfer resistance between the working electrode and the redox species, $W_D$ is the Warburg diffusional element, and CPE is the constant phase element that represents capacitive behavior of the working electrode.

The raw data was fitted based on this equivalent circuit using the Z-Fitting tool on the PSTrace software and with the Levenberg-Marquardt algorithm across the entire measured frequency range. For the second redox state, $D_2^{EIS}$ were $3.6 \times 10^{-6}$ cm$^2$·s$^{-1}$ and $3.8 \times 10^{-6}$ cm$^2$·s$^{-1}$ and $k_2^o$ were 0.13 cm·s$^{-1}$ and 0.23 cm·s$^{-1}$ for Dex-Vi and BTMAP-Vi, respectively.

Flow Cell Data

Graphite plates (⅛-inch thickness, MWI Inc.) with a 20×20×1.2 mm pocket were used as current collectors for RFB devices. 4 cm$^2$ graphite felt electrodes (GFD 3 EA, SIGRACELL®) were pre-treated at 400° C. in air for 6 hr before being used on both sides of the cell. 25×25 mm Selemion AMV or DSV was presoaked in 1.0 M NaCl for more than 24 hr before it was used as an anion-exchange membrane. The cell was assembled with four pieces of die cut PTFE sheets (0.04-inch thickness) as gaskets and tightened with eight #10-24 bolts. The electrolytes were pumped through the flow channels by a peristaltic pump (Cole-Parmer Masterflex L/S) via PharMed BPT tubing. The electrolyte flow rate was controlled at 20 mL·min$^{-1}$ for all RFB measurements. 10 mL custom made glass vials with two 4 mm OD electrolyte inlet/out arms were used as electrolyte reservoirs. All RFB measurements were carried out in a custom modified $N_2$ flush box (Terra Universal) with continuous $N_2$ flushing, and the glass vials with electrolyte solution were bubbled with $N_2$ for multiple hours before cycling.

Permeability

Permeability was calculated using Eqn. 4 which follows Fick's Law, where P is the permeability in $cm^2 \cdot s^{-1}$, A is the membrane area in $cm^2$, t is elapsed time in seconds, $C_t$ is the concentration ($mol \cdot cm^{-3}$) of Dex-Vi on the receiving side at time t, $C_0$ is the initial concentration of Dex-Vi on the donating side, $V_o$ is the volume of one side of the H-cell, and l is the membrane thickness in cm.

$$P = \frac{\ln\left(1 - \frac{2C_t}{C_0}\right)\left(\frac{V_o l}{2A}\right)}{t} \quad \text{Eqn. 4}$$

Symmetric Cells

Galvanostatic cycling with potential limits (GCPL) was used in symmetric cell cycling tests with a current density of 2.5 mA·cm$^{-2}$ and voltage cutoffs of ±0.125 V to avoid triggering the second redox state. An additional Potentiostatic step was performed each cycle with cut-off currents of half-current (1.25 mA·cm$^{-2}$) and of 0.25 mA·cm$^{-2}$ for the charging and discharging processes, respectively. Potentiostatic EIS measurements of the flow cell were conducted at 0% SOC and at open-circuit voltage with a voltage offset of 10 mV and frequencies ranging from 100 kHz to 1 Hz.

Full Cells

For the "neat" full cell, a current density of 2.5 mA·cm$^{-2}$ was applied using GCPL with a voltage cutoff of +0.75 V and a potentiostatic hold to half-current for charging and a voltage cutoff of +0.30 V and a potentiostatic hold to 0.25 mA·cm$^{-2}$ for discharging. For the one-electron high concentration cell, a current density of 25 mA·cm$^{-2}$ was applied using GCPL with a voltage cutoff of +1.0 V and a potentiostatic hold to half-current for charging and a voltage cutoff of +0.30 V and a potentiostatic hold to 0.25 mA·cm$^{-2}$ for discharging. For the two-electron high concentration cell, a current density of 25 mA·cm$^{-2}$ was applied using GCPL with a voltage cutoff of +1.35 V and a potentiostatic hold to half-current for charging and a voltage cutoff of +0.30 V and a potentiostatic hold to 0.25 mA·cm$^{-2}$ for discharging. For the current rate experiment, the rate was varied between 2.5-12.5 mA·cm$^{-2}$ with voltage cutoffs of +0.95 V and +0.35 V without potentiostatic hold steps.

Cost Analysis

Raw material cost was estimated using available cost data from chemical vendors and the synthetic data reported in this example and previous publications. Eqn. 5 is the general equation used to determine the raw materials cost ($/g) of a given product (P) where R represents a reactant, $MW_p$ is the molecular weight of the product, % Y is the percent yield of the given reaction step, φ is the molar ratio of a given reactant to the product, $MW_R$ is the molecular weight of the reactant, and $C_R$ is the cost of the reactant.

$$C_P = \frac{1}{MW_P \cdot \% Y}\left[(\varphi_{R_1:P} \cdot MW_{R_1} \cdot C_{R_2}) + (\varphi_{R_2:P} \cdot MW_{R_2} \cdot C_{R_2}) + \ldots \right] \quad \text{Eqn. 5}$$

If a reaction involved multiple steps, such as in the case of the synthesis of BTMAP-Vi, $C_P$ of the intermediate was determined and then used as an input $(C_R)$ of the final product calculation. The cost per weight was converted to cost per Ah (or kAh) for a more direct comparison between various redox species. For "lab-scale" (or "small-batch") cost estimation, cost values readily available from chemical vendors were used.

Example 2: In this example, the universal application of the hydrothermal method with various water soluble chloro-functionalization groups is demonstrated, and fundamental structure-property relationships of viologens to guide rationalized design of AORFB anolytes are elucidated.

Figure 15A:
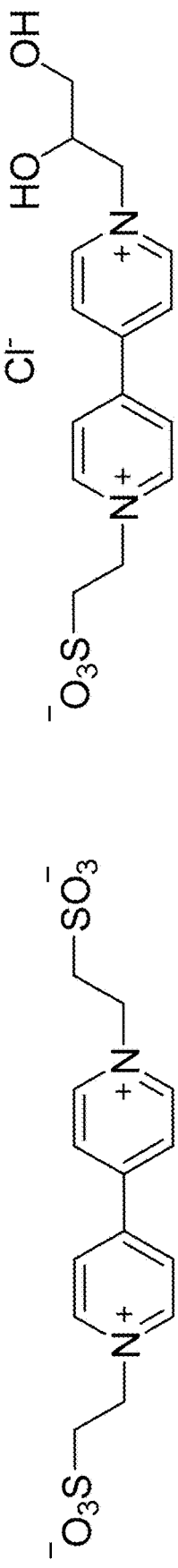
FIGS. 15A and 15B show the structures of ten viologens produced in Example 2.
Figure 15A:
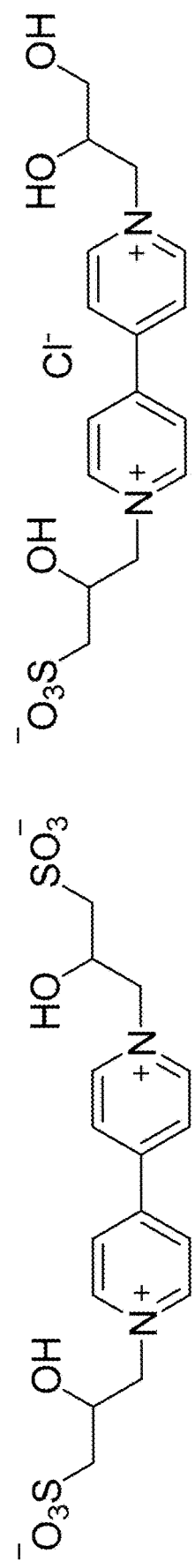
Figure 15B:
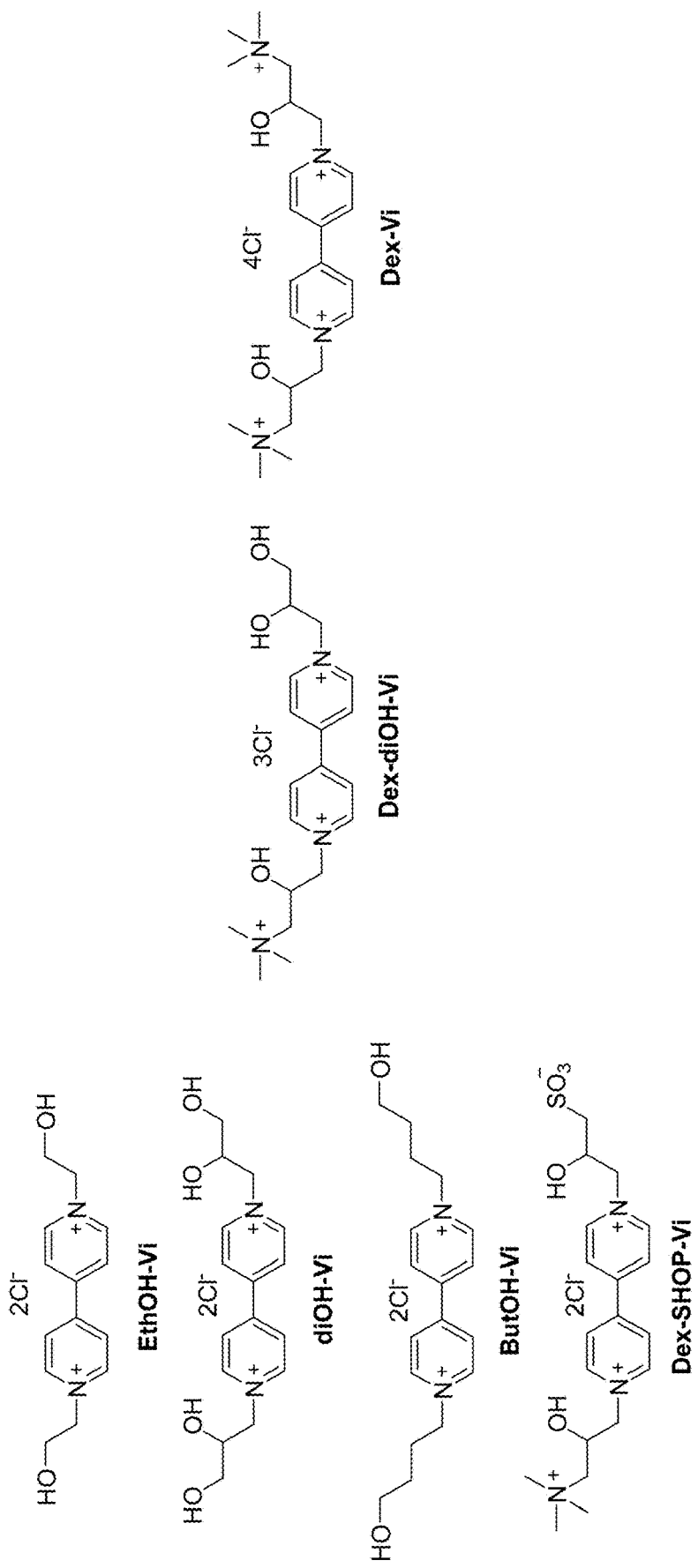

In order to delineate the molecular engineering principles of viologen anolytes, several low-cost, water-soluble organic substitution groups suitable for hydrothermal synthesis were selected. Viologen derivatives of each reactant were synthesized at yields >65% (Table 2) and were structurally confirmed through NMR. High-yields of the di-substituted dipyridine were obtained, which can be attributed to the fact that the starting reagents, mono-substituted intermediates, and product are all highly soluble in water under the elevated thermal conditions. Six symmetric viologens were obtained of varying charge and size for use in electrochemical applications. In addition to the symmetric viologens, the various chloro-containing reactants can be combined to produce numerous asymmetric viologen derivatives through either stepwise or one-pot hydrothermal syntheses. To demonstrate this concept and obtain additional viologens with unique characteristics, four asymmetric viologens were produced, having an overall charge from 0 to +4. In total, ten viologens were produced with high-yield and high-purity to dramatically expand this anolyte class (FIGS. 15A and 15B).

TABLE 2

The synthetic yields of the viologens produced via hydrothermal synthesis

| | Synthetic Yield (%) |
|---|---|
| Dex-Vi | 73.3 |
| SHOP-Vi | 89 |
| DiOH-Vi | 65 |
| EtS-Vi | 75 |
| EtOH-Vi | 70 |
| Dex-DiOH-Vi | 65.27 |
| ButOH-Vi | 40 |
| DiOH-SHOP-Vi | 56.55 |
| DiOH-EtS-Vi | 64.17 |
| Dex-SHOP-Vi | 86.25 |

The hydrothermal viologen derivatives were characterized electrochemically (Table 3), physiochemically (Table 4 and Table 5), and chemically (Table 6).

TABLE 3

Electrochemical characterization of the produced hydrothermal viologens.

| | CV | | | EIS | | |
|---|---|---|---|---|---|---|
| | $E^0$ (V vs. SHE) | $D_{red}$ (cm$^2$/s) | $D_{ox}$ (cm$^2$/s) | D (cm$^2$/s) | $i^0$ (A) | $k^0$ (cm/s) |
| Dex-Vi | −0.3203 | 2.50E−06 | 2.39E−06 | 3.51645E−06 | 6.57E−04 | 1.28E−02 |
| SHOP-Vi | N/A | N/A | N/A | N/A | N/A | N/A |
| DiOH-Vi | −0.3664 | 4.39E−06 | 3.76E−06 | 6.62176E−06 | 1.14E−03 | 2.22E−02 |
| EtS-Vi | −0.3414 | 3.39E−06 | 3.28E−06 | 5.2921E−06 | 3.47E−03 | 6.77E−02 |
| EtOH-Vi | −0.3825 | 6.48E−06 | 5.43E−06 | 9.86768E−06 | 4.53E−03 | 8.85E−02 |
| Dex-DiOH-Vi | −0.3424 | 4.02E−06 | 3.49E−06 | 5.56175E−06 | 6.20E−03 | 1.21E−01 |
| ButOH-Vi | −0.4249 | 3.34E−05 | 1.84E−05 | 2.36047E−05 | 1.25E−05 | 2.44E−04 |
| DiOH-SHOP-Vi | −0.3516 | 2.84E−06 | 3.57E−06 | 5.41903E−06 | 4.06E−03 | 7.94E−02 |
| DiOH-EtS-Vi | −0.3537 | 5.25E−06 | 4.94E−06 | 8.13394E−06 | 7.76E−03 | 1.52E−01 |
| Dex-SHOP-Vi | −0.3291 | 2.52E−06 | 3.04E−06 | 4.49747E−06 | 1.57E−03 | 3.07E−02 |

TABLE 4

| | Water Solubility (M) | Viscosity at 1M, 25° C.(cP) |
|---|---|---|
| Dex-Vi | 1.80 | 14.2 |
| SHOP-Vi | <0.5 | — |
| DiOH-Vi | 1.99 | 3.0 |
| EtS-Vi | 0.53 | — |
| EtOH-Vi | 2.51 | 2.4 |
| Dex-DiOH-Vi | 1.73 | 3.9 |
| ButOH-Vi | 1.36 | 1.6 |
| DiOH-SHOP-Vi | <0.5 | — |
| DiOH-EtS-Vi | 1.26 | 2.9 |
| Dex-SHOP-Vi | 1.27 | — |

TABLE 5

| | Permeability | |
|---|---|---|
| | Permeability (cm$^2$/s) | Type of Membrane |
| Dex-Vi | 2.02E−11 | DSVN |
| SHOP-Vi | N/A | N/A |
| DiOH-Vi | 1.47E−10 | DSMV |
| EtS-Vi | 1.58E−10 | Naf 117 |
| EtOH-Vi | 3.32E−10 | DSVN |
| Dex-DiOH-Vi | 3.26E−11 | DSVN |
| ButOH-Vi | 7.09E−09 | DSVN |
| DiOH-SHOP-Vi | N/A | N/A |
| DiOH-EtS-Vi | N/A | N/A |
| Dex-SHOP-Vi | 1.57E−12 | Naf 117 |

TABLE 6

| | Degradation in 1M KOH, k (s$^{-1}$) |
|---|---|
| Dex-Vi | 3.22E−06 |
| SHOP-Vi | 1.04758E−06 |
| DiOH-Vi | 2.29633E−06 |
| EtS-Vi | N/A |
| EtOH-Vi | N/A |
| Dex-DiOH-Vi | 4.06E−06 |
| ButOH-Vi | N/A |
| DiOH-SHOP-Vi | N/A |
| DiOH-EtS-Vi | 4.40E−06 |
| Dex-SHOP-Vi | 86.25 |

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" can mean only one or can mean "one or more." Embodiments of the inventions consistent with either construction are covered.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A 4,4'-dipyridinium derivative comprising a 4,4'-dipyridinium group, wherein a nitrogen atom of at least one pyridinium ring of the 4,4'-dipyridinium group has a substituent comprising a secondary alcohol on an alkyl chain with a terminal ammonium group, and further wherein neither of the pyridinium rings of the 4,4'-dipyridinium group has a substituent comprising a substituted aryl group.

2. The 4,4'-dipyridinium derivative of claim 1, wherein the 4,4'-dipyridinium derivative has the structure:

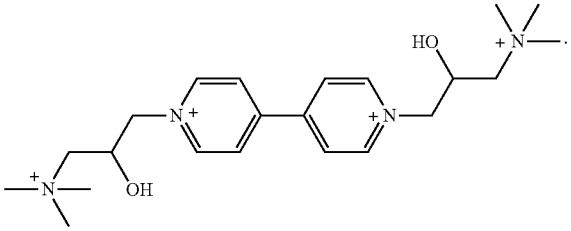

3. The 4,4'-dipyridinium derivative of claim 1, wherein the 4,4'-dipyridinium derivative is an asymmetric 4,4'-dipyridinium derivative.

4. The 4,4'-dipyridinium derivative of claim 1, wherein the 4,4'-dipyridinium derivative is a symmetric 4,4'-dipyridinium derivative.

5. The 4,4'-dipyridinium derivative of claim 1, wherein the 4,4'-dipyridinium derivative has the structure:

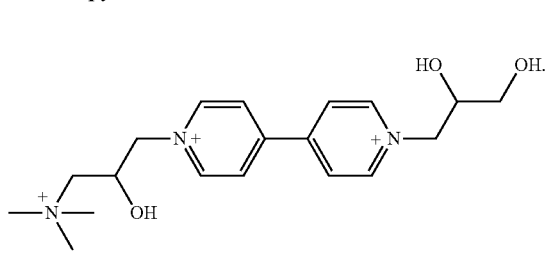

6. The 4,4'-dipyridinium derivative of claim 1, wherein the 4,4'-dipyridinium derivative has the structure:

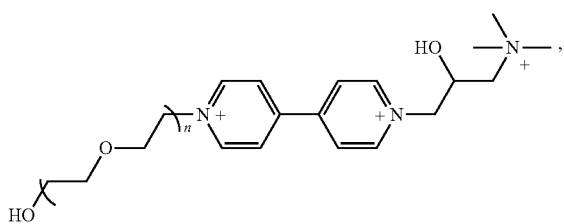

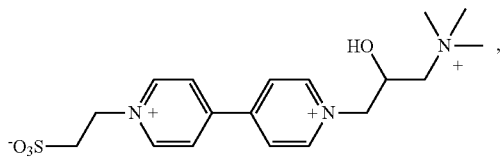

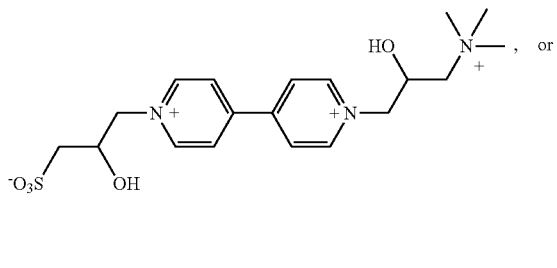

where n is an integer in the range from 1 to 5.

7. An electrochemical cell comprising:
 an anode;
 an anolyte in contact with the anode, the anolyte comprising the 4,4'-dipyridinium derivative of claim 1;
 a cathode;
 a catholyte in contact with the cathode; and
 a membrane between the anolyte and the catholyte.

8. The electrochemical cell of claim 7, wherein the electrochemical cell is an aqueous flow battery.

* * * * *